(12) United States Patent
Romero-Ortega et al.

(10) Patent No.: US 12,311,164 B2
(45) Date of Patent: May 27, 2025

(54) DEVICES AND METHODS FOR NEUROMODULATION

(71) Applicants: Board of Regents, The University of Texas System, Austin, TX (US); National Autonomous University of Mexico, Mexico City (MX)

(72) Inventors: Mario I. Romero-Ortega, Coppell, TX (US); Margarita Martinez-Gomez, Tlaxcala (MX); Stuart F. Cogan, Dallas, TX (US); Aswini Kanneganti, Richardson, TX (US)

(73) Assignees: Board of Regents, The University of Texas System, Austin, TX (US); National Autonomous University of Mexico, Mexico City (MX)

( * ) Notice: Subject to any disclaimer, the term of this patent is extended or adjusted under 35 U.S.C. 154(b) by 311 days.

(21) Appl. No.: 16/414,169

(22) Filed: May 16, 2019

(65) Prior Publication Data

US 2019/0290902 A1 Sep. 26, 2019

Related U.S. Application Data

(63) Continuation-in-part of application No. 16/185,285, filed on Nov. 9, 2018.
(Continued)

(51) Int. Cl.
*A61N 1/36* (2006.01)
*A61N 1/05* (2006.01)

(52) U.S. Cl.
CPC ......... *A61N 1/0556* (2013.01); *A61N 1/0524* (2013.01); *A61N 1/36007* (2013.01); *A61N 1/36064* (2013.01); *A61N 1/36107* (2013.01)

(58) Field of Classification Search
CPC .................. A61N 1/36017; A61N 1/0056
See application file for complete search history.

(56) References Cited

U.S. PATENT DOCUMENTS 3,157,181 A 11/1964 McCarty
3,421,511 A 1/1969 Schwartz et al.
(Continued)

FOREIGN PATENT DOCUMENTS

FR         3059476 A1    6/2018
WO   2006131912 A2   12/2006
(Continued)

OTHER PUBLICATIONS

U.S. Appl. No. 16/185,285, Office Action dated Feb. 5, 2021, 23 pages.
(Continued)

*Primary Examiner* — William J Levicky
(74) *Attorney, Agent, or Firm* — Nutter McClennen & Fish LLP

(57) ABSTRACT

In one aspect, a neuromodulation device is described herein. In some embodiments, a neuromodulation device comprises a chamber operable to receive a nerve, at least one electrode disposed in the chamber, and a channel defined by two walls. In some embodiments, the channel of the device is in fluid communication with an interior of the chamber and an external surface of the device. In another aspect, methods of neuromodulation are described herein. In some embodiments, methods described herein can use one or more neuromodulation devices described herein.

6 Claims, 32 Drawing Sheets

Related U.S. Application Data

(60) Provisional application No. 62/584,195, filed on Nov. 10, 2017, provisional application No. 62/584,203, filed on Nov. 10, 2017.

(56) References Cited

U.S. PATENT DOCUMENTS

| | | | |
|---|---|---|---|
| 3,654,933 | A | 4/1972 | Hagfors |
| 4,487,210 | A * | 12/1984 | Knudsen .............. A61N 1/0541 607/137 |
| 5,038,781 | A * | 8/1991 | Lynch ................. A61N 1/36003 607/66 |
| 5,282,468 | A | 2/1994 | Klepinski |
| 5,824,027 | A * | 10/1998 | Hoffer .................. A61N 1/0556 600/377 |
| 6,308,105 | B1 | 10/2001 | Duysens et al. |
| 8,473,074 | B2 | 6/2013 | North et al. |
| 8,652,187 | B2 | 2/2014 | Wells et al. |
| 9,186,509 | B2 | 11/2015 | Nelson et al. |
| 9,254,382 | B2 | 2/2016 | Ahmad et al. |
| 9,393,411 | B2 | 7/2016 | Bhadra et al. |
| 9,446,245 | B2 | 9/2016 | Grill et al. |
| 9,492,660 | B2 | 11/2016 | Mouchawar et al. |
| 9,517,338 | B1 | 12/2016 | Jiang et al. |
| 9,623,253 | B2 | 4/2017 | Perryman et al. |
| 9,539,433 | B1 | 10/2017 | Wirbisky et al. |
| 10,258,789 | B2 | 4/2019 | Tischendorf et al. |
| 10,367,178 | B2 | 7/2019 | Fenton et al. |
| 10,512,778 | B2 | 12/2019 | Parramon et al. |
| 10,576,291 | B2 | 3/2020 | Manicka |
| 10,596,368 | B2 | 3/2020 | Renaux |
| 10,987,060 | B1 | 4/2021 | Manicka et al. |
| 10,994,139 | B2 | 5/2021 | Fayram et al. |
| 11,097,122 | B2 | 8/2021 | Lu |
| 11,318,315 | B2 | 5/2022 | Hartley et al. |
| 11,338,127 | B2 | 5/2022 | Huertas Fernandez et al. |
| 11,565,109 | B2 | 1/2023 | Denison et al. |
| 11,717,689 | B2 | 8/2023 | Maharbiz et al. |
| 2002/0055761 | A1 | 5/2002 | Mann et al. |
| 2002/0120309 | A1 | 8/2002 | Richmond et al. |
| 2003/0100930 | A1 | 5/2003 | Cohen et al. |
| 2007/0129780 | A1* | 6/2007 | Whitehurst .......... A61N 1/0556 607/118 |
| 2010/0126711 | A1 | 5/2010 | Buss et al. |
| 2010/0274310 | A1 | 10/2010 | Boggs, II et al. |
| 2012/0197336 | A1* | 8/2012 | Su ...................... A61N 1/36171 607/40 |
| 2012/0197356 | A1* | 8/2012 | Wei .................... A61N 1/36171 607/74 |
| 2013/0090542 | A1 | 4/2013 | Kipke et al. |
| 2017/0182319 | A1 | 6/2017 | Chancellor et al. |
| 2017/0246453 | A1* | 8/2017 | Fang ................. A61N 1/36171 |
| 2018/0093099 | A1 | 4/2018 | Cogan et al. |
| 2018/0099139 | A1 | 4/2018 | Black et al. |
| 2018/0154143 | A1 | 6/2018 | Haessler et al. |
| 2019/0060641 | A1 | 2/2019 | Schuttler et al. |
| 2019/0143102 | A1 | 5/2019 | Romero-Ortega et al. |
| 2020/0155844 | A1 | 5/2020 | John et al. |
| 2020/0171304 | A1 | 6/2020 | Simon et al. |
| 2020/0384261 | A1 | 12/2020 | Chasensky et al. |
| 2021/0030488 | A1 | 2/2021 | Sachs |
| 2021/0052893 | A1 | 2/2021 | Suri et al. |
| 2021/0101007 | A1 | 4/2021 | Hamner et al. |
| 2021/0187291 | A1 | 6/2021 | Tyer et al. |
| 2021/0290949 | A1* | 9/2021 | Holinski ............... A61N 1/0556 |
| 2021/0308462 | A1 | 10/2021 | Carmena et al. |
| 2022/0054825 | A1 | 2/2022 | Shepherd et al. |
| 2022/0062625 | A9 | 3/2022 | Smith et al. |
| 2023/0149709 | A1 | 5/2023 | Romero-Ortega et al. |
| 2024/0024667 | A1 | 1/2024 | Coates et al. |
| 2024/0024668 | A1 | 1/2024 | Coates et al. |
| 2024/0307687 | A1 | 9/2024 | Mishra et al. |

FOREIGN PATENT DOCUMENTS

| | | |
|---|---|---|
| WO | 2013/150524 A1 | 10/2013 |
| WO | 2018/022838 A1 | 2/2018 |
| WO | 2020106986 A1 | 5/2020 |
| WO | 2020231440 A1 | 11/2020 |
| WO | 2021/077022 A1 | 4/2021 |

OTHER PUBLICATIONS

International Search Report issued in PCT/US2019/032691 mailed Jul. 18, 2019.

Written Opinion issued in PCT/US2019/032691 mailed Jul. 18, 2019.

Wei et al, "Iterative Electrodes Increase Neural Recruitment for Deep Brain Stimulation", IEEE, pp. 3419-3422, (2015).

Vitek, "Mechanisms of Deep Brain Stimulation: Exhibition or Inhibition", Movement Disorders, vol. 17, Suppl. 3, pp. S69-S72, Mar. 25, 2002.

Morris et al, "Effects of Electrode Configurtion and Stimulus Level on Rate and Level Discrimination with Cochlear Implants", JARO, pp. 211-223, Oct. 17, 2000.

Shah et al., "In vivo electrical stimulation of rabbit retina: Effect of stimulus duration and electrical field orientation", Experimental Eye Research, vol. 83, pp. 247-254, (2006).

Rattay et al., "Mechanisms of Electrical Stimulation with Neural Prostheses", Neuromodulation, vol. 6, No. 1, pp. 42-56, (2003).

Maynard et al., "The Utah Intracortical Electrode Array: a recording structure for potential brain-computer interfaces", Electroencephalography and clinical Neurophysiology, vol. 102, pp. 228-239, (1997).

Hu et al., "Scientiic profile of brain-computer interfaces: Bibliometric analysis in a 10-year period", Neuroscience Letters, vol. 635, pp. 61-66, Oct. 14, 2016.

Clements et al., "Regenerative Scaffold Electrodes for Peripheral Nerve Interfacing", IEEE Transactions on Neural Systems and Rehabilitation Engineering, vol. 21, No. 4, pp. 554-566, Jul. 2013.

Judy, "Neural Interfaces for Upper-Limb Prosthesis Control", IEEE Pulse, pp. 57-60, Mar. 22, 2012.

Thakor et al., "Bidirectional Peripheral Nerve Interface and Applications", IEEE, pp. 6327-6330, (2016).

Patel et al., "Insertion of linear 8.4 μm diameter 16 channel carbon fiber electrode for single unit recordings", J Neural Eng, vol. 12, No. 4, (2015) (38 pages).

Patel et al., "Chronic In Vivo Stability Assessment of Carbon Fiber Microelectrode Arrays", J Neural Eng, vol. 13, No. 6, Oct. 5, 2016.

Naples, et al., "A Spiral Nerve Cuff Electrode for Peripheral Nerve Stimulation", IEEE Transactions on Biomedical Engineering, vol. 35, No. 11, pp. 905-916, Nov. 1998.

Xue, et al., "Polymeric C-shaped cuff electrode for recording of peripheral nerve signal", Sensors and Actuators B: Chemical, pp. 640-648, (2015).

Kang et al., "Self-Closed Parylene Cuff Electrode for Peripheral Nerve Recording", Journal of Microelectromechanical Systems, vol. 24, No. 2, pp. 319-332, Apr. 2015.

Arreaga-Salas et al, "Integration of High-Charge-Injection-Capacity Electrodes onto Polymer Softening Neural Interfaces", ACS Applied Materials & Interfaces, vol. 7, pp. 26614-26623, Nov. 17, 2015.

Loeb et al., "Cuff electrodes for chronic stimulation and recording of peripheral nerve activty", Journal of Neuroscience Methods, vol. 64, pp. 95-103, (1996).

Sunderland et al., "Stress-Strain Phenomena in Human Peripheral Nerve Trunks", Brain, vol. 84, No. 1, pp. 102-119, 1961.

Raffe, "Principles of Peipheral Nerve Repair", Textbook of Small Animal Orthopaedics, Jan. 1, 1985 (26 pages).

Kwan et al., "Strain, stress and stretch of peripheral nerve Rabbit experiments in vitro and in vivo", Acta Orthopaedica Scandinavica, vol. 63, No. 3, pp. 267-272, (1992).

Rickett et al., "Functional and Mechanical Evaluation of Nerve Stretch Injury", J Med Syst, vol. 35, pp. 787-793, Apr. 6, 2010.

(56) References Cited

OTHER PUBLICATIONS

Cho et al., "Biocompatible SU-8-Based Microprobes for Recording Neural Spike Signals From Regenerated Peripheral Nerve Fibers", IEEE Sensors Journal, vol. 8, No. 11, pp. 1830-1836, Nov. 2008.
Mcdonald D.M., et al., Morphology of the rat carotid sinus nerve., J. Neurocytology, vol. 12, pp. 373-392 (1983).
Naples G.G., et al., "A Spinal Nerve Cuff Electrode for Peripheral Nerve Stimulation," IEEE Trans. Bio. Eng., vol. 35, Issue No. 11, pp. 905-916 (Nov. 1988).
Navarro X., et al., "A critical review of interfaces with the peripheral nervous system for the control of neuroprostheses and hybrid bionic systems," J. Peripheral Nerv. Sys., vol. 10, pp. 229-258 (2005).
Negi S., et al., "Neural Electrode Degradation from Continuous Electrical Stimulation: Comparison of Sputtered and Activated Iridium Oxide," J. Neurosci. Meth., vol. 186, Issue No. 1 (Jan. 2010).
Ordonez J.S., et al., "Cuff Electrodes for Very Small Diameter Nerves—Prototyping and First Recordings In Vivo," IEEE, pp. 6846-6849 (2014).
Otchy, T.M., et al., "Printable microscale interfaces for long-term peripheral nerve mapping and precision control", Nature Communications 11, 4191 (2020), retrieved from the internet at //https://doi.org/10.1038/s41467-020-18032-4//, 16 pages.
Park S., et al., "Nanopourous Pt Microelectrode for Neural Stimulation and Recording: In Vitro Characterization," J. Phys. Chem. C., vol. 114, pp. 8721-8726 (2010).
Potter K.A., et al., "Stab injury and device implantation within the brain results in inversely multiplastic neuroinflammatory and neurodegenerative responses," J. Neural Eng., vol. 9, 14 pages (2012).
Poulin P., et al., "Superflexibility of graphene oxide," Proceedings of the National Academy of Sciences of the U.S.A., vol. 113, Issue No. 40, pp. 11088-11093 (Oct. 2016).
Qi D., et al., "Design of Architectures and Materials in In-Plane Micro-supercapacitors: Current Status and Future Challenges," Adv. Mater., vol. 29, pp. 1602802-1-1602802-19 (2017).
Restaino S.M., et al., "Biomechanical and functional variation in rat sciatic nerve following cuff electrode implantation," J. Neuro. Rehab., vol. 11, Issue No. 73, 10 pages (2014).
Rho H., et al., "Metal nanfibrils embedded in long free-standing carbon nanotube fibers iwth a high critical current display," NPG Asia Materials, vol. 10, pp. 146-155 (2018).
Rivnay J., et al., "Next-generation probes, particles, and proteins for neural interfacing," Science Advances, vol. 3, pp. e1601649-1-e1601649-20 (Jun. 2017).
Rutten W.L.C., et al., "Selective Electrical Interfaces with the Nervous System," Annu. Rev. Biomed. Eng., vol. 4, pp. 407-452 (2002).
Sahni D., et al., Biocompatibility of pristine graphene for neuronal interface, J. Neurosurg. Pediatrics, vol. 11, pp. 575-583 (2013).
Schrimer K.S.U., et al., "Conductive Composite Fibres from Reduced Graphene Oxide and Polypyrrole Nanoparticles," J. Mat. Chem. B., 10 pages (2013).
Sevcencu C., et al., "A neural blood pressure marker for bioelectronic medicines for treatment of hypertension," Biosensors and Bioelectronics, vol. 98, 6 pages (2017).
Stein R.B., et al., "Principles Underlying New Methods for Chronic Neural Recording," Le J. Canadien Des Sci. Neuro., pp. 235-244 (Aug. 1975).
Tan D.W., et al., "Stability and selectivity of a chronic, multi-contact cuff electrode for sensory stimulation in human amputees," J. Neural Eng., vol. 12, 10 pages (2015).
Tjoa V., et al., "Facile Photochemical Synthesis of Graphene-Pt Nanoparticle Composite for Counter Electrode in Dye Sensitized Solar Cell," ACS Appl. Mater. Interfaces, pp. 3447-3452 (2012).
Tong W., et al., "Optimizing growth and post treatment of diamond for high capacitance neural interfaces," Biomaterials, vol. 104, pp. 32-42 (2010).
Tybrandt K., et al., "High-Density Stretchable Electrode Grids for Chronic Neural Recording," Adv. Mater., vol. 30, pp. 1706520-1-1706520-7 (2018).
Venkatraman S., et al., "In Vitro and In Vivo Evaluation of PEDOT Microelectrodes for Neural Stimulation and Recording," IEEE Trans. Neural Sys. Rehab. Eng., vol. 19, Issue No. 3 (Jun. 2011).
Vince V., et al., "Anti-TNF-a reduces the inflammatory reaction associated with cuff electrode implantation around the sciatic nerve," J. Neuro., vol. 165, pp. 121-128 (2005).
Vitale F., et al., "Fluidic Microactuation of Flexible Electrodes for Neural Recording," Nano Letters, 10 pages (Dec. 2017).
Vitale F., et al., "Neural Stimulation and Recording with Bidirectional, Soft Carbon Nanotube Fiber Microelectrodes," ACS Nano, vol. 9, Issue No. 4, pp. 4465-1174 (2015).
Wang J., et al., "Carbon Nanotube Fiber Microelectrodes," J. Am. Chm. Soc., vol. 125, pp. 14706-14707 (2003).
Wang K., et al., "High-Performance Graphene-Fiber-Based Neural Recording Microelectrodes," Adv. Mater., vol. 31, pp. 1805867-1-1805867-10 (2019).
Wang K., et al., "Neural Stimulation with a Carbon Nanotube Microelectrode Array," Nano Lett., vol. 6, Issue No. 9, pp. 2043-2048 (2006).
Wang M., et al., "Nanotechnology and Nanomaterials for Improving Neural Interfaces," Adv. Funct. Mater., pp. 1700905-1 1700905-28 (2017).
Weiland J.D., et al., "In Vitro Electrical Properties for Iridium Oxide Versus Titanium Nitride Stimulating Electrodes," IEEE Trans. Bio. Eng., vol. 49, Issue No. 12, pp. 1574-1579 (Dec. 2002).
Weremfo A., et al., "Investigating the Interfacial Properties of Electrochemically Roughened Platinum Electrodes for Neural Stimulation," Langmuir, vol. 31, pp. 2593-2599 (2015).
Wilks S.J., et al., "Poly(3,4-ethylenedioxythiophene) as a microneural interface material for electrostimulation," Frontiers in Neuroengineering, vol. 2, Article 7, pp. 1-8 (Jun. 2009).
Wodlinger B., "Recovery of neural activity from nerve cuff electrodes," 33rd Annual International Conf. of the IEEE EMBS, Boston, Massachusetts, 4 pages (Aug.-Sep. 2011).
Won S.M., et al., "Recent Advances in Materials, Devices, and Systems for Neural Interfaces," Adv. Mater., vol. 30, pp. 1800534-1-1800534-19 (2018).
Yoon I., et al., "Intracellular Neural Recording with Pure Carbon Nanotube Probes," PLoS One, vol. 8, Issue No. 6, pp. e65715-1-e65715-6 (Jun. 2013).
Zhang H., et al., Tissue-Compliant Neural Implants from Microfabricated Carbon Nanotube Multilayer Composite, ACS Nano, vol. 7, Issue No. 9, pp. 7619-7629 (2013).
Zhao S., et al., "Programmable Hydrogel Ionic Circuits for Biologically Matched Electronic Interfaces," Adv. Mater., vol. 30, pp. 1800598-1-1800598-10 (2018).
Zheng X., et al., "Hierarchically porous sheath-core graphene-based fiber-shaped supercapacitors with high energy density," J. Mater. Chem. A., vol. 6, pp. 896-907 (2018).
Zhou W., et al., "Single wall carbon nanotube fibers extruded from super-acid suspensions: Preferred orientation, electrical, and thermal transport," J. Appl. Phy., vol. 95, Issue No. 2, pp. 649-655 (Jan. 2004).
Aboutalebi S.H., et al., "High-Performance Multifunctional Graphene Yarns: Toward Wearable All-Carbon Energy Storage Textiles," ACS Nano, vol. 8, Issue No. 3, pp. 2456-2466 (2014).
Barrese J.C., et al.,"Scanning electron microscopy of chronically implanted intracortical microelectrode arrays in non-human primates," J. Neural Eng., vol. 13, Issue No. 2, 44 pages (Apr. 2016).
Birmingham K., et al., "Bioelectronic medicines: a research roadmap," Nature Reviews, Drug Discovery, vol. 13, pp. 399-400 (Jun. 2014).
Boehler C., et al., "Nanostructured platinum grass enables superior impedance reduction for neural microelectrodes," Biomaterials, Department of Microsystems (IMTEK), University of Freiburg, vol. 67, pp. 346-353 (2015).
Boretius T., et al., "On the Stability of Poly-Ethylenedioxythiopene as Coating Material for Active Neural Implants," Artificial Organs, vol. 35, Issue No. 3, pp. 245-248 (2011).

(56) References Cited

OTHER PUBLICATIONS

Brummer S.B., et al., "Criteria for Selecting Electrodes for Electrical Stimulation: Theoretical and Practical Considerations," EIC Laboratories, Inc., 13 pages (1983).
Charkhkar H., et al., Chronic intracortical neural recordings using microelectrode arrays coated with PEDOT-TFB, Science Direct, 41 pages (2019).
Cheng C., et al., "A Water-Processable and Bioactive Multivalent Graphene Nanoink for Highly Flexible Bioelectronic Films and Nanofibers," Advanced Materials, pp. 1705452-1-1705452-11 (2017).
Cheng C., et al., "Functional Graphene Nanomaterials Based Architectures: Biointeractions, Fabrications, and Emerging Biological Applications," Chemical Reviews, vol. 117, pp. 1826-1914 (2017).
Christensen M.B., et al., "The foreign body response and morphometric changes associated with mesh-style peripheral nerve cuffs," Acta Biomaterialia, vol. 67, pp. 79-86 (2018).
Christie B.P., et al., "Long-term disability of stimulating spiral nerve cuff electrodes on human peripheral nerves," J. NeuroEngineering and Rehabilitation, vol. 17, Issue No. 70 (2017).
Cogan S.F., "Over-pulsing degrades activated iridium oxide films used for intracortical neural stimulation," J. Neuroscience Methods, vol. 137, pp. 141-150 (2004).
Cogan S.F., et al., "In Vitro Comparison of the Charge-Injection Limits of Activated Iridium Oxide (AIROF) and Platinum-Iridium Microelectrodes," IEEE Trans. Bio. Eng., vol. 52, Issue No. 9, pp. 1612-1614 (Sep. 2005).
Cogan S.F., et al., "Neural Stimulation and Recording Electrodes," Annu. Rev. Biomed. Eng., vol. 10, pp. 275-309 (2008).
Cogan S.F., et al., "Tissue damage thresholds during therapeutic electrical stimulation," J. Neural Eng., vol. 13, 13 pages (2016).
Cortes-Salazar F., et al., "Parylene C coated microelectrodes for scanning electrochemical microscopy," Electrochimica Acta, vol. 110, pp. 22-29 (2013).
Esrafilzadeh D., et al. "High-performance multifunctional graphene-PLGA fibers: toward biomimetic and conducting 3D scaffolds," University of Wollongong Australia, 38 pages (2016).
Fontes M.B.A., et al., "Electrodes for bio-application: recording and stimulation," 8th Ibero-American Congress on Sensors (Ibersensor 2012), Journal of Physics: Conference Series 421, 7 pages (2013).
Ganji M., et al., "Development and Translation of PEDOT:PSS Microelectrodes for Intraoperative Monitoring," Advanced Functional Materials, pp. 1700232-1-1700232-11 (2017).
Garrett D.J., et al., "Ultra-nanocrystalline diamond electrodes: optimization towards neural stimulation applications," J. Neural Eng., vol. 9, pp. 1-10 (2012).
Gerwig R., et al., "PEDOT-CNT composite microelectrodes for recording and electrostimulation applications: fabrication, morphology, and electrical properties," Frontiers in Neuroengineering, vol. 5, Article No. 8, pp. 1-11 (May 2012).
Green R.A., et al., "Conducting polymers for neural interfaces: Challenges in developing an effective long-term implant," Biomaterials, vol. 29, pp. 3393-3399 (2008).
Green R.A., et al., "Impact of co-incorporating laminin peptide dopants and neurotrophic growth factors on conducting polymer properties," Acta Biomaterialia, vol. 6, pp. 63-71 (2010).
Green R.A., et al., "Substrate dependent stability of conducting polymer coating on medical electrodes," Biomaterials, vol. 33, pp. 5875-5866 (2012).
Guitchounts G., et al., "A carbon-fiber electrode array for long-term neural recording," J. Neural Eng., vol. 10, pp. 1-13 (2013).
Gunasekera B., et al., "Intracortical Recording Interfaces: Current Challenges to Chronic Recording Function," ACS Chemical Neuroscience, 16 pages (2015).
Harreither W., et al., "Carbon Nanotube Fiber Microelectrodes Show a Higher Resistance to Dopamine Fouling," Analytical Chemistry, vol. 85, pp. 7447-7453 (2013).
Harris A.R., et al., "Measuring the effective area and charge density of platinum electrodes for bionic devices," J. Neural Eng., vol. 15, pp. 046015-1-046015-13 (2018).
Hassler C., et al., "Characterization of parylene C as an encapsulation material for implanted neural prostheses," J. Bio. Mat. Res. B Appl. Biomat., vol. 93B, Issue No. 1, pp. 267-274 (2010).
Irwini Z.T., et al., "Chronic recording of hand prosthesis control signals via a regenerative peripheral nerve interface in a rhesus macaque," J. Neural Eng., vol. 13, pp. 046007-1-046007-11 (2016).
Jalili R., et al., "Formation and processability of liquid crystalline dispersions of graphene oxide," Mater. Horiz., vol. 1, pp. 87-91 (2014).
Jalili R., et al., "Scalable one-step wet-spinning of graphene fibers and yarns from liquid crystalline dispersions of graphene oxide: towards multifunctional textiles," Univ. of Wollongong Australia, 31 pages (2013).
Jiang K., et al., "Superaligned Carbon Nanotube Arrays, Films, and Yarns: A Road to Applications," Adv. Materi., vol. 23, pp. 1154-1161 (2011).
Keefer E.W., et al., "Carbon nanotube coating improves neuronal recordings," Nature, vol. 3, pp. 434-439 (2008).
Kim D., et al., "Conducting polymers on hydrogel-coated neural electrode provide sensitive neural recordings in auditory cortex," Acta Biomaterialia, vol. 6, pp. 57-62 (2010).
Kim Y., et al., "Electrochemical detection of dopamine in the presence of ascorbic acid using graphene modified electrodes," Biosensors and Bioelectronics, vol. 25, pp. 2366-2369 (2010).
Kim Y., et al., "Material considerations for peripheral nerve interfacing," MRS Bulletin, vol. 37, pp. 573-580 (Jun. 2012).
Kou L., et al., "A Mini Review on Nanocarbon-Based 1D Macroscopic Fibers: Assembly Strategies and Mechanical Properties," Nano-Micro. Lett., vol. 9, Issue No. 51, 18 pages (2017).
Kozai T.D., et al., "Chronic In Vivo Evaluation of PEDOT/CNT for Stable Neural Recordings," IEEE Trans. Bio. Eng., vol. 63, Issue No. 1, pp. 111-119 (Jan. 2016).
Kozai T.D.Y., et al., "Chronic tissue response to carboxymethyl cellulose based dissolvable insertion needle for ultra-small neural probes," Biomaterials, pp. 1-14 (2014).
Kozai T.D.Y., et al., "Ultrasmall implantable composite microelectrodes with bioactive surfaces for chronic neural interfaces," Nature Materials, vol. 11, pp. 1065-1073 (Nov. 2012).
Lacour S.P., et al., "Flexible and stretchable micro-electrodes for in vitro and in vivo neural interfaces," Med. Biol. Comput., vol. 48, pp. 945-954 (2010).
Lee Y., et al., "Strategies for Minimizing Glial Response to Chronically-implanted Microelectrode Arrays for Neural Interface," Biomed. Eng. Lett., vol. 4, pp. 120-128 (2014).
Li D., et al., "Processable aqueous dispersions of graphene nanosheets," Nature Nantechnology, vol. 3, pp. 181-185 (Feb. 2008).
Lissandrello, C.A., et al., "A Micro-scale printable nanoclip for electrical stimulation and recording in small nerves", J. Neural Eng., vol. 14, published Mar. 21, 2017 (12 pages).
Liu T., et al., "Implantable Graphene-based Neural Electrode Interfaces for Electrophysiology and Neurochemistry in In Vivo Hyperacute Stroke Model," Applied Materials and Interfaces, pp. 187-196 with supporting information (2015).
Lu Y., et al., "Electrodeposited polypyrrole/carbon nanotubes composite films electrodes for neural interfaces," Biomaterials, vol. 31, pp. 5169-5181 (2010).
Lu Y., et al., "Flexible Neural Electrode Array Based-on Porous Graphene for Cortical Microstimulation and Sensing," Scientific Reports, 9 pages (Sep. 2016).
Luo X., et al., "Highly stable carbon nanotube doped poly(3,4-ethylenedioxythiophene) for chronic neural stimulation," Biomaterials, vol. 32, pp. 5551-5557 (2011).
Mccallum G.A., et al., "Chronic interfacing with the autonomic nervous system using carbon nanotube (CNT) yarn electrodes," Scientific Reports, vol. 7, pp. 11723-1-11723-14 (Sep. 2017).
Extended European Search Report for Application No. 19928380.5, dated Nov. 29, 2022, 7 pages.
Amend, B., et al., "How Does Sacral Modulation Work Best? Placement and Programming Techniques to Maximize Efficacy," Current Urology Reports, 2011, 12: pp. 327-335.
Dupont, G., et al., "The Nerve to Levator Ani." 2021, Elsevier. pp. 25-28.

(56) References Cited

OTHER PUBLICATIONS

Fowler, C.J., et al., "The neural control of micturition." Nature Reviews Neuroscience, 2008. 9(6): pp. 453-466.
Grigorescu, B., et al., "Innervation of the levator ani muscles: description of the nerve branches to the pubococcygeus, iliococcygeus, and puborectalis muscles," International Urogynecology Journal 19, pp. 107-116 (2008).
Groen, J., et al., "Chronic Pudendal Nerve Neuromodulation in Women with Idiopathic Refractory Detrusor Overactivity Incontinence: Results of a Pilot Study With a Novel Minimally Invasive Implantable Mini-Stimulator." Neurourology and Urodynamics, 2005. 24(3): pp. 226-230.
Hokanson, J.A., et al., "Stimulation of the Sensory Pudendal Nerve Increases Bladder Capacity in the Rat." Am J Physiol Renal Physiol, 2018. 314(4): pp. F543-F550.
International Search Report and Written Opinion for International Application No. PCT/US2022/049744, mailed Apr. 13, 2023, 13 pages.
International Search Report and Written Opinion for International Application No. PCT/US2023/028425, mailed Dec. 13, 2023, 20 pages.
International Search Report and Written Opinion for International Application No. PCT/US2023/028426, mailed Dec. 13, 2023, 18 pages.
Madill, S.J., et al., "Relationship Between Abdominal and Pelvic Floor Muscle Activation and Intravaginal Pressure During Pelvic Floor Muscle Contractions in Healthy Continent Women." Neurology and Urodynamics, 2006. 25(7): pp. 722-730.
Manzo, J., et al., "The role of pubococcygeus muscle in urinary continence in the male rat." The Journal of Urology, 1997, 157(6): pp. 2402-2406.
Markland, A.D., et al., "Prevalence and Trends of Urinary Incontinence in Adults in the United States, 2001 to 2008." The Journal of Urology, 2011. 186(2): pp. 589-593.
Messelink, E.J., "The overactive bladder and the role of the pelvic floor muscles." BJU International, 1999. 83 Suppl 2: pp. 31-35.
Shafik, A., et al., "Overactive bladder inhibition in response to pelvic floor muscle exercises." World Journal of Urology, 2003. 20(6): pp. 374-377.
Silva, M.E.T., et al., "Establishing the biomechanical properties of the pelvic soft tissues through an inverse finite element analysis using magnetic resonance imaging." Proc Inst Mech Eng H, 2016. 230(4): pp. 298-309.
Tyagi, P., et al., "Pathophysiology and animal modeling of underactive bladder." International Urology and Nephrology, 2014. 46 Suppl 1: pp. S11-S21.
Jaqua, K., et al., "Where Are We Headed with Neuromodulation for Overactive Bladder?" Current Urology Reports, 2017. 18(8): pp. 59.
Kavvadias, T., et al., "Management of device-related complications after sacral neuromodulation for lower urinary tract disorders in women: a single center experience." Arch Gynecol Obstet, 2017. 295(4): pp. 951-957.
Lazarou, G., et al., "Anatomic variations of the pelvic floor nerves adjacent to the sacrospinous ligament: a female cadaver study." International Urogynecology Journal, 2008. 19(5): pp. 649-654.
Loukas, M., et al., "Topography and Landmarks for the Nerve Supply to the Levator Ani and its Relevance to Pelvic Floor Pathologies." Clinical Anatomy, 2016. 29(4): pp. 516-523.
Nishizawa, O., et al., "Role of the pudendal nerves on the dynamics of micturition in the dog evaluated by pressure flow EMG and pressure flow plot studies." J Urol, 1984. 132(5): pp. 1036-1039 (Abstract Only).
Peters, K.M., et al., "Sacral Versus Pudendal Nerve Stimulation for Voiding Dysfunction: A Prospective, Single-Blinded, Randomized, Crossover Trial." Neurourology and Urodynamics, 2005. 24(7): pp. 643-647.
Pierce, L.M., et al., Distribution and immunohistochemical characterization of primary afferent neurons innervating the levator ani muscle of the female squirrel monkey. American Journal of Obstetrics and Gynecology, 2006. 195(4): pp. 987-996.
Siegel, S., et al., "Three-year Follow-up Results of a Prospective, Multicenter Study in Overactive Bladder Subjects Treated With Sacral Neuromodulation." Urology, 2016. 94: pp. 57-63. (Objective, Methods, and Results Only).
Yamashiro, J., et al., "New Implantable Tibial Nerve Stimulation Devices: Review of Published Clinical Results in Comparison to Established Neuromodulation Devices." Research and Reports in Urology, 2019. vol. 11: pp. 351-357.

\* cited by examiner

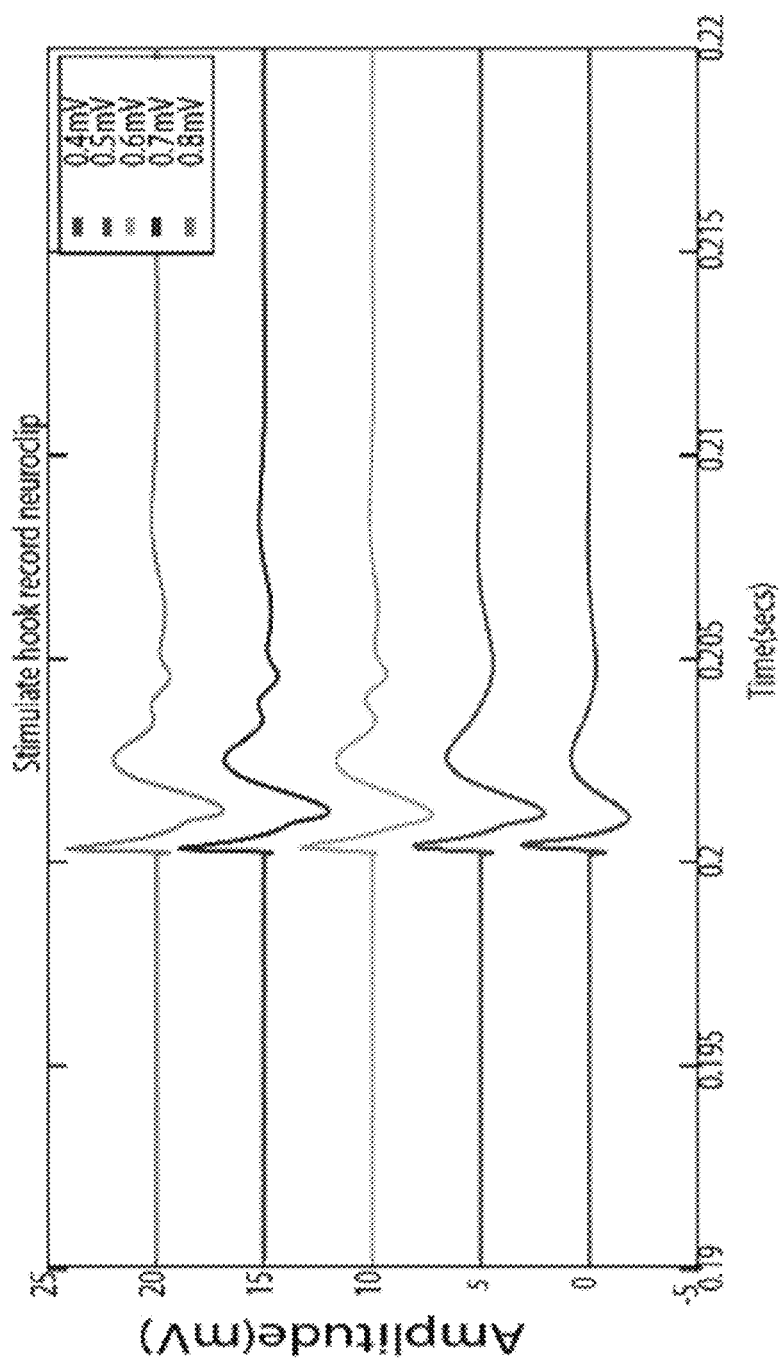

stimulating electrode record EMG

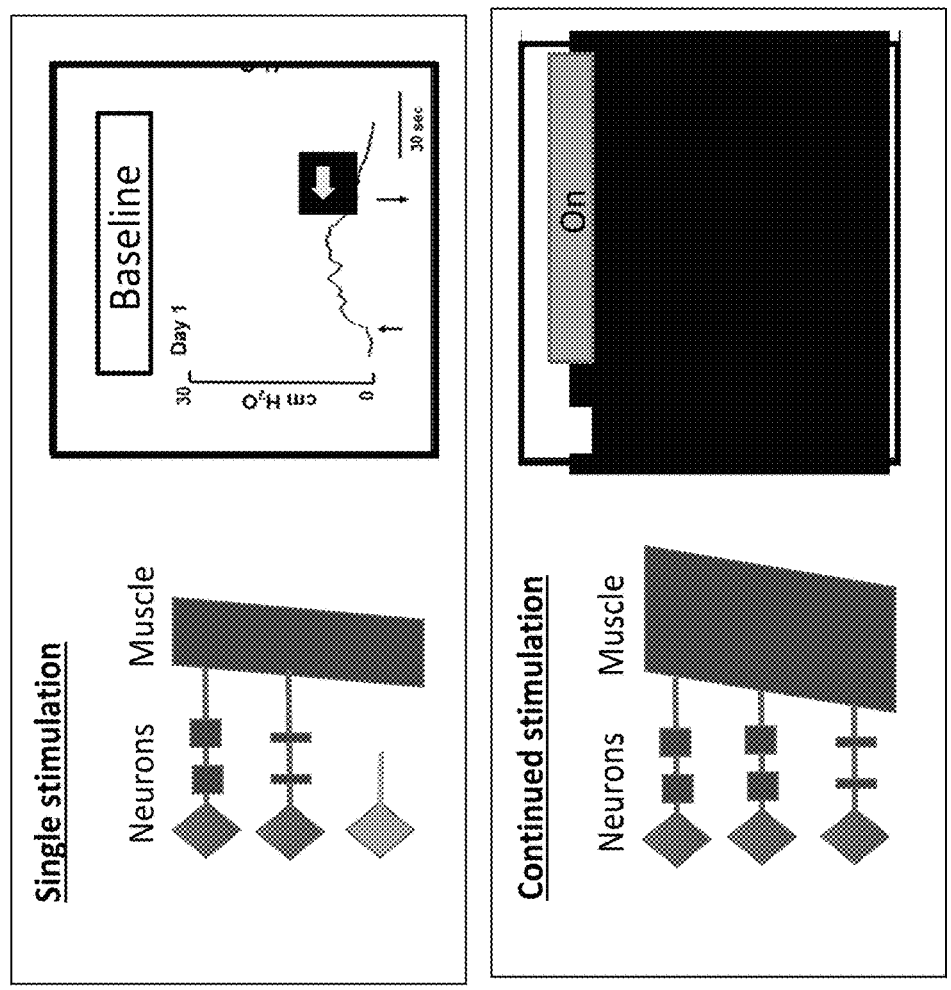
Figure 18 C
Figure 18 D
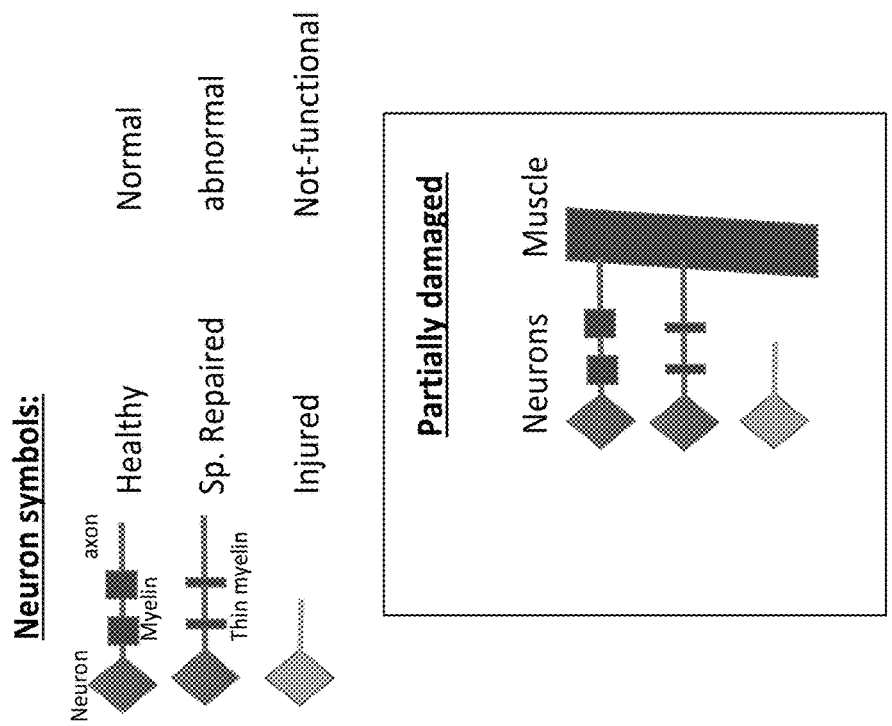
Figure 18 A
Figure 18 B

DEVICES AND METHODS FOR NEUROMODULATION

CROSS REFERENCE TO RELATED APPLICATIONS

This application is a continuation-in-part application of U.S. Non-Provisional application Ser. No. 16/185,285, filed on Nov. 9, 2018, which claims priority pursuant to 35 U.S.C 119(e) to U.S. Provisional Patent Application No. 62/584,195, filed on Nov. 10, 2017, and U.S. Provisional Patent Application No. 62/584,203, filed on Nov. 10, 2017, each of which is hereby incorporated by reference in its entirety.

GOVERNMENTAL SPONSORSHIP

This invention was made with government support under Grant No. R01 DK120307 awarded by the National Institutes of Health. The government has certain rights in the invention.

TECHNICAL FIELD

This disclosure is related to devices and methods for neuromodulation of the pelvic system.

BACKGROUND

Silicone nerve cuff electrodes are used extensively in a broad range of clinical applications including stimulation of the vagus nerve for the treatment of epilepsy, depression and tinnitus, sacral or pudendal nerves for lower urinary tract disorders, and tibial nerve for rehabilitation of patients with drop foot.

Nerve targets for these applications consist of somatic and autonomic nerves, of which somatic nerves are large, robust and easy to interface. However, therapeutic neural stimulation for targeted regulation of visceral organ function requires miniature implantable electrode devices which interface with autonomic nerves with minimal to no effect on the inherent nerve anatomy. Autonomic and somatic nerves near to their target organs have small diameter, usually less than 200 μm and are very fragile, making them difficult to handle and increasing the risk of damage when implanting a traditional cuff electrode.

Conventional electrode implantation and securing methods involve suturing and/or use of medical grade epoxy. Securing cuff electrodes to small and fragile nerve often causes damage due to excessive manipulation. This is exacerbated in nerves that are located near to blood vessels or adjacent to internal organ targets. Thus, there is a need for improved neuromodulation devices that minimize nerve manipulation and properly anchor electrodes to small nerves and nerve fibers.

Dysfunctional pelvic floor muscles can manifest as various impediments to normal bodily functions, including, but not limited to micturition, defecation, erection, and orgasm. Currently, urinary incontinence affects more than 200 million people worldwide, pelvic floor dystonia is often seen in the clinical setting of overactive bladder, and weak or damaged pelvic floor muscles contribute to the development of stress urinary incontinence.

Pelvic floor muscle training (PFMT) has become a widely accepted first choice of treatment for stress urinary incontinence. PFMT can generate improvement rates of 50-70%. Despite the improvements, inability to move damage muscles, inaccurate performance and low patient compliance (dropout rate of 39%) drastically limits this approach.

Transvaginal electrical stimulation and pelvic floor muscle training are commonly used for both female stress urinary incontinence and overactive bladder symptoms and appear to be effective at various levels of electrical stimulation, but offer variable degrees of stimulation due to the volume conductance stimulation method used. The mechanism of neuromodulation has been postulated to mediate the reflex inhibition of detrusor contraction by the activation of afferent fibers within the pudendal nerve. However, intravaginal and anal plug electrodes are intolerable for some patients due to pain, discomfort or mucosal injury. Moreover, selective stimulation of targeted muscles and nerves is not possible using current technologies and non-selective neuromodulation can lead to unwanted side effects. Thus, improved methods of neuromodulating perineal muscles are needed.

SUMMARY

In one aspect, a neuromodulation device is described herein, which in some embodiments, provides one or more advantages over current neuromodulation devices. For example, a device described herein, in some cases, can comprise a unique L-shaped longitudinal channel that allows access to the recording/stimulating chamber. This design offers a slide-in-lock mechanism using a slit opening calculated to be 5-50% of the nerve diameter, through which a nerve can be inserted via a soft and brief stretching of the nerve tissue, and then released or relaxed or "unstretched" inside an electrode chamber. The design facilitates facile and rapid implantation of the neuromodulation device while minimizing nerve manipulation to prevent nerve damage during implantation.

In some embodiments, a neuromodulation device described herein comprises (i) a chamber operable to receive a nerve, (ii) at least one electrode disposed in the chamber, and (iii) a channel defined by two walls. In some embodiments, the channel is in fluid communication with an interior of the chamber and an external surface of the device. In some instances, the channel comprises an average width that is 5-50% smaller than an average diameter of the chamber. In some instances, the interior chamber is 5-10% larger than the nerve. In other cases the channel is non-linear.

In another aspect methods of treating and/or preventing pelvic dysfunctions are disclosed herein. Methods disclosed herein can provide one or more advantages over current methods of preventing and/or treating pelvic floor dysfunction. For example, methods described herein can be more effective in neuromodulating specific individual pelvic floor muscles, unlike current methods, which are non-specific and can lead to unwanted side effects caused by stimulation of sacral roots or the pudendal nerve. In some embodiments a method comprises neuromodulating one or more pelvic floor muscles. For example, a step of neuromodulating can be achieved using any device described herein.

In some embodiments a method includes engaging a nerve within a neuromodulation device, and selectively stimulating at least a portion of the engaged nerve by sending electrical signals from the at least one electrode. The neuromodulation device may include an implantable unit having a chamber, at least one electrode disposed in the chamber, and a channel defined by two walls, wherein the chamber has a width less than the nerve such that the nerve is briefly and reversibly stretched when the nerve is engaged with the neuromodulation device, and either an internal or external unit coupled to the neuromodulation unit, the internal or external unit configured to control the operation of the implantable unit.

In such a method, engaging the nerve within the neuromodulation device may include briefly stretching at least a portion of the nerve so as to reduce the average diameter of the stretched portion of the nerve, and sliding the stretched portion of the nerve through the channel into the chamber where it is relaxed.

In such a method the average diameter of the stretched portion of the nerve is between about 5% to 50% smaller than the average diameter of the nerve in an unstretched portion of the nerve.

Additionally, selectively stimulating at least a portion of the engaged nerve may include applying stimulation to at least one of the pelvic floor muscles including the ilioccoccygeus, pubococcygeus, coccygeus, puborectalis, bulbospongiosus, ischiocavernosus nerves, or their trunk nerves as they branch of the pudendal and levator ani nerves The applied stimulation of the nerve may contract one or more pelvic floor muscles or pelvic organs. The applied stimulation may include the human equivalent of applying a dose of electrical stimulation in rabbits, wherein a dose comprises applying a current between 20 microAmps to 10 milliAmps or a voltage that induce similar current or ion flow, and nerve depolarization. Further, the applied stimulation may include the human equivalent of applying a dose of electrical stimulation in rabbits, wherein a dose comprises applying a frequency of between about 2 Hz to 50 KHz.

In some embodiments, a method for treating a human patient having a pelvic floor disorder includes engaging a neuromodulation device with a nerve configured to innervate one or more muscles of the pelvic floor, wherein the neuromodulation device is configured to stimulate nerves, and applying a stimulation from the neuromodulation device to the nerve configured to innervate one or more muscles of the pelvic floor. Pelvic floor disorder may include at least one of urinary incontinence, overactive bladder, fecal incontinence, pelvic floor dysfunction, rectal prolapse, defecatory disorders, pelvic organ prolapse and sexual dysfunction. Application of the stimulation causes at least one of the iliococcygeus, pubococcygeus, coccygeus, puborectalis, bulbospongiosus, and ischiocavernosus muscles to contract or release. The applied stimulation may include the human equivalent of applying a dose of electrical stimulation in rabbits, wherein a dose comprises applying a current between 20 microAmps to 10 milliAmps at a frequency of between about 2 Hz to 50 KHz. The nerve configured to innervate one or more muscles of the pelvic floor comprises at least one of the iliococcygeus, pubococcygeus, coccygeus, puborectalis, bulbospongiosus, and ischiocavernosus nerves, or their trunk nerves as they branch of the pudendal and levator ani nerves In some embodiments, a method to repair a nerve in a human patient to treat a pelvic floor disorder, may include the steps of engaging a neuromodulation device to the nerve configured to innervate a pelvic floor muscle, and applying a pulsed stimulation to the nerve for a period of time. Pelvic floor disorders may include at least one of urinary incontinence, overactive bladder, fecal incontinence, pelvic floor dysfunction, rectal prolapse, defecatory disorders, pelvic organ prolapse and sexual dysfunction. The neve configured to innervate the pelvic floor muscle comprises at least one of the iliococcygeus, pubococcygeus, coccygeus, puborectalis, bulbospongiosus, and ischiocavernosus nerves, or their trunk nerves as they branch of the pudendal and levator ani nerves. Application of the sustained stimulation causes at least one of the iliococcygeus, pubococcygeus, coccygeus, puborectalis, bulbospongiosus, and ischiocavernosus muscles to contract or release. Further, sustained stimulation includes a human equivalent of applying 10 minutes of stimulation at 2 Hz and 10 milliAmps, 3 times a week for at least a two week period in rabbits. Additionally, sustained stimulation includes the human equivalent of applying a dose of electrical stimulation in rabbits, wherein a dose comprises applying a current between 20 microAmps to 100 milliAmps at a frequency of between about 10 Hz to 50 KHz, wherein a plurality of doses are applied for at least a two week period. The sustained stimulation repairs or regenerates damaged axons in the nerve and strengths the muscles that they innervate.

In some embodiments, a neuromodulation device includes an implantable unit and an external unit. The implantable unit includes a chamber configured to receive a nerve, a channel in fluid communication with the chamber, wherein a first end of the channel is in fluid communication with an external surface of the implantable unit and a second end of the channel is in fluid connection with the chamber, at least one electrode disposed within a surface of the chamber. An external or internal unit may be coupled to the implantable unit, and configured to control the operation of the implantable unit.

In such an embodiment, at least one electrode may be configured to at least one of apply a stimulation to the nerve, and/or record electrical activity of the nerve. The channel of the neuromodulation device may include an average width that is 5-50% smaller than an average diameter of the nerve in an unstretched state, while the interior chamber can be 90-110% the size of the nerve diameter. In case of the 90% chamber size, the nerve will deform and be accommodated in the L-channel. The channel of the neuromodulation device may be non-linear. The external unit of the neuromodulation device may include a power-data transmission antenna configured to transmit data and power to the implantable unit and receive data from the implantable unit, a power source, a radio-frequency amplifier, and telemetry electronics. The at least one electrode may be configured to apply stimulation to at least one of the at least one of the iliococcygeus, pubococcygeus, coccygeus, puborectalis, bulbospongiosus, and ischiocavernosus nerves, or their trunk nerves as they branch of the pudendal and levator ani nerves. The applied stimulation of the nerve contracts one or more pelvic floor muscles. The applied stimulation comprises the human equivalent of applying a dose of electrical stimulation in rabbits, wherein a dose comprises applying a current between 20 microAmps to 10 milliAmps at a frequency of between about 2 Hz to 50 KHz. The external unit may be coupled to the implantable unit by way of magnetic inductive coupling.

In some embodiments, a method includes engaging a nerve within a neuromodulation device, and selectively stimulating at least a portion of the engaged nerve by sending electrical signals from the at least one electrode. The neuromodulation device may include an implantable unit having a chamber, at least one electrode disposed in the chamber, and a channel defined by two walls, wherein the chamber has a width less than the nerve such that the nerve is reversibly stretched when the nerve is engaged with the neuromodulation device, and an external unit coupled to the implantable unit, the external unit configured to control the operation of the implantable unit. Engaging the nerve within the neuromodulation device may include stretching at least a portion of the nerve so as to reduce the average diameter of the stretched portion of the nerve to about 5% to 50% smaller than the average diameter of the nerve in an unstretched portion of the nerve, and sliding the stretched portion of the nerve through the channel into the chamber. Selectively stimulating at least a portion of the engaged nerve may include applying stimulation to at least one of the at least one of the iliococcygeus, pubococcygeus, coccygeus, puborectalis, bulbospongiosus, and ischiocavernosus nerves, or their trunk nerves as they branch of the pudendal and levator ani nerves. The applied stimulation of the nerve contracts one or more pelvic floor muscles. The applied stimulation may include the human equivalent of applying a dose of electrical stimulation in rabbits, wherein a dose includes applying a current between 20 microAmps to 10 milliAmps at a frequency of between about 2 Hz to 50 KHz.

In some embodiments, a method may include engaging a nerve within a neuromodulation device, and selectively recording one or more electrical signals transmitted along at least a portion of the engaged nerve by the at least one electrode. The neuromodulation device may include an implantable unit having a chamber, at least one electrode disposed in the chamber, and a channel defined by two walls, wherein the chamber has a width less than the nerve such that the nerve is reversibly stretched when the nerve is engaged with the neuromodulation device, and an external unit coupled to the implantable unit, the external unit configured to control the operation of the implantable unit.

In some embodiments a method may include the steps of providing an implantable neuromodulation device having a chamber configured to apply an electrical stimulation, engaging a target nerve with the implantable neuromodulation device by compressing at least a portion of the target nerve in a channel of the implantable neuromodulation device, and sliding the target nerve into a chamber of the neuromodulation device fluidly connected to the channel where the target nerve is decompressed, and applying an electrical stimulation to the target nerve via one or more electrodes positioned within the chamber of the neuromodulation device thereby initiating a response from a pelvic floor muscle innervated by the target nerve.

In such an embodiment, the target nerve may include one of the Levator Ani Nerve, Pubococcygeus Nerve, Coccygeus Nerve, Puborectalis Nerve, Pudendal Nerve, Bulbospongiosus Nerve, Ischiocavernosus Nerve, Clitoral Nerve and Dorsal Nerve of the penis. The response from the pelvic floor muscle may be a contraction or relaxation. The applied electrical stimulation may include the human equivalent of applying an electrical stimulation at a frequency between about 0.5-100 Hz in rabbits. The applied electrical stimulation may include the human equivalent of applying an electrical stimulation having an amplitude between about 0.5-20 mAmps in rabbits. The applied electrical stimulation may include the human equivalent of applying an electrical stimulation having a voltage between about 0.1-1 V in rabbits. The applied electrical stimulation has one of a square monopolar, cathodic, or bipolar balanced shape. The applied electrical stimulation may include an electrical pulse having a duration of between about 0.1-10 ms. Compressing at least a portion of the target nerve may include stretching at least a portion of the target nerve so as to reduce the average diameter of the stretched portion of the target nerve. Optionally, the average diameter of the stretched portion of the target nerve is between about 5% to 50% smaller than the average diameter of the target nerve in an unstretched portion of the target nerve.

In some embodiments, a method to repair a nerve in a human patient to treat a pelvic floor disorder, may include the steps of providing an implantable neuromodulation device having a chamber configured to apply an electrical stimulation, engaging a target nerve with the implantable neuromodulation device by compressing at least a portion of the target nerve in a channel of the implantable neuromodulation device, and sliding the target nerve into a chamber of the neuromodulation device fluidly connected to the channel where the target nerve is decompressed, and applying a sustained electrical stimulation to the target nerve via one or more electrodes positioned within the chamber of the neuromodulation device thereby initiating a repair process in the target nerve.

Pelvic floor disorders may include at least one of urinary incontinence, overactive bladder, fecal incontinence, pelvic floor dysfunction, rectal prolapse, defecatory disorders, pelvic organ prolapse and sexual dysfunction.

The target nerve may include one of the Levator Ani Nerve, Pubococcygeus Nerve, Coccygeus Nerve, Puborectalis Nerve, Pudendal Nerve, Bulbospongiosus Nerve, Ischiocavernosus Nerve, Clitoral Nerve and Dorsal Nerve of the penis. The sustained electrical stimulation may include the human equivalent of applying an electrical stimulation at a frequency between about 1-100 Hz in rabbits. The sustained electrical stimulation may include the human equivalent of applying an electrical stimulation having an amplitude between about 0.5 to 20 mAmps in rabbits. The sustained electrical stimulation may include the human equivalent of applying an electrical stimulation having a voltage between about 0.5 to 30 mV in rabbits. The sustained electrical stimulation may include the human equivalent of applying an electrical stimulation having a pulse duration between about 0.2 and 10 ms.

Embodiments may include a method for blocking activity in a target nerve, including the steps of providing an implantable neuromodulation device having a chamber configured to apply an electrical stimulation, engaging a target nerve with the implantable neuromodulation device by compressing at least a portion of the target nerve in a channel of the implantable neuromodulation device, and sliding the target nerve into a chamber of the neuromodulation device fluidly connected to the channel where the target nerve is decompressed, and applying a high frequency electrical stimulation having a frequency between about 1 to 1000 KHz to the target nerve via one or more electrodes positioned within the chamber of the neuromodulation device thereby blocking electrical activity in the target nerve.

The high frequency electrical stimulation may have an amplitude between about 0.5 to 20 mAmps. Optionally, the high frequency electrical stimulation has a voltage of between 0.1-7V.

These and other embodiments are described in greater detail in the following detailed description.

BRIEF DESCRIPTION OF THE DRAWINGS

FIG. 1A illustrates design and fabrication of the neuroclip electrode according to one embodiment described herein. Figure may not be to scale.

FIG. 2 illustrates the "slide-in-lock" mechanism of the neuroclip according to one embodiment described herein.

FIG. 3B illustrates a SU-8 neuroclip device with gold electrode, according to one embodiment described herein.

FIG. 7A is a schematic of a stimulating hook electrode and recording neuromodulation device.

FIG. 7B is a line graph of recording capabilities of a neuromodulation device, as described herein, when the nerve was stimulated proximally using a hook electrode.

FIG. 18A provides a schematic representation of neurons for an experiment built in accordance with embodiments of the present disclosure.

FIG. 18B provides a schematic representation for neurons in a first state in connection with an experiment built in accordance with embodiments of the present disclosure.

FIG. 18C provides schematic representation of neurons and experimental results for an experiment built in accordance with embodiments of the present disclosure.

FIG. 18D provides schematic representation of neurons and experimental results for an experiment built in accordance with embodiments of the present disclosure.

DETAILED DESCRIPTION

Figure 1A:
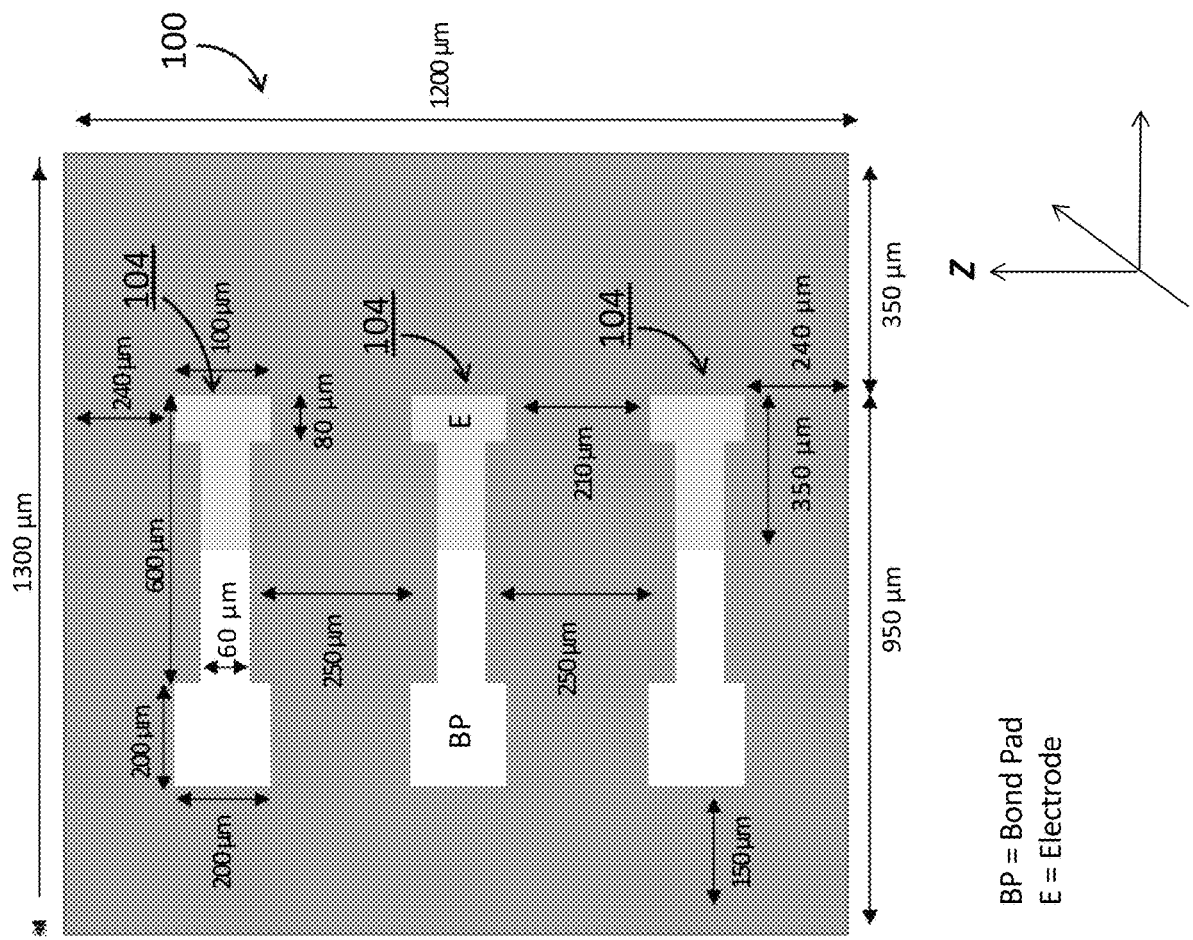
FIG. 1A is a top view of a schematic representation of a neuromodulation device described herein.
Figure 1B:
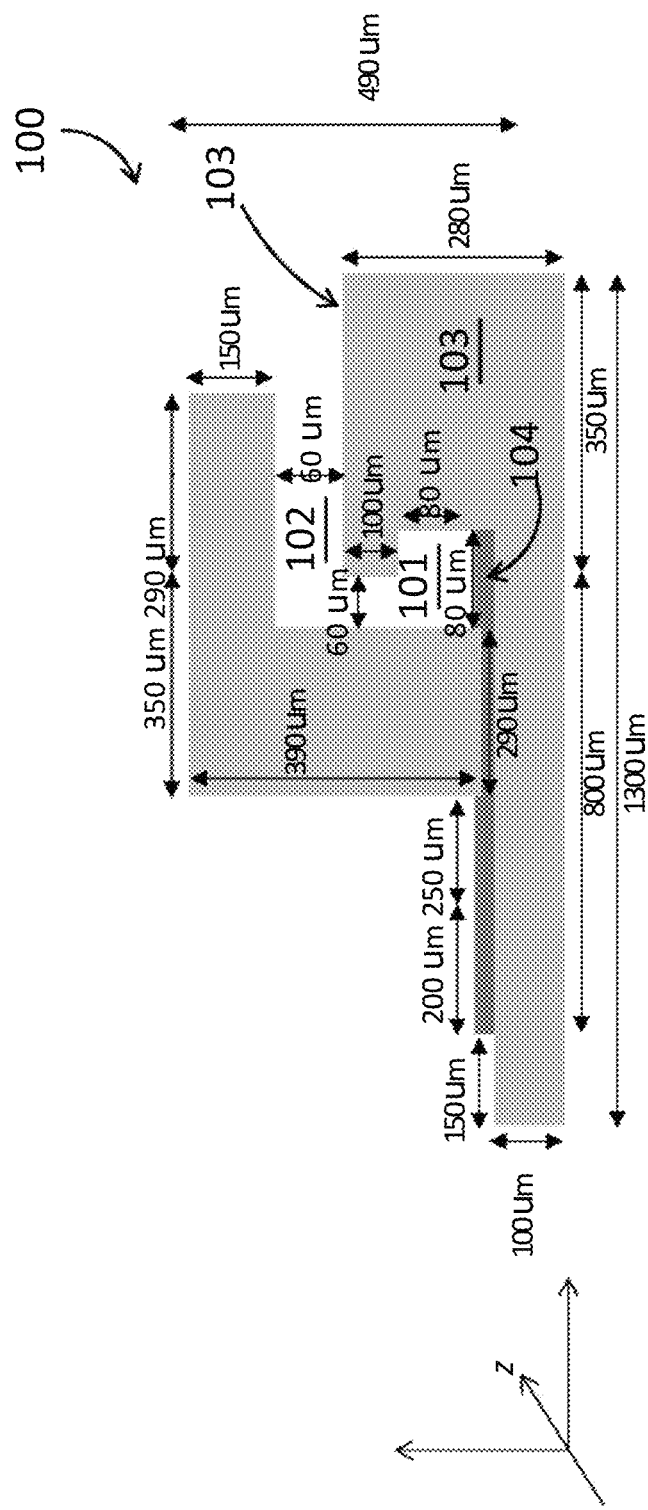
FIG. 1B is a profile view of the schematic representation of a neuromodulation device shown in FIG. 1A. The perspective is indicated by the axes. Figure may not be to scale.
Figure 1C:
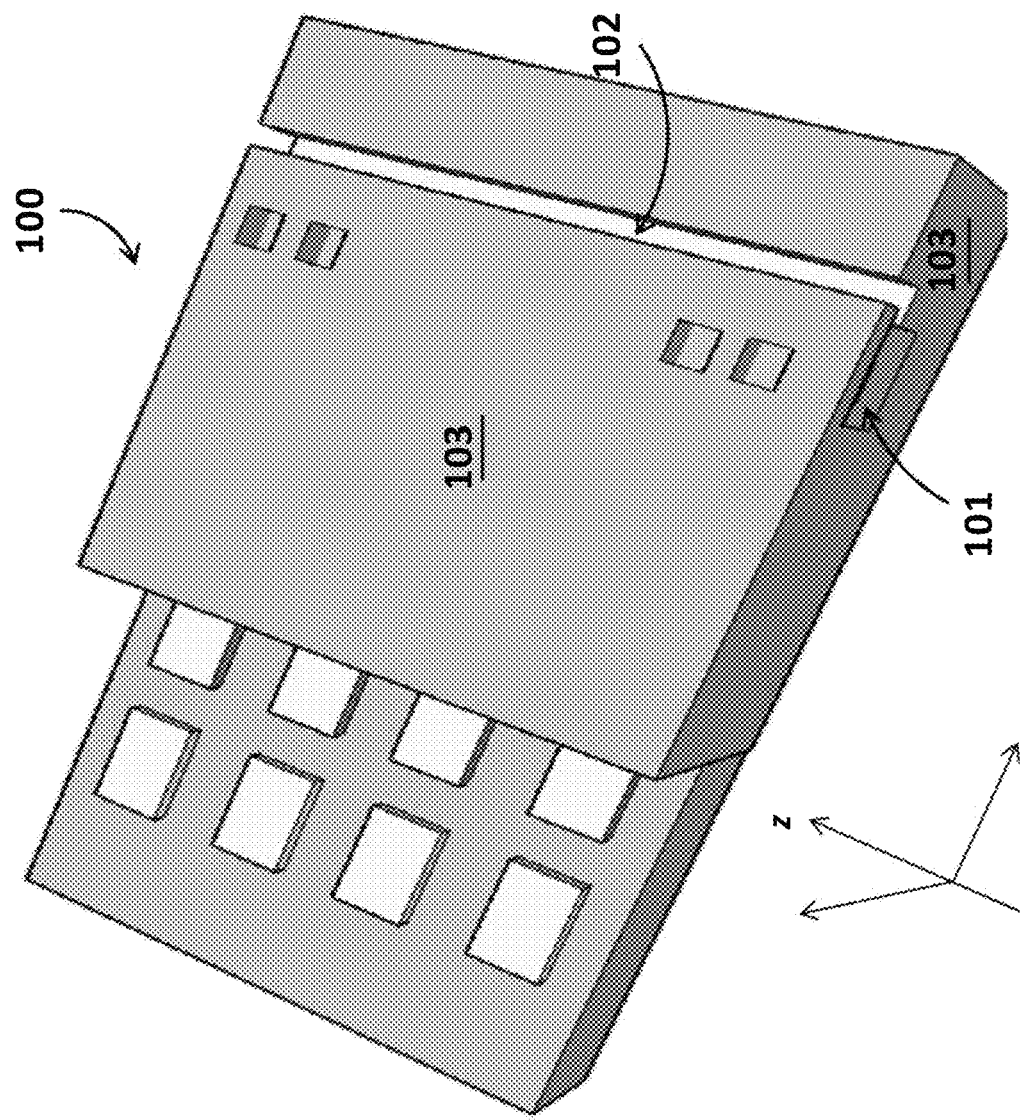
FIG. 1C is a top perspective view diagram of a neuromodulation device described herein.

Embodiments described herein can be understood more readily by reference to the following detailed description and examples. Methods, devices, and features described herein, however, are not limited to the specific embodiments presented in the detailed description and examples. It should be recognized that these embodiments are merely illustrative of the principles of the present disclosure. Numerous modifications and adaptations will be readily apparent to those of skill in the art without departing from the spirit and scope of the disclosure.

In addition, all ranges disclosed herein are to be understood to encompass any and all subranges subsumed therein. For example, a stated range of "1.0 to 10.0" should be considered to include any and all subranges beginning with a minimum value of 1.0 and ending with a maximum value of 10.0 or less, e.g. 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the endpoints 5 and 10.

Further, when the phrase "up to" is used in connection with an amount or quantity, it is to be understood that the amount is at least a detectable amount or quantity. For example a material present in an amount "up to" a specified amount can be present from a detectable amount and up to and including the specified amount.

Neuromodulation Devices

FIGS. 1A-4 illustrate various embodiments of a neuromodulation device. In one aspect a neuromodulation device 100 is described herein, which in some embodiments, comprises a chamber 101 operable to receive a nerve 200, at least one electrode 104 disposed in the chamber 101, and a channel 102 defined by two walls. In some embodiments, a channel 102 can be in fluid communication with an interior of the chamber 101 and an external surface 103 of the device 100. In some instances, a channel 102 can be in fluid communication with more than one external surface 103 of the device 100. In some embodiments, the channel 102 comprises an average width that is 5-50% smaller than an average diameter of the chamber 101. In some instances, the channel 102 can be non-linear.

Devices described herein can be formed from a polymer. For example, in some embodiments, a neuromodulation device can be fabricated using flexible polyimide/SiC substrates with gold metallization in ultra-micro scale using established thin-film and photolithography methods. In some embodiments, a device can be made of SU-8 or other such polymer, using commonly employed microfabrication methods and photoresist techniques.

In some embodiments, a device described herein can be conductive. For example, a device can be connected to an electrical pulse generator and/or an electrical stimulator. The device, in some cases, can comprise transmission circuitry. For example, transmission circuitry of a device can facilitate magnetic inductive coupling.

Now turning to specific components of a device 100, in some embodiments, a chamber 101 can be a recording chamber 101 and/or a stimulating chamber 101. For example, a recording chamber 101 can record electrical activity within the chamber 101 and a stimulating chamber 101 can elicit an electrical stimulus within the chamber 101.

In some embodiments, a chamber 101 is operable to receive a nerve 200. In some embodiments described herein, a nerve 200 is also a target nerve 200. A nerve 200, as described herein, can include a single nerve axon, multiple nerve axons, a nerve fiber, a nerve bundle, a nerve fascicle, or other similar neuroanatomical structure. It should be understood, that a nerve 200, as described herein, should be a functionally intact nerve or a partially-functional nerve. For example, a functionally intact nerve should comprise a functional pre- and post-synaptic terminal and should be functionally capable of propagating an action potential. A nerve, in some embodiments, can have an average diameter of at least 50 μm, at least 100 μm, at least 200 μm, at least 300 μm, at least 400 μm, at least 500 μm, at least 600 μm, at least 700 μm, at least 800 μm, or at least 900 μm. In some embodiments, a nerve can have an average diameter between about 50 μm and 4 mm or between about 50 μm and 800 μm.

A chamber 101, in some embodiments, can be cylindrical in shape, as in a pipe, wherein the ends of a cylindrically shaped chamber 101 are open to allow longitudinal exit of a nerve 200 from the chamber 101 toward the pre- and post-synaptic terminals of the nerve 200. Whereas a cylinder comprises a circular shape, it should be understood that a chamber 101 can also comprise a triangular, square, pentagonal, hexagonal, or polygonal shape having n number of sides, while maintaining a general 3-dimensional structure resembling a cylinder, or a pipe, having open ends and operable to receive a nerve 200.

A chamber 101, in some embodiments, can be in fluid communication with a first external surface 103 and a second external surface 103 of a device 100, wherein the first and second external surfaces 103 are on opposite sides of the device 100 and the chamber 101, positioned between the first and second external surfaces is in fluid communication with each opposing first and second external surfaces 103 of the device 100.

A chamber 101, in some embodiments, comprises a length, width, and depth, wherein the length of the chamber 101 corresponds to a z-axis that traverses longitudinally along a nerve 200 extending through the device 100. In some embodiments, a chamber 101 can have an average length of at least 10 μm. In some embodiments, a chamber 101 can have an average length of at least 50 μm, at least 100 μm, at least 500 μm, or at least 1000 μm. In some embodiments, a chamber 101 can have an average length of between about 10 μm and 10 mm. In some embodiments, a chamber 101 can have an average length of between about 10 μm and 5 mm, between about 10 μm and 3 mm, between about 10 μm and 1 mm, or between about 10 μm and 1 mm.

The width and depth of a chamber 101, in some embodiments, correspond to cross-sectional dimensions of an x-y-plane orthogonal to the z-axis of the chamber 101. For example, a cylindrically shaped chamber 101 can have a width and depth corresponding to a diameter of the chamber 101. The diameter of a non-cylindrically shaped chamber 101 can be measured by averaging the distance of measurements intersecting the center point of a cross-section of the chamber 101, wherein the center point is positioned on the z-axis extending through the middle of the chamber 101. In some embodiments, a chamber 101 can have an average diameter of about less than 10 mm. In some embodiments, a chamber 101 has an average diameter of about 0.5 μm to about 5000 μm, about 0.5 μm to about 4000 μm, 0.5 μm to about 3000 μm, about 0.5 μm to 2000 μm, about 0.5 μm to 1000 μm, about 0.5 μm to 900 μm, or about 0.5 to 800 μm, or about 0.5 μm to 500 μm.

In some embodiments, a chamber 101 has an average diameter that is substantially the same or 10% smaller than the average diameter of a target nerve 200. In some embodiments, the average diameter of the chamber 101 is no more than 5% larger or no more than 5% smaller than the average diameter of the target nerve 200. In some embodiments, the average diameter of the chamber 101 is no more than 15% larger or no more than 15% smaller than the average diameter of the target nerve 200. For example, for a target nerve 200 having an average diameter of about 80 μm, a device 100 can have an average diameter of no less than about 56 μm, and no more than 104 μm. In some embodiments, a chamber 101 has an average diameter that is about 80-120% of a target nerve 200, about 85-115% of a target nerve 200, about 90-110% of a target nerve 200, about 95-105% of a target nerve 200, or about 100% or equal in size of a target nerve 200.

In some embodiments, a device 100 described herein comprises a channel 102 defined by two walls. The two walls can provide an upper boundary and lower boundary of a channel described herein. In some instances, a distal end of a channel 102 can be in fluid communication with an interior of a chamber 101 and a proximal end of a channel 102 can be in fluid communication with an exterior surface 103 of a device 100. Thus, a distal end of a channel 102 is open to a chamber 101. In some embodiments, the chamber 101 is indefinitely or constantly open to the channel 102, such that the distal opening of the channel 102 into the chamber 101 does not close. Moreover, a channel 102 can connect the interior of a chamber to an external surface 103 of a device 100 described herein. Thus, the chamber 101 is essentially in constant communication with an exterior surface 103 of the device via the channel 102. For example, the chamber 101 remains open to the channel at all times and the channel 102 remains open to an exterior surface at all times.

A channel 102, in some embodiments, comprises a length, a depth, and a diameter, which are not interchangeable. Similar to the length of a chamber 101 described above, a length of a channel 102 corresponds to a measurement along a z-axis, which traverses longitudinally along a nerve 200. A length can be measured at any point along a channel 102 between the distal end of channel opening into a chamber 101 and the proximal end of a channel opening to an exterior surface 103 of the device. In some embodiments, a distal end of a channel 102 can be in fluid communication with a chamber 101 for an entire length of the chamber 101. In some cases, the average length of a channel 102 is substantially the same as the average length of a chamber 101 of a device 100 described herein.

In some embodiments, a channel 102 can have an average length of at least 10 μm. In some embodiments, a channel 102 can have an average length of at least 50 μm, at least 100 μm, at least 500 μm, or at least 1000 μm. In some embodiments, a channel 102 can have an average length of between about 10 μm and 10 mm. In some embodiments, a channel 102 can have an average length of between about 10 μm and 5 mm, between about 10 μm and 3 mm, between about 10 μm and 1 mm, or between about 10 μm and 1 mm.

The depth of a channel 102 corresponds to a distance measured between the distal opening and the proximal opening of the channel 102, wherein the distance is measured along an imaginary centerline positioned equidistant between each channel wall. In some cases, a depth can be a linear measurement. For example, in some cases, the channel 102 is a linear channel 102. In other cases, a channel 102 can be non-linear, wherein a non-linear channel comprises one or more turns, curves, or bends in the channel walls. Thus, in some instances, the depth of a non-linear channel 102 can be measured by measuring the distance along the imaginary centerline of a channel 102 between the distal opening and proximal opening of the channel 102, and along each bend in the non-linear channel 102. For example, in some embodiments, a channel 102 can comprise an "L" shape, such that the channel 102 depth measurement comprises a 90-degree turn and each end of the "L" corresponds to the distal and proximal openings of the channel. In an exemplary channel having a 90-degree turn, the depth can be measured by summing the distance of an imaginary centerline of the channel for each arm in the "L" of the channel 102 extending between the proximal opening and the distal opening of the channel 102 to where the imaginary lines of each arm meet. The shape of the channels can also include other configurations such as T, Z and S, and others.

In some embodiments, a channel 102 can have an average depth of between about 50 μm and 10 mm. In some embodiments a channel 102 can have an average depth of between about 50 μm and 5 mm, between about 50 μm and 1 mm, between about 50 μm and 900 μm, between about 50 μm and 800 μm, between about 50 μm and 700 μm, between about 50 μm and 600 μm, between about 50 μm and 500 μm, between about 50 μm and 400 μm, between about 50 μm and 300 μm, between about 50 μm and 200 μm, or between about 50 μm and 100 μm.

The diameter of a channel 102 corresponds to a measurement of the channel 102 positioned in an x-y plane that is orthogonal to the z-axis, as described above. A diameter of a channel 102 can be a constant, such that the diameter of a channel 102 does not change between the proximal opening and distal opening of the channel 102. That is, in some embodiments, a diameter of a channel 102 comprises less than 10% variability of an average diameter across an entire depth of a channel 102. In some cases, a channel 102 comprises less than 5% variability, less than 3% variability, or less than 2% variability of an average diameter along an entire depth measurement of a channel 102. In some cases, a diameter can be determined by measuring the shortest distance between the two walls of a channel 102.

A diameter of a channel 102, in some embodiments, is less than a diameter of a target nerve 200. For example, in some embodiments, a channel 102 diameter can be at least 5% smaller than a diameter of a target nerve 200. In some embodiments, a channel 102 diameter can be at least 5%, at least 10%, at least 15%, at least 20%, at least 25%, at least 30%, at least 35%, at least 40%, at least 45%, or at least 50% smaller than a diameter of a nerve 200. In some embodiments, a channel 102 diameter can be no more than 60% smaller than a target nerve 200 diameter. In other embodiments, a channel 102 diameter can be no more than 50% smaller than a target nerve 200 diameter. In some embodiments, a channel 102 diameter can be between about 5% and 60% smaller than a diameter of a target nerve 200. In some cases, a channel 102 diameter can be between about 10% and 50%, between about 10% and 40%, between about 15% and 40%, between about 20% and 35%, or between about 20% and 40% smaller than a diameter of a target nerve 200.

Furthermore, similar to a chamber 101 described hereinabove, a channel 102 described herein can have open ends in fluid communication with the open ends of the chamber 101 such that a nerve 200 can be inserted into a chamber 101 by sliding, moving, or inserting a longitudinal section of a nerve 200 into a chamber 101 via a channel 102. Thus, in some instances, a channel 102 described herein is operable to receive a nerve 200, including a target nerve 200. Moreover, in some embodiments, a channel 102 can be in fluid communication with at least three external surfaces 103 of the device 100. For example, a channel 102 can be open to an interior of a chamber 101 at a distal end of the channel and the channel can extend along a depth of the channel to a third external surface 103 at a proximal end of the channel, while maintaining fluid communication with a first external surface 103 and a second external surface 103 on opposing sides of the device 100 corresponding to opposing ends of the z-axis.

In some embodiments, a device described herein comprises at least one electrode 104 disposed within a chamber 101 of the device. An electrode 104 can include various types of electrodes, including fiber or flat electrodes, thin film electrodes or needle electrodes. A thin film electrode disposed in the chamber can have a recording or stimulating surface within 100-2000 μm$^2$ or within 50 μm of an outer surface of a nerve 200 disposed in the chamber 101. A needle electrode disposed in the chamber can have a needle shaped recording and/or stimulating surface that can penetrate a surface of a nerve 200 disposed in the chamber 101. An electrode that penetrates a nerve disposed in the chamber 101 can stimulate and/or record intraneurally, which can provide greater selectivity and/or resolution when recording and/or stimulating. Additionally, an electrode 104 can be positioned on any surface within the chamber 101, including a top, a bottom, or side surface of the chamber.

In some embodiments, a plurality of electrodes can be disposed within a chamber. Wherein more than one electrode is present in the chamber, a combination of electrode types can be used. For example, both flat electrodes and/or needle electrodes can be used in a recording and/or stimulating chamber 101. A device described herein can comprise mono-polar, bi-polar, tri-polar, or a multi-electrode array electrodes. In some cases, a plurality of electrodes can be configured in a tripolar configuration. Such a tripolar configuration can provide improved nerve specificity and/or selectivity while simultaneously reducing extraneous biological noise.

In some embodiments, an electrode can be made from one or more conductive metals. For example, in some instances, an electrode comprises gold, titanium nitride (TiN), iridium oxide (IrO), iridium, carbon nanotubes, graphene, graphene oxide, and/or platinum (Pt). An electrode, in some instances, can have a charge injection capacity of about 0.1 mC/cm$^2$ or greater. Further, in some embodiments, an electrode described herein can be a wired or a wireless electrode. A wireless electrode can comprise a wireless integrated circuit within the device 100.

In some embodiments, an electrode can comprise a stimulating and/or recording surface area of between about 25 μm$^2$ and 25 mm$^2$. In some instances, an electrode comprises a stimulating and/or recording surface area of between about 100 μm$^2$ and 1 mm$^2$ or between about 100 μm$^2$ and 0.5 mm$^2$.

Methods of Neuromodulation

In another aspect, methods of treating and/or preventing pelvic dysfunction are disclosed herein, which in some embodiments, comprises neuromodulating one or more pelvic floor muscles. Some exemplary pelvic floor muscles include the cremaster muscle, bulboglandularis muscle (Bgm), ischiocavernosus muscle (Ism), bulbospongiosus muscle (Bsm), pubococcygeus muscle (Pcm), iliococcygeus muscle (Icm), coccygeus muscle (Cgm), or puborectalis muscle (Prm). In some embodiments, a pelvic floor muscle can be neuromodulated or stimulated simultaneously or independently of one or more other pelvic floor muscles. In some cases, neuromodulating one or more pelvic muscles comprises modulating one or more pelvic nerves. In some instances, a pelvic nerve can include any nerve, nerve bundle, nerve fascicle, or nerve tract that innervates a pelvic floor muscle. For example, in some cases, the nerve can be a cremaster nerve, bulboglandularis nerve, ischiocavernosus nerve, bulbospongiosus nerve, pubococcygeus nerve, iliococcygeus nerve, coccygeus nerve, or puborectalis nerve, or their trunk nerves as they branch of the pudendal and levator ani nerves. By neuromodulating one or more nerves innervating one or more pelvic floor muscles, methods described herein provide greater specificity, efficacy, and resolution of pelvic floor muscle stimulation.

It should be understood than any device described hereinabove in Section I can be used in methods described herein. For example, the device 100 described hereinabove, comprises a chamber operable to receive a nerve, such as a nerve innervating a pelvic floor muscle. In some cases, multiple devices 100 can be used to perform a method described herein. For example, two or more devices 100 can be used to stimulate two or more pelvic floor muscles. Furthermore, since a device 100 described hereinabove can record and/or stimulate, two devices can be used on the same pelvic floor muscle to independently record and stimulate, or one device can be used to record and stimulate the pelvic floor muscle.

Now turning to specific steps of a method, in some embodiments, a method described herein can comprise disposing a first nerve in a first device, the first device 100 comprising a chamber, at least one electrode disposed in the chamber, and a channel defined by two walls, and selectively stimulating the first nerve by sending electrical signals from an electrode of the first device to the first nerve.

In some embodiments, a method further comprises disposing a second nerve in a second device, the second device comprising a chamber, at least one electrode disposed in the chamber, and a channel defined by two walls, and selectively stimulating the second nerve by sending electrical signals from an electrode of the second device to the second nerve, wherein the first nerve is a bulbospongiosus nerve and the second nerve is a pubococcygeus nerve.

Selectively stimulating, as described herein, can mean stimulating a specific target nerve, and only the specific target nerve, such as a motor neuron that innervates a muscle. For example, non-selective stimulation can result in non-selective muscle stimulation, wherein multiple muscles are simultaneously stimulated from a single electrical signal sent from an electrode to a nerve. For example, stimulation of a sacral nerve root, while being a single nerve can, stimulate multiple muscles from a single electrical signal sent from an electrode to the nerve. In contrast, selectively stimulating results in finer resolution wherein only one muscle is stimulated from an electrical signal sent from an electrode.

In some embodiments, a method can comprise disposing or implanting any device 100 described hereinabove in Section I into a subject. In some instances, the subject can be in need of pelvic floor muscle simulation. Implanting a device can be achieved by disposing or positioning a target nerve 200 within a chamber 101 of the device 100 and stimulating the nerve 200 disposed within the chamber. A target nerve 200 can include any section of a functionally intact nerve 200, as described hereinabove in Section I. In some embodiments, a target nerve innervates a pelvic floor muscle. For example, the bulbospongiosus nerve (Bsn) and/or the pubococcygeus nerve (Pcn) can be target nerves 200 of a method described herein.

In some embodiments, implanting a device 100 can comprise longitudinally stretching a section of a nerve 200 and transversely sliding the stretched nerve through the channel into a chamber. Stretching a nerve 200 can comprises stretching the nerve 200 for less than 30 seconds or less than 10 seconds to reduce the average diameter of the stretched section of the nerve 200. In some cases, the stretched nerve can have an average diameter that is 5% to 50% smaller than the average diameter of the same nerve at an unstretched section. In some cases, the stretched nerve can have an average diameter that is 5% to 40%, 5% to 35%, 5% to 30%, 5% to 25%, 5% to 20%, 5% to 15%, or 5% to 10% smaller than the average diameter of the same nerve at an unstretched section.

In some cases, a method further comprises positioning an electrode into a recording and/or stimulating position. For example, in some cases, positioning an electrode comprises piercing, puncturing, or penetrating the surface of the nerve with the electrode, such that the electrode is in an intraneural recording position and/or an intraneural stimulating position. In some cases, positioning an electrode comprises positioning an electrode within 100 μm or within 50 μm of the external surface of a nerve 200. For example a thin film electrode can be positioned within 100 µm or within 50 µm of the external surface of a nerve 200.

In some embodiments, a method described herein comprises electrically stimulating one or more pelvic muscle nerves. For example, electrical stimulation can be provided via one or more devices 100 described herein. In some cases, electrical stimulation can be provided in pulses. An electrical stimulation pulse, in some embodiments, can be between about 1 microsecond and 1 second in duration. In some embodiments, an electrical stimulation pulse can be between about 1 µs and 500 millisecond (msec), between about 1 µs and 100 msec, between about 1 µs and 50 msec, between about 1 µs and 40 sec, between about 1 µs and 30 msec, between about 10 µs and 20 msec, or between about 100 µs and 5 msec.

Additionally, in some embodiments, electrical stimulation can be provided in a dose comprising multiple pulses, wherein each electrical stimulation pulse is provided after a period of rest or a period of no electrical stimulation. In some cases, the period of rest or no stimulation in between each electrical stimulation pulse can be a constant time duration. In other cases, the period of rest or no stimulation in between each electrical stimulation pulse can vary in time duration, such that the rate of electrical stimulation pulse can be constant, increase, or decrease over time in a single dose. For example, in some embodiments, electrical stimulation pulses can be provided at a rate of about 1 to 200 pulses per second, about 1 to 100 pulses per second, about 1 to 50 pulses per second, or about 1 to 20 pulses per second.

In some embodiments, electrical stimulation can be provided to a nerve at a frequency of between about 1 Hz and 50 KHz. In some embodiments an electrical stimulation can be provided to a nerve at a frequency of between about 1 Hz and 40 KHz, between about 1 Hz and 30 KHz, or between about 1 Hz and 20 KHz.

In some embodiments, an electrical stimulation pulse provides a current to the target nerve of between about 1 µAmp and 5 Amp. In some embodiments an electrical stimulation pulse provides a current to the target nerve of between about 1 µAmp and 3 Amp, between about 1 µAmp and 2 Amp, or between about 1 µAmp and 1000 milliAmp.

In some instances a dose of electrical stimulation can have a defined time duration. For example, in some embodiments, a dose can be between about 1 second and 10 minutes. A dose, in some embodiments, can be between about 10 seconds and 10 minutes, between about 10 seconds and 1 minute, or between about 10 seconds and 30 seconds. In some embodiments, multiple doses can be provided over the course of a treatment or prevention paradigm. For example, one or more doses can be provided on a daily, weekly, or monthly schedule.

Figure 15:
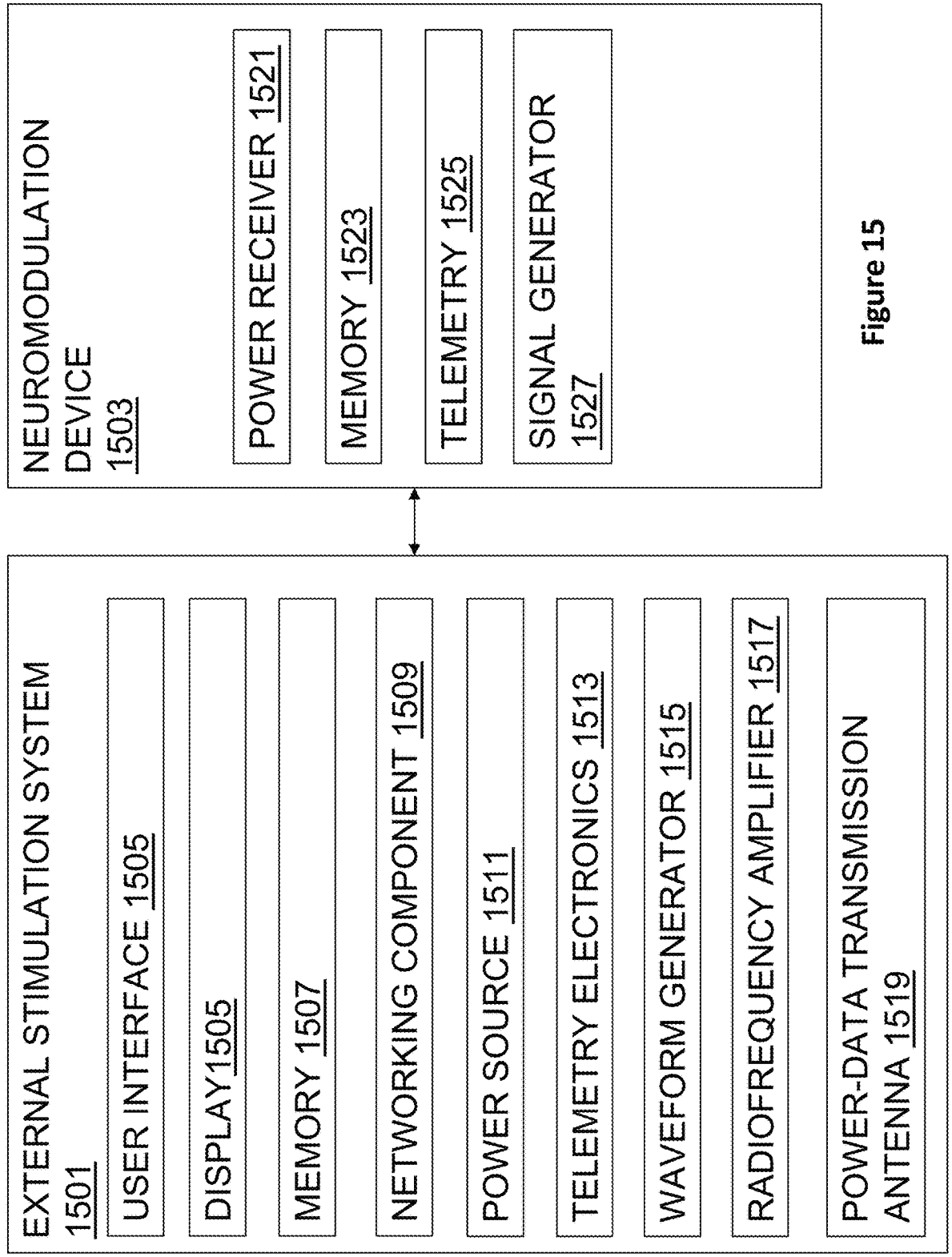
FIG. 15 is a schematic diagram for a system in accordance with embodiments of the present disclosure.

As illustrated in FIG. 15, in some embodiments, a neuromodulation device such as neuromodulation device 100 or 1503 may be coupled to an external stimulation system 1501. In some embodiments, the neuromodulation device 1503 is coupled to an internal or external stimulation system 1501 by way of a wired or wireless connection. In some embodiments, the neuromodulation device may be wired or battery-powered and/or configured to receive electrical power from the external stimulation system. In some embodiments, stimulation and/or recording by the neuromodulation device 100, 1503 may be controlled by operation of the external stimulation system 1501 configured to be located outside of a patient's body.

In some embodiments, the neuromodulation device 1503 may include a power receiver 1521, memory 1523, telemetry 1525, signal generator 1527 and the like.

In some embodiments, the external stimulation system 1501 may include a power source 1511, telemetry electronics 1513, a waveform generator 1515, a radiofrequency amplifier 1517, a power-data transmission antenna 1519 and the like. Embodiments, may also include a user interface 1505, display 1505, memory 1507, and networking component 1509.

In some embodiments, a waveform generator 1515 may be configured to have a 1-10 GHz carrier frequency. In some cases, a pulse generator (e.g., Agilent® 81110A Pulse Pattern Generator) may be connected to a waveform generator with a 10.0 MHz carrier frequency at 200 mV peak-to-peak (e.g., Agilent® 33250A Function/Arbitrary Waveform Generator).

In some embodiments, a power source 1511 may be coupled to a power-transmission antenna 1519 (e.g., AG 1012 series amplifier T&C Power Conversion, Inc.). The power-transmission antenna 1519 may include a radiofrequency amplifier and transmission antenna and be further configured to magnetically power the neuromodulation device. In some embodiments the telemetry electronics 1513 may include application-specific integrated circuit(s).

In some embodiments, the power-data transmission antenna 1519 may be configured to power and control the neuromodulation device 1503 via magnetic fields ranging from 2 to 200 A m-1 and power levels ranging from 10-2000 mV. Further, the external power-data transmission is configured to allow the external stimulation system 1501 to communicate with the internal neuromodulation device 1503 over a 4-40 cm distance. According, the external stimulation system 1501 may be positioned at a 0-60 degree angle from the receiving device. In some embodiments, the antenna 1519 may be configured to receive and transmit signals over air, wet environments, blood, tissue, muscle, bodily fluids, fat, and the like.

In some embodiments, the neuromodulation device 1503 may be configured to deliver a current in the range of 5-2000 µAmps to a target nerve. The pulse applied by the neuromodulation device 1503 may have a square, trapezoidal, monophasic, biphasic or other shape. In some embodiments, the pulse may be monophasic with a positive or negative charge. In some embodiments, the pulse may be monophasic with a positive or negative voltage.

Embodiments in accordance with the present disclosure may include the following discussed methods and related apparatus.

Accordingly, embodiments include a method for treating a human patient including positioning a neuromodulation device about a nerve configured to innervate one or more muscles of the pelvic floor, and applying a stimulation from the neuromodulation device to the nerve configured to innervate one or more muscles of the pelvic floor. The neuromodulation device may be configured to stimulate and/or record from the one or more nerves it is engaged with.

In some embodiments, a method may be configured to stimulate at least one nerve in a mammalian patient to treat at least one pelvic floor disorder. The method may include positioning a neuromodulation device in the patient such that a nerve is engaged with the neuromodulation device, wherein the neuromodulation device is coupled to a electrostimulation apparatus outside of the patient, and applying an electoral stimulation signal with the neuromodulation device to the target nerve so as to contract one or more muscles affiliated with the pelvic floor.

In some embodiments, a method may be configured to repair a nerve in a human patient to treat at least one pelvic floor disorder. The method may include positioning a neuromodulation device in the patient such that a nerve is engaged with the neuromodulation device, wherein the neuromodulation device is coupled to a electrostimulation apparatus outside of the patient, and applying an electoral stimulation signal with the neuromodulation device to the target nerve so as to repair a nerve configured to innervate one or more muscles affiliated with the pelvic floor.

In some embodiments, a method for stimulating a nerve may accelerate on initiate a regeneration or repair process in a related treatment area.

As discussed above, in some embodiments an individual stimulation pulse may be in the range of 20-500 microseconds. Further, individual stimulation pulses may be applied at a frequency of 2-30 Hz for slow twitch and 40-80 Hz for fast twitch with a duration of 40 secs, and an amplitude of 2-200 micro Amps. Individual pulses can be rectangular monophasic or bi-phasic, with the duration of each phase being in the 2-2000 microseconds in duration. The application of stimulation pulses of 200 microseconds at 2-7 Hz and 40 micro Amps to a somatic nerve may be sufficient to observe muscle contractions from one or more limb muscles innervated by the somatic nerve in the rabbit. Further, non-observable muscle activation in the limb muscles may take place via the application of stimulation pulses at lower current amplitudes to the somatic nerve. For each muscle, observable muscle contraction may be the result of stimulation above a stimulation threshold (T) for the observable muscle, and non-observable muscle activation may be defined as sub-threshold (sT).

Observable muscle contraction, by stimulation above the stimulation threshold T may be achieved by the application of stimulation continuously or in pulse-rest patterns. For example, in some embodiments, observable muscle contractions may be stimulated by the application of pulse-rest patterns including 30-300 seconds of stimulation followed by a 15-150 second period of rest. In some embodiments, the pulse-rest patterns may be uniform or variable.

The application of stimulation to a nerve by a neuromodulation device such as neuromodulation device 100 in order to stimulate a nerve so as to cause observable muscle contraction may be used to treat, mitigate, reverse, or repair pelvic disorders and their related biological systems. Examples of pelvic disorders include altered pleasure and sexuality, urinary and fecal continence, and pelvic organs prolapse. Pelvic disorders may be the result of abnormal relaxation or contraction of the pelvic floor muscles, which in turn may be due to partial damage by trauma or age. Nerves innervating the pelvic floor muscles include (but are not limited to) the following: perineal nerve or branches of the pudendal nerve innervating the scrotum or labia majora skin, the bulbospongiosus and ischiocavernosus nerves, and the levator ani nerve and its branches forming the iliococcygeal, pubococcygeal, puborectal, and coccygeal nerves, or the pubovaginalis, puboperinealis and puboanalis nerves. One or more of the nerves innervating the pelvic or perineal muscles may form a sling around the urogenital hiatus and rectum thereby forming a sphincter. Accordingly, activation of the pelvic or perineal muscles may promote their closure.

Pelvic disorders may be due to one or more of the pelvic or perineal nerves being partially demyelinated which in turn compromises their function. In some embodiments, systems and methods may be configured to repair demyelinated perineal nerves by applying an electrical stimulation having a frequency of 10-100 Hz, with pulses of 2-200 microseconds and amplitudes of 20-200 microAmps. In some embodiments, the disclosed electrical stimulation is capable of inducing remyelination and regeneration of injured nerves.

In some embodiments the neuromodulation device may be implanted adjacent to one or more pelvic or perineal nerves, at the sacral S1-S5 rami, the trunk of large nerves such as the pudendal or the levator ani, or at the distal individual nerve fascicles attached to single pelvic or perineal muscles.

In some embodiments, the activation of motor axons in pelvic and perineal nerves due to stimulation by the neruomodulation device may activate, recruit, and/or repair damaged axons, reform neuromuscular connections, and/or repair and strengthen the pelvic muscles innervated by the pelvic and perineal nerves.

The stimulation of pelvic nerves may be used to strengthen the pelvic floor muscles and reverses symptoms associated with stress urinary incontinence and other pelvic disorders.

In some embodiments multiple neuromodulation devices may be implanted and the coordinated activation of which may aid in treatment of pelvic disorders. Accordingly, the selective and/or coordinated activation of a single or plurality of pelvic and perineal nerves can be achieved.

In some embodiments, the neuromodulation device may be used to apply a stimulation to a target nerve so as to depolarize the axons in the nerve antidromically and/or orthodromically. The orthodromic depolarization of motor efferent axons in a target nerve may directly activate the pelvic muscles innervated by the target nerve. The antidromic depolarization of autonomic and sensory axons in a target nerve may contribute to the afferent control of micturition by activating upstream neurons in peripheral ganglia, spinal cord, brainstem, brain, and the like.

In some embodiments, a neuromodulation device such as neuromodulation device 100 may be used to stimulate the pelvic nerves. For example, the pelvic nerve may be stimulated at a frequency of between 2-50 Hz in order to cause slow muscle twitches. Further, if stimulation is applied at a 50-100 Hz fast muscle twitch activation may be achieved.

In some embodiments, in order to treat a pelvic disorder, stimulation may be applied by a neuromodulation device such as neuromodulation device 100 to a pelvic nerves. In such an embodiment, stimulation may include bursts of pulsed electrical energy for 2-20 min a day, with 1-3 applications a day and 3-7 days a week. In some embodiments, the stimulation of the pelvic nerves may be performed daily for at least 15 days to induce nerve regeneration, remyelination, muscle repair and strengthen the pelvic floor muscles. Stimulation may be applied to the pelvic and perineal nerves including periods of activation and rest periods within a single stimulation session. Further, a treatment plan may include several activation sessions per week and/or several weeks with rest periods. For example, a 5-15 minute rest period may be used between stimulations in a single session, and several days of rest may be used between days including stimulation in order to allow the corresponding muscle to recover and avoid fatigue. Muscle strengthening may be achieved by the repair of those muscle fibers which atrophy as a result of de-myelination or injury to the nerves. Nerve stimulation of the pelvic nerves mediated regeneration, re-myelination that in turn re-establishes the communication with the nerve, allowing it to recover and strengthen. Although pulse, dosage, frequency, and currents required for the effective stimulation of rabbit pelvic floor muscles are discussed herein, one skilled in the art would recognize the human equivalents thereof may be used for the treatment of pelvic floor disorders and the like. Optimal pulses, dosage, frequency, and currents for effective use of a neuromodulation device such as neuromodulation device 100 in humans may be determined by an effective closure of the urethral and/or anal sphincters formed by the pelvic floor muscles. This effect can also be evaluated by an increase in sexual function. The stimulation parameters obtained in animal models may scale to human nerves according to differences in nerve diameter, and the thickness of the perineurium and epineurium layers. It is envisioned that nerves in the humans are approximately 5-20 times larger than those in rabbits, and accordingly will require 5-20 times as much electrical stimulation. For example, nerves in humans require approximately 10 times as much electrical stimulation as do nerves in rodents.

As will be discussed herein, in some embodiments, the neuromodulation device may be coupled to an external unit including an electrical stimulator. Optionally, the neuromodulation device may be wirelessly connected to the external unit. In some embodiments, the two modules may be ultrasonically coupled via an ultrasonic activation by way of a piezoelectric receiver located on the neuromodulation device. Alternatively, the external unit may be coupled to the implanted neuromodulation device by way of a Bluetooth link, magnetic induction, thermal/infrared induction and/or an optical link. Alternative methods are envisioned.

Embodiments of the neuromodulation device disclosed herein may be positioned accordingly to treat pelvic floor disorders, sexual dysfunction, and the like. In particular, the neuromodulation device may be positioned to engage with one or more of the following nerves (and their associated muscles): Levator Ani Nerve, Pubococcygeus Nerve, Coccygeus Nerve, Puborectalis Nerve, Pudendal Nerve, Bulbospongiosus, Ischiocavernosus, Clitoral Nerve and Dorsal Nerve of the penis.

Many modifications and other embodiments of the subject matter will come to mind to one skilled in the art to which the subject matter pertains having the benefits of the teachings presented in the foregoing descriptions and the associated drawings. For example, although specific configurations of neuromodulation devices are described above and depicted in the figures, numerous other neuromodulation devices configured to modulate a nerve may benefit from embodiments of the present subject matter. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Various implementations of devices and methods have been described, and exemplary embodiments are described below in fulfillment of various objectives of the present disclosure. It should be recognized that these implementations are merely illustrative of the principles of the present disclosure. Numerous modifications and adaptations thereof will be readily apparent to those skilled in the art without departing from the spirit and scope of the present disclosure. For example, individual steps of methods described herein can be carried out in any manner not inconsistent with the objectives of the present disclosure, and various configurations or adaptations of devices described herein may be used.

Example 1

Design of a Device for Neuromodulation

The present example illustrates the design and fabrication of an exemplary device 100, sometimes referred to as a "Neuroclip", according to one or more embodiments disclosed herein. The exemplary device can be implanted onto small caliber nerves and nerve fibers. The multi electrodes 104 grouped in tripolar configuration can provide specificity and selectivity.

The disclosed approach is drastically different than prior approaches in that a device 100 described herein uses a slide-n-lock mechanism to place and secure the electrode 104 of the device 100 onto the nerve 200. The electrode has an L-shaped slit through which the target nerves slide and lock into a recording/stimulating compartment or chamber 101.

The slide-in-lock mechanism is unique and particularly beneficial for inserting the electrode onto small nerves with minimal handling and reducing the risk of nerve damage.

A slit opening of proximal channel 102 can be on either the top or to the side of the device 100. The channel is calculated to be about 25-50% smaller than the nerve diameter through which a nerve 200 can be inserted via a soft and brief stretching of the nerve tissue, and then release inside an electrode chamber 101.

This device 100 provides a self-securing mechanism of the nerve without damaging it, as well as reducing the time and effort required for implantation (see FIG. 1). As shown in FIG. 1A-1B, a device 100 can have tripolar (3) gold electrode contact pads or 8 gold electrode pads. Furthermore, a device 100 can have a channel that interfaces with a top-side of the device 100, such that the device 100 comprises a top-insertion mechanism for a nerve 200. As shown in FIG. 1C, an actual device 100 prototype was fabricated using an SU-8 photoresist and having a tripolar electrode with a side-insertion channel. The device's 100 impedance at 1 kKz was around 500 KOhms across two gold electrodes. Such exemplary devices 100 provide improved safety and reliable of a neuromodulation device 100 that can be customized to targeted nerve 200 anatomy.

Extensive clinical studies of stress and strain on peripheral nerves resulted in an accepted values of 20-32% elongation to avoid structural and mechanical damage. It has also been shown that effects on electrical conductivity at a transient 5-10% strain could be recovered immediately with no apparent functional deficits.

Figure 2:
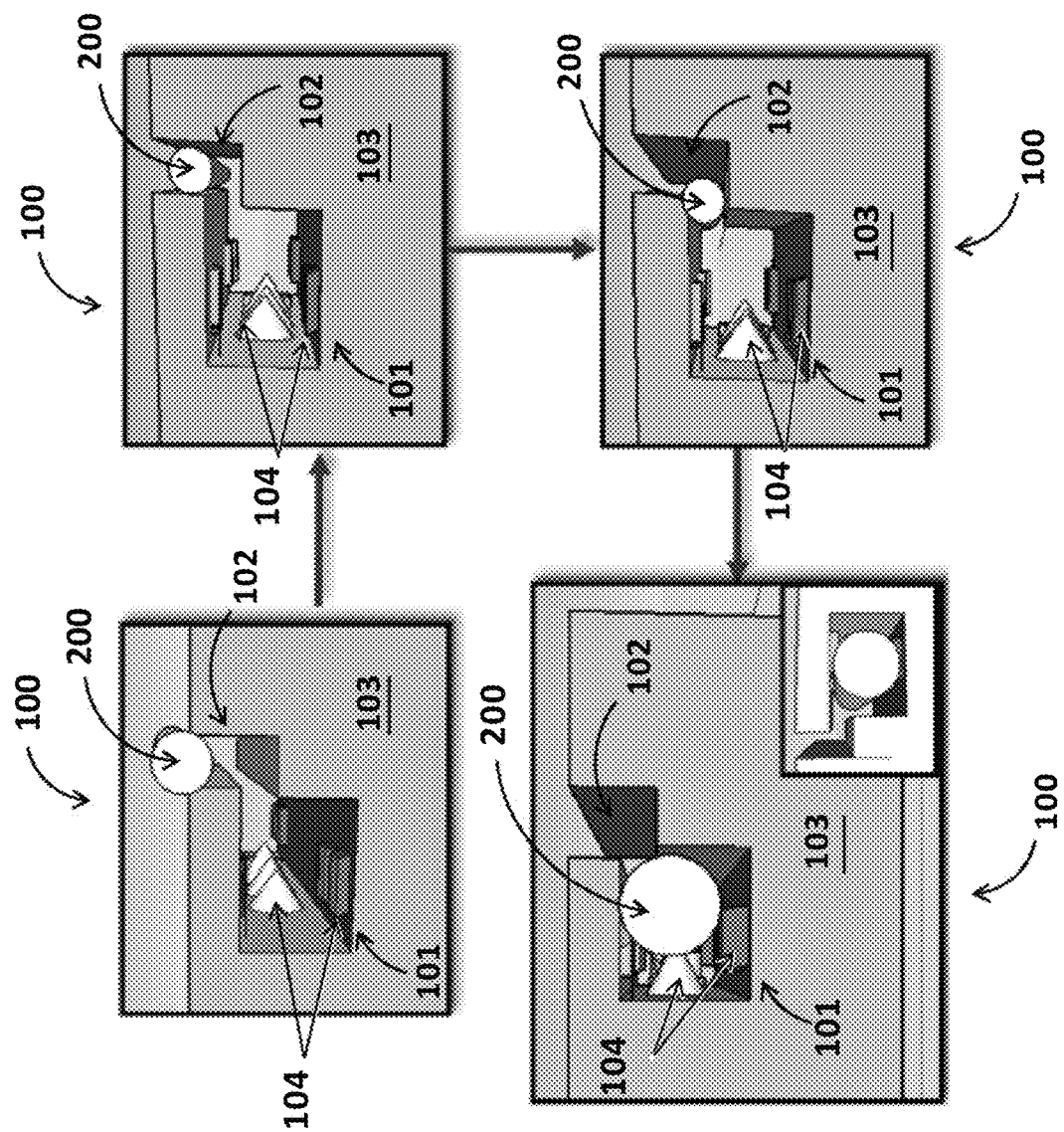
FIG. 2 is a profile view schematic of a device described herein receiving a nerve.

FIG. 2 illustrates the steps of implantation of the so called "NeuroClip" electrode (an exemplary embodiment of the present disclosure) through the innovative slide-n-lock method. Target nerves 200 slide longitudinally into an opening or channel with an internal diameter 25% less than the inserted nerve 200 diameter, transiently undergoing a minimal elongation longitudinally and compression transversely.

Additionally, some embodiments of a device 100 include extended features as to provide either a top, bottom or side access to the nerve 200. FIG. 2 shows an example embodiment having a simple "L-shaped" channel to enhance the locking mechanism with minimal additions to the design architecture.

Example 2

Fabrication of a Device for Neuromodulation

A neuromodulation device (a "Neuroclip version I") was fabricated at using flexible polyimide/SiC substrates with gold metallization in ultra-micro scale for intraneural electrode features with two sets of tripolar extraneural iridium oxide electrodes using established thin-film methods. Thin-film fabrication techniques provide the unique opportunity to miniaturize the electrode design to accommodate the small caliber neural interfacing. The multi electrodes grouped in tripolar configuration not only provide specificity and selectivity but also reduce the effective biological noise components. Further we also describe a wireless option with a wireless integrated circuit added to the NeuroClip electrode in a two-layered device integration and encapsulation.

Figure 1D:
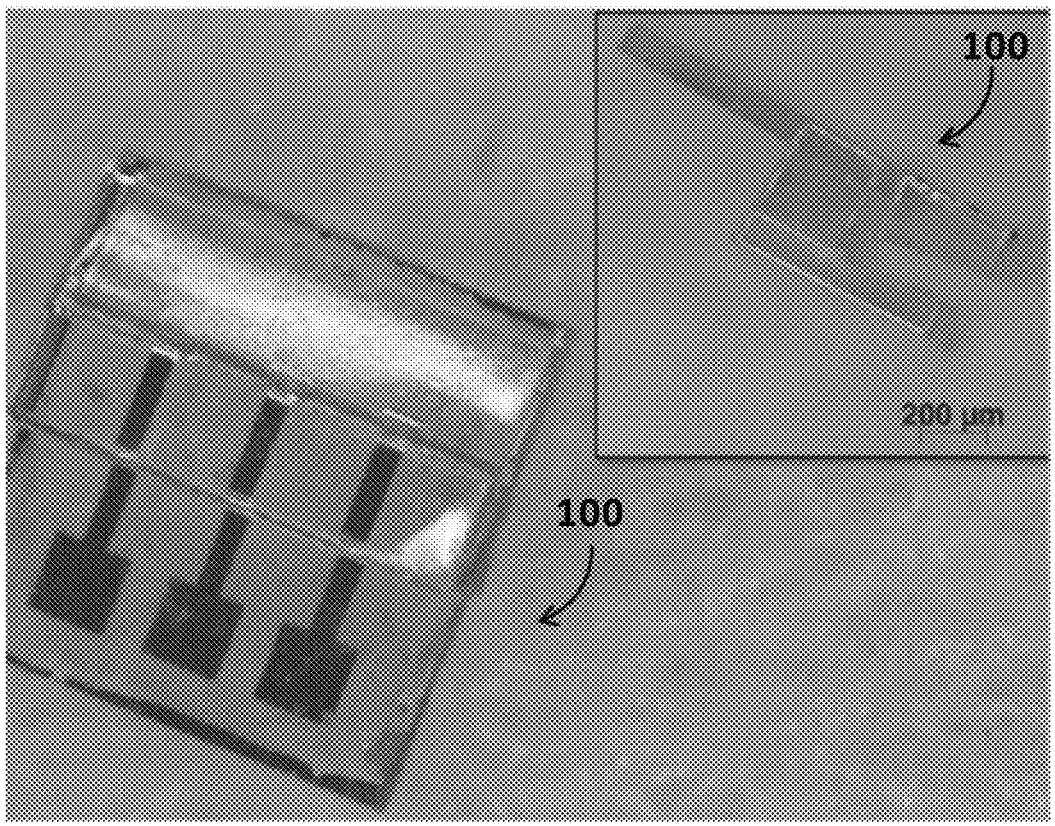
FIG. 1D is a photograph of a neuromodulation device.
Figure 1E:
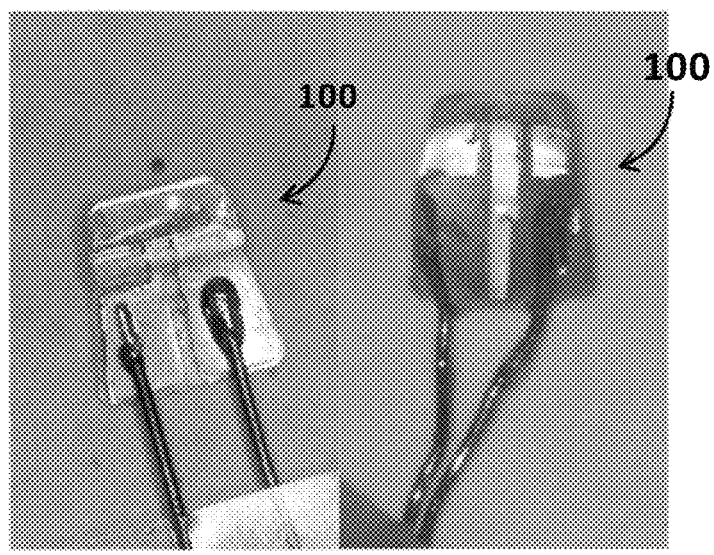
FIG. 1E is a photograph of a neuromodulation device.

Functional devices were fabricated with Su8 to test the slide-n-lock mechanism of neural implantation approach. FIG. 1D shows the Su8 NeuroClip electrode layout schematics. The electrodes were then fabricated in collaboration with MiNDS lab, UTD (Micro/Nano Devices and Systems), adapting previously described steps. Post-fabrication and UV sterilization for 30 minutes, the NeuroClip was implanted onto the Glossopharyngeal rootlet to test the slide-n-lock mechanism (FIG. 1E). Additionally, when compared with the commercially available microcuff electrodes, the time, and steps involved with implantation have significantly reduced.

Example 3

Fabrication of a Device for Neuromodulation

Figure 3A:
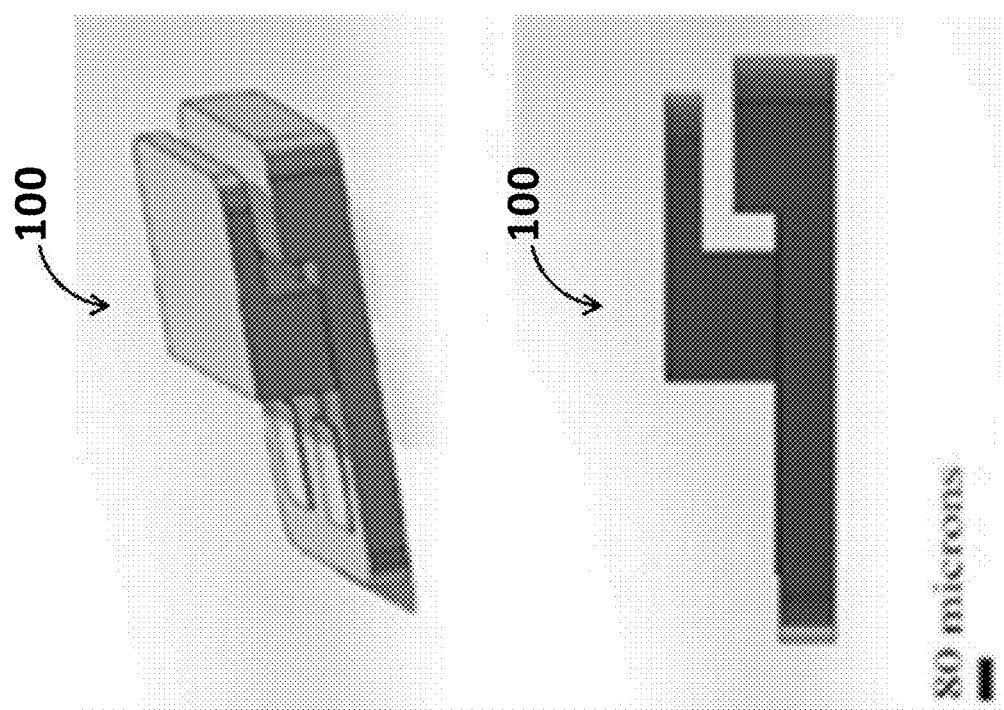
FIG. 3A is a schematic representation of a neuromodulation device described herein.
Figure 3B:
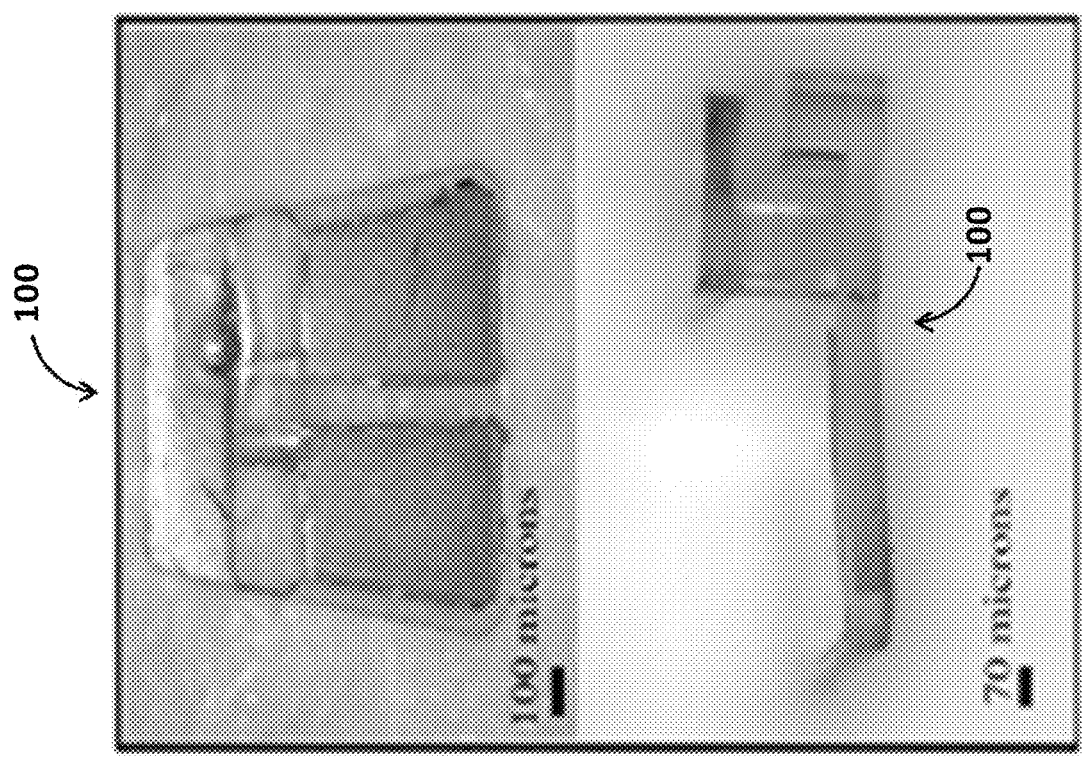
FIG. 3B is a photograph of a neuromodulation device.
Figure 3C:
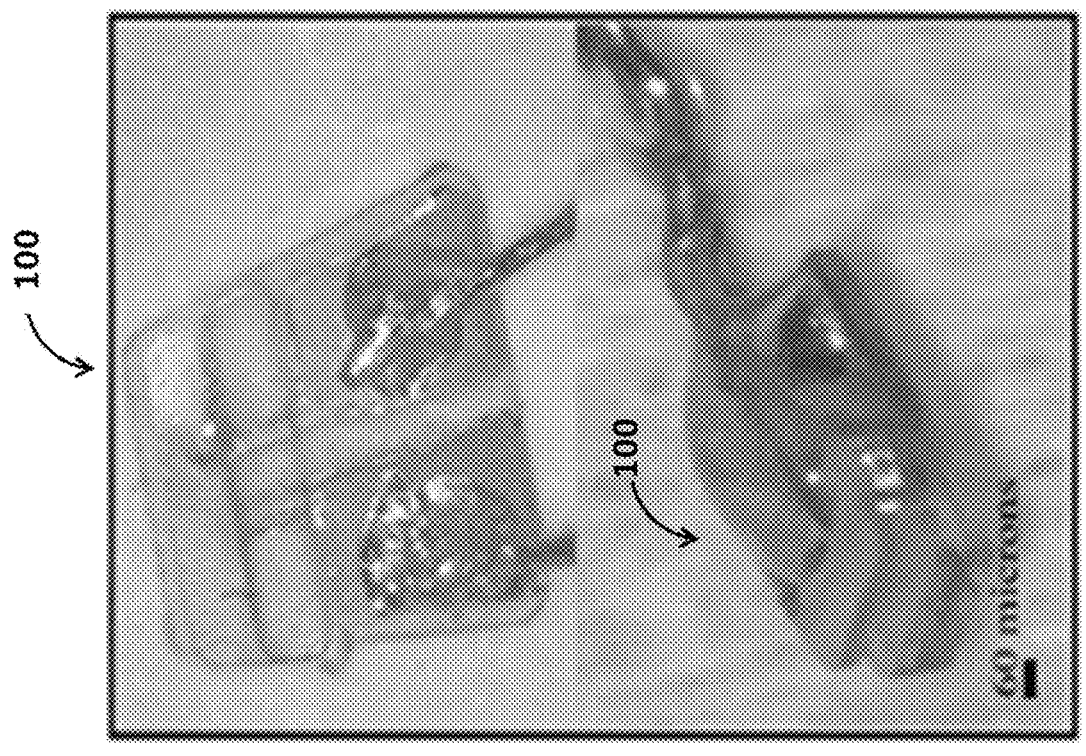
FIG. 3C is a photograph of a neuromodulation device.
Figure 4:
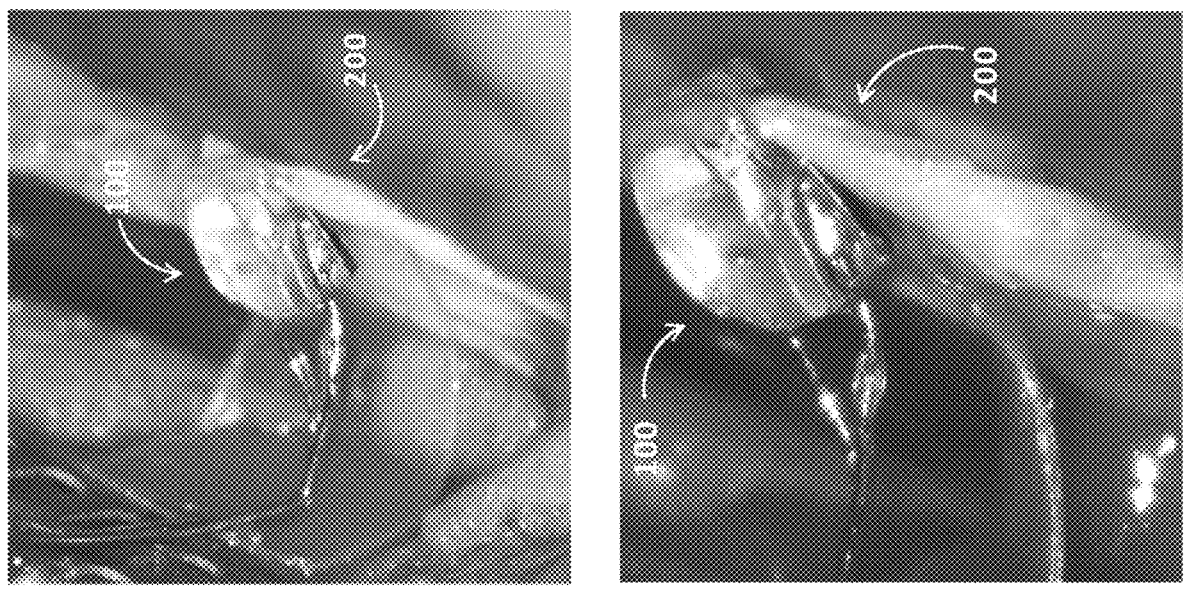
FIG. 4 is a wired neuromodulation device, as described herein, having a 100-200 micrometer fascicle of a rat deep peroneal nerve disposed in the chamber.

A second version of a neuromodulation device ("NeuroClip version II") was fabricated similar to the version I except for the number of electrode contacts. FIG. 4 shows the Su-8 fabricated NeuroClip V2. Version II comprises curved corners and cantilever structures for one channel slide-n-lock mechanism (FIG. 3).

Prior to implantation, the NeuroClip's were characterized in-vitro to evaluate the electrochemical impedance. The devices were placed in phosphate buffered saline and a 3 cell electrochemical cell was formed using an Ag—AgCl reference electrode and Pt wire counter electrode. The typical impedance spectroscopy was obtained using the Gamry Potentiostat (GamryInstruments). Impedance at 1 kKz was around ~500 KOhms across two electrodes.

Example 4

Functional Testing of Neuromodulation Device In Vivo

Acute testing of a neuromodulation device having embodiments described herein was carried out in adult Female Sprague Dawley rats weighing up to 500 grams. The animals were anesthetized with inhaled isoflurane (1-3%) from a vaporizer with scavenger system. The appropriate level of anesthesia was confirmed by the lack of response to noxious stimuli. Animals were kept under anesthesia throughout the experiments, body temperature was maintained with heating pads, and each rat's condition was monitored continuously via a pulse oximeter on the extremities.

The left hind limb deep peroneal nerve was exposed and the dorsal fascicle was teased out gently with the help of glass rods. The teased fascicle was then placed and secured into the microchannel of the NeuroClip using the slide and lock mechanism. FIG. 4 shows the device 100 attached to a 100 micrometer fascicle of the rat peroneal nerve 200. All animal procedures were performed in accordance with the guidelines of the Institutional Animal Care and Use Committees of the University of Texas at Dallas.

The nerves were then stimulated using an AM systems Stimulator (A-M Systems). Animals were kept under anesthesia throughout the experiment and body temperature was maintained with heating pads and its condition was simultaneously monitored continuously via a pulse oximeter on the extremities. The animals were placed prone to allow for an uninterrupted video recording of foot and toe movement using hardware and software solutions provided by Cineplex Behavioral Research System (Plexon Inc.). Videos were acquired at 80 frames per second. Individual electrodes were stimulated with a gradual increase in the current 1 mA to 2 mA to identify the threshold currents at which a visible isometric twitch was observed. Charge-balanced constant-current rectangular pulses (1 ms duration, 2 Hz) were used to evaluate the toe kinematics. Toes were painted with animal safe dyes for color-based tracking. With appropriate hue, contrast and saturation adjustments, the individual dye contours were identified in Cineplex. The geometric centroid of the dyed region was then tracked in the x-y plane, and was used to compare and contrast the tor recruitment patterns with respect to increase in stimulus current.

Figure 5:
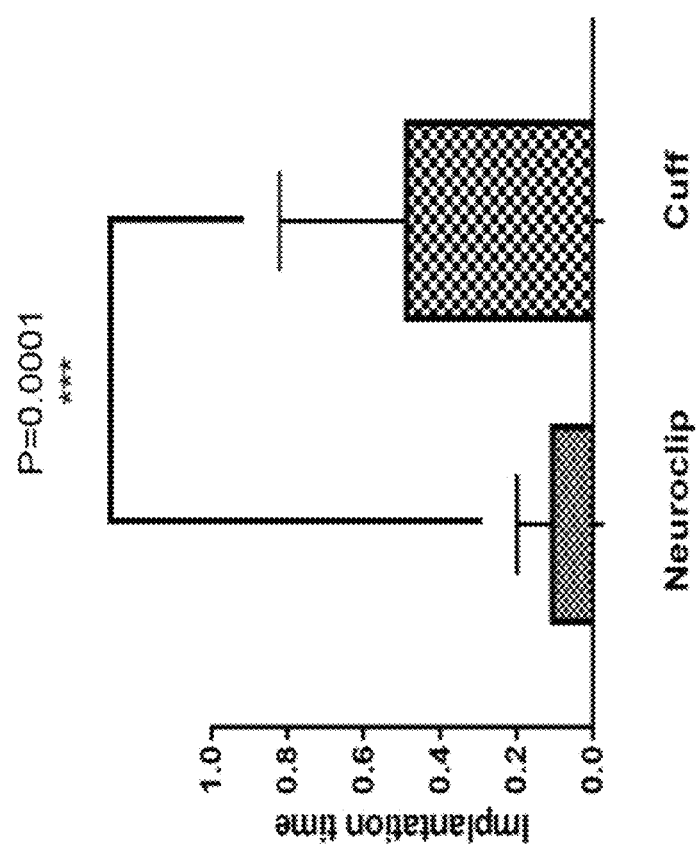
FIG. 5 is a bar graph illustrating the reduced time of implantation needed to place the nerve on the neuromodulation device described herein ("neuroclip") compared to a cuff electrode.

The amount of time required for implantation of the neuroclip compared to placing a standard cuff electrode was tested in these small nerves by two independent surgeons with no prior experience in either method. Post exposure of DPN fascicle, cuff electrode (diameter 100 μm) and neuroclip were implanted alternatively in the exposed fascicle. The procedure was recorded by surgical camera. This was repeated 7 times. The time of implantation was calculated from the recorded video by means of activity tracking. FIG. 5 shows timing of implantation in the DPN fascicle for neuroclip (dia~80 μm) and cuff electrode (dia~100 μm indicating that the time of implantation of neuroclip is significantly less (p=0.0001). The neuroclip reduced up to 90% the time, and therefore, handling required to place electrodes in these small nerves of nerve fibers. Further, surrounding anatomy was only minimally manipulated within the time frame, thus providing small implantation window and reducing the possibility of tissue damage.

The implanted fascicle in the neuroclip was stimulated with constant voltage cathodic first biphasic electrical stimulation of 1 ms long charge-balanced pulses at 2 Hz frequency. Electromyograms (EMG) were recorded from the Tibilias anterior muscle using needle electrodes. The stimulation pool of five voltages was selected by way of increasing the amplitudes by 0.1 mV from the recorded threshold amplitude. The experiment was repeated for three trials with every trial consisting of randomized amplitude testing blocks from the stimulation pool. The stimulation was carried out for a period of 30 secs with a 1 min rest time between varying stimulation amplitudes. The rest duration between consecutive trials was 5 mins to overcome muscle fatigue and residual effects from previous stimulation trials.

The electrochemical characterization across 7 electrodes gave an average impedance value of 250.63±53.42 KΩ at 1 KHz frequency. The charge storage capacity was calculated from the CVs. The cathodic charge storage capacity had an average value of 0.231±0.12 mVcm-2 and the average charge per phase reported was 0.65±0.20 nC.

Figure 6A:
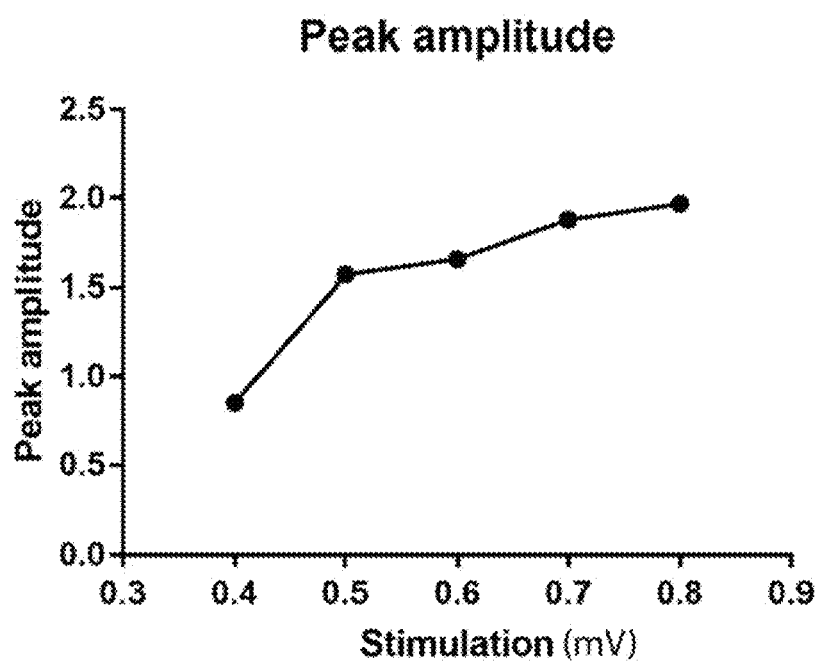
FIG. 6A is a line graph of recording capabilities of a neuromodulation device, as described herein.
Figure 6B:
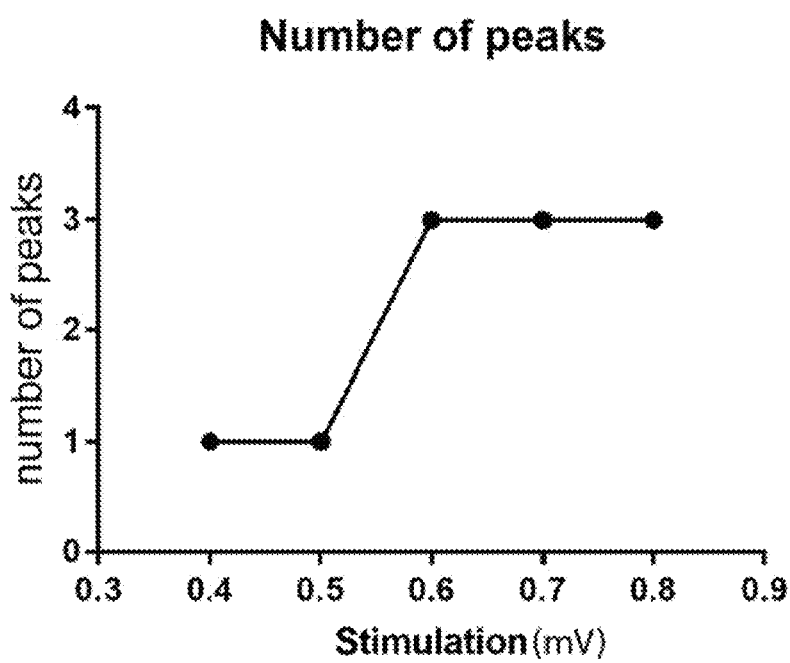
FIG. 6B is a line graph of recording capabilities of a neuromodulation device, as described herein.

FIG. 6 shows recording capabilities of neuroclip. FIG. 6A shows increasing largest peak amplitude of recorded CENG with increasing stimulation amplitude. FIG. 6B shows increasing number of peaks with increasing stimulation amplitude indicated activation of more fibers. Increased amplitude of the stimulation post threshold gave rise to an increase of peak-to-peak amplitude of first peak in compound action potentials indicating increased activation of motor fibers for muscle recruitment. Further increasing the amplitude to 0.9 mV gave rise to secondary peaks corresponding to recruitment of slower fiber types.

Increasing stimulus amplitude post threshold gives rise to increasing limb recruitment observation in recorded EMGs.

FIG. 7 illustrates testing of recording capabilities of neuroclip based on electrical stimulation by a hook electrode [n=3]. Neurograms of compound action potentials were recorded with the implanted neuroclip in response to proximal hook stimulation on DPN. The distance between the two electrodes was about 2±0.5 mm. The stimulation parameters were same as reported above with randomized testing blocks for each trial. Stimulation using a hook electrode showed increased activation of fibers with increased stimulation amplitude. Increased activity is captured in compound action potentials post threshold hook stimulation. The stimulation threshold for recorded compound action potentials by the neuroclip was 0.5±0.1 mV for a visible muscle twitch.

Figure 8A:
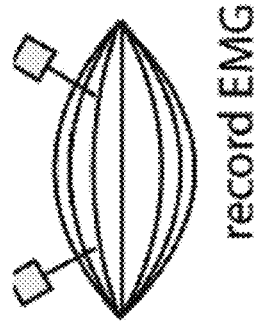
FIG. 8A is a schematic of a neuromodulation device with a stimulating electrode.
Figure 8B:
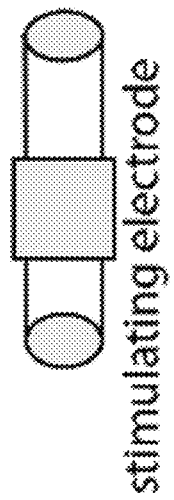
FIG. 8B is a schematic of a muscle recording device that is not within the scope of neuromodulation devices described herein.
Figure 8C:
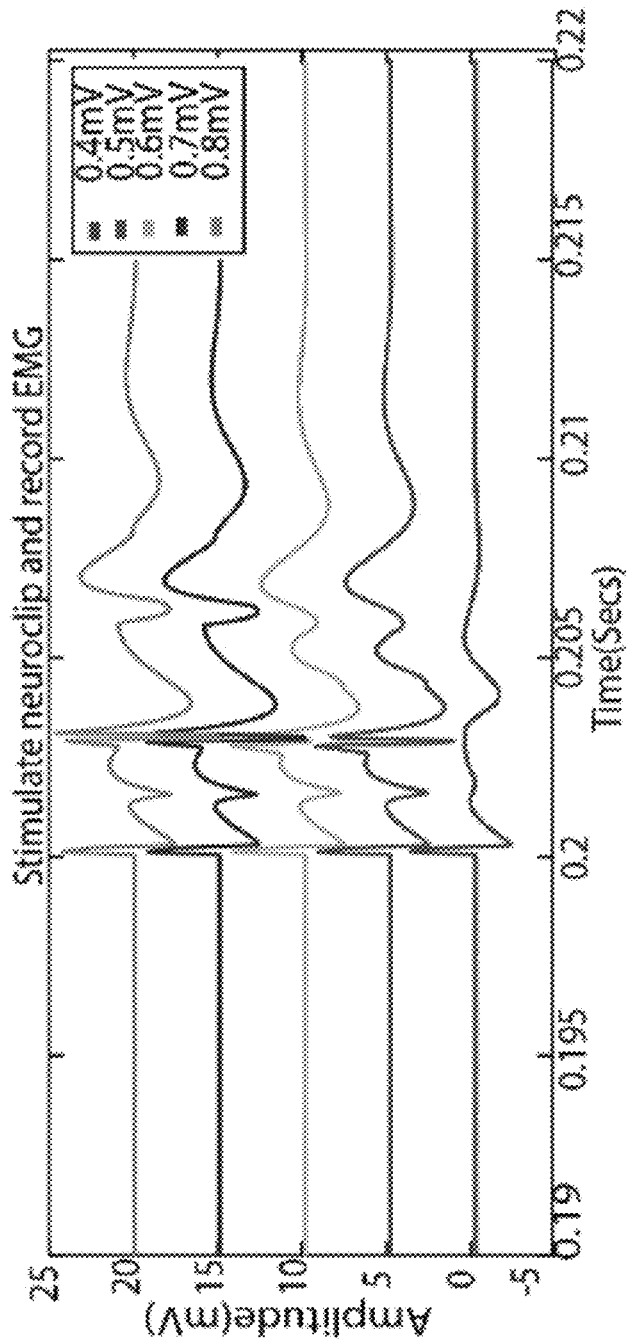
FIG. 8C is a line graph of stimulation capabilities of a neuromodulation device, as described herein and evoked muscle activity.
Figure 9:
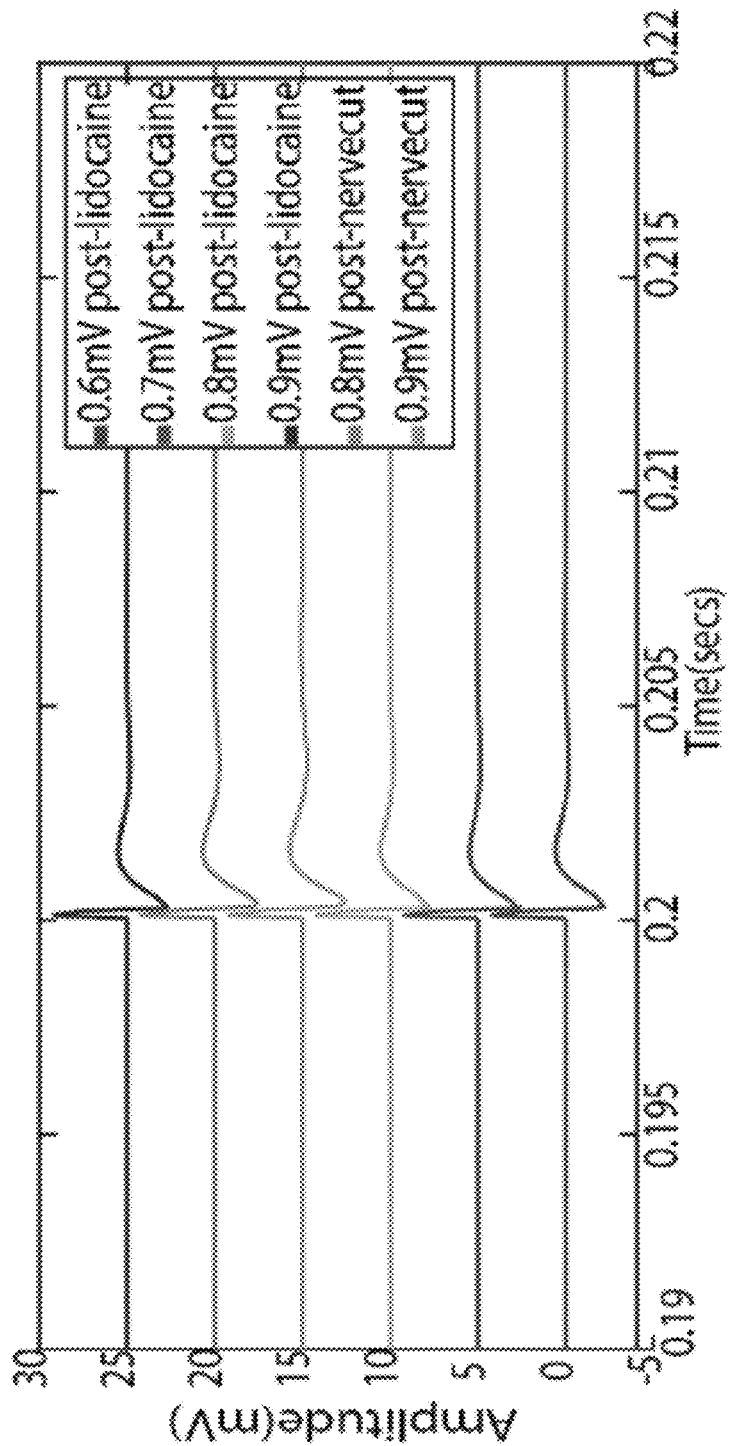
FIG. 9 is a line graph of a control experiment to test the stimulation capabilities of a neuromodulation device, as described herein.

FIG. 8 illustrates the stimulation capabilities of the neuroclip. EMGs recorded from the TA muscle while stimulating using neuroclip show increased response with increased stimulation amplitude. FIG. 9 shows control experiments wherein EMGs were recorded post lidocaine and nerve cut, which show only a stimulation artifact, indicating that the response previously recorded was due to neural stimulation.

A number of small peripheral neural interfaces including nerve cuffs and wired or wireless systems can be used to neuromodulate these small nerves and fascicles.

It should be especially noted that devices 100 described herein, in some embodiments, do not need to be "open" for nerve insertion, nor "closed" after nerve placement. Instead, devices 100 described herein can retain nerves without carrying out such additional steps or modifications of the device 100 structure.

Additionally, described herein are Implantable Neural Interfaces for chronic neuromodulation (recording, stimulation and blocking potential) which provide a) safe and reliable long-term interfacing, b) selectivity, c) low signal to noise ratio, and d) adaptability for varied nerve geometries. This device can be used for the bidirectional link with robotic prosthetic devices, peripheral neuromodulation and bioelectronic medicine applications.

Example 5

Neuromodulation of Pelvic Floor Muscles

To illustrate various features of the disclosure, an exemplary wireless device was implanted into several motor branches innervating individual pelvic floor muscles in healthy young and old adult female rabbits. The results are presented below in the context of FIGS. 11-14.

Figure 11:
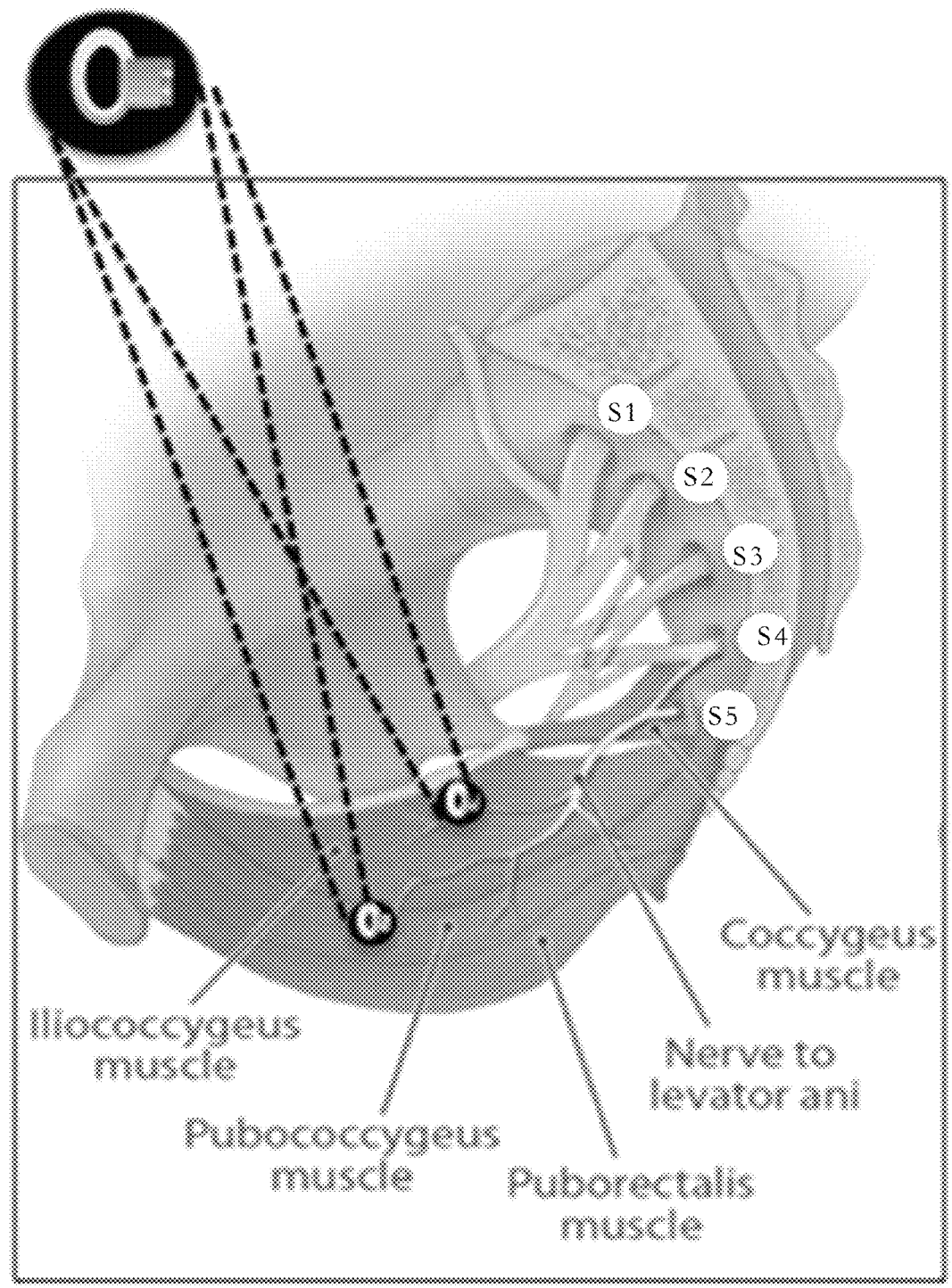
FIG. 11 is a cartoon representation of methods of neuromodulation, as described herein.

FIG. 11 illustrates an example nerve cuff placed onto the small nerves controlling the pelvic muscles.

Figure 12A:
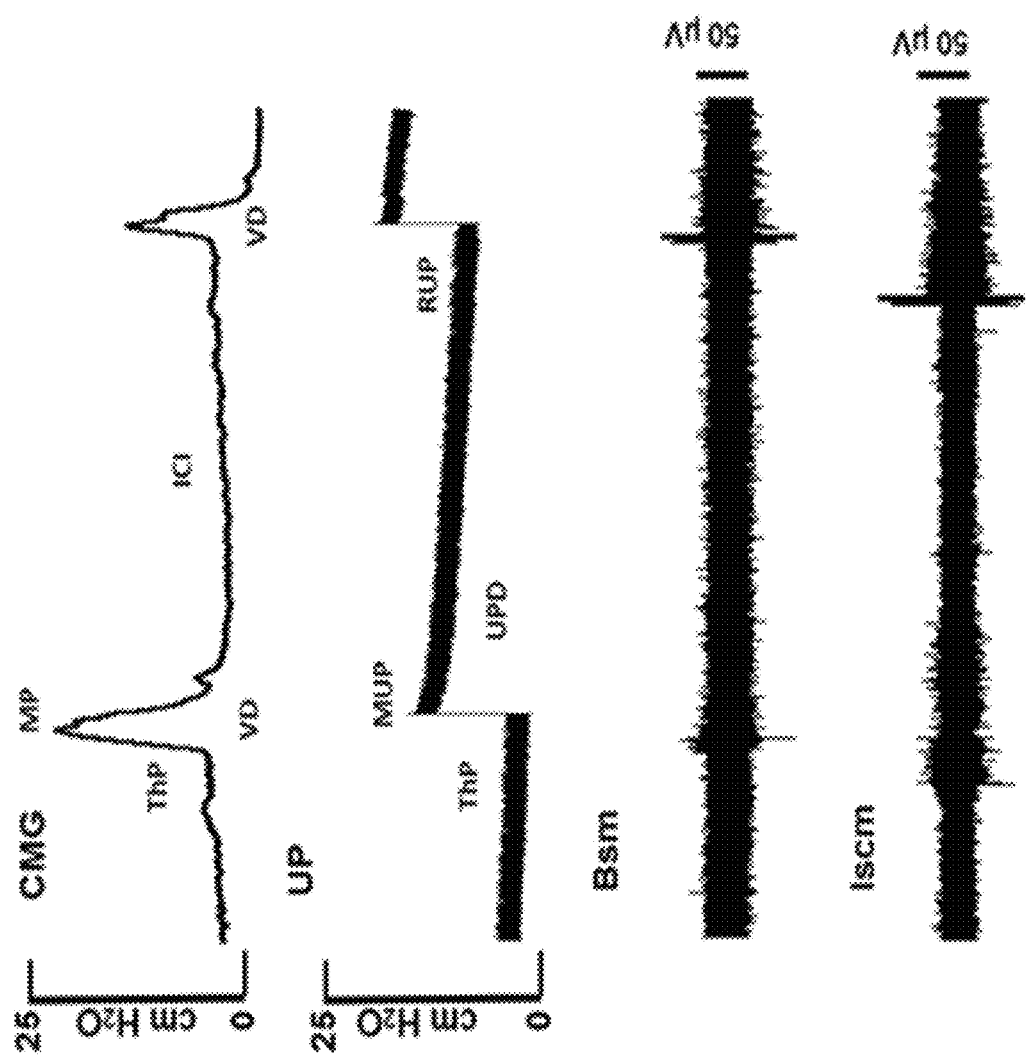
FIG. 12A is cystometrogram (CMG), uretheral pressure (UP) and recordings of rabbit pelvic floor muscles.
Figure 12B:
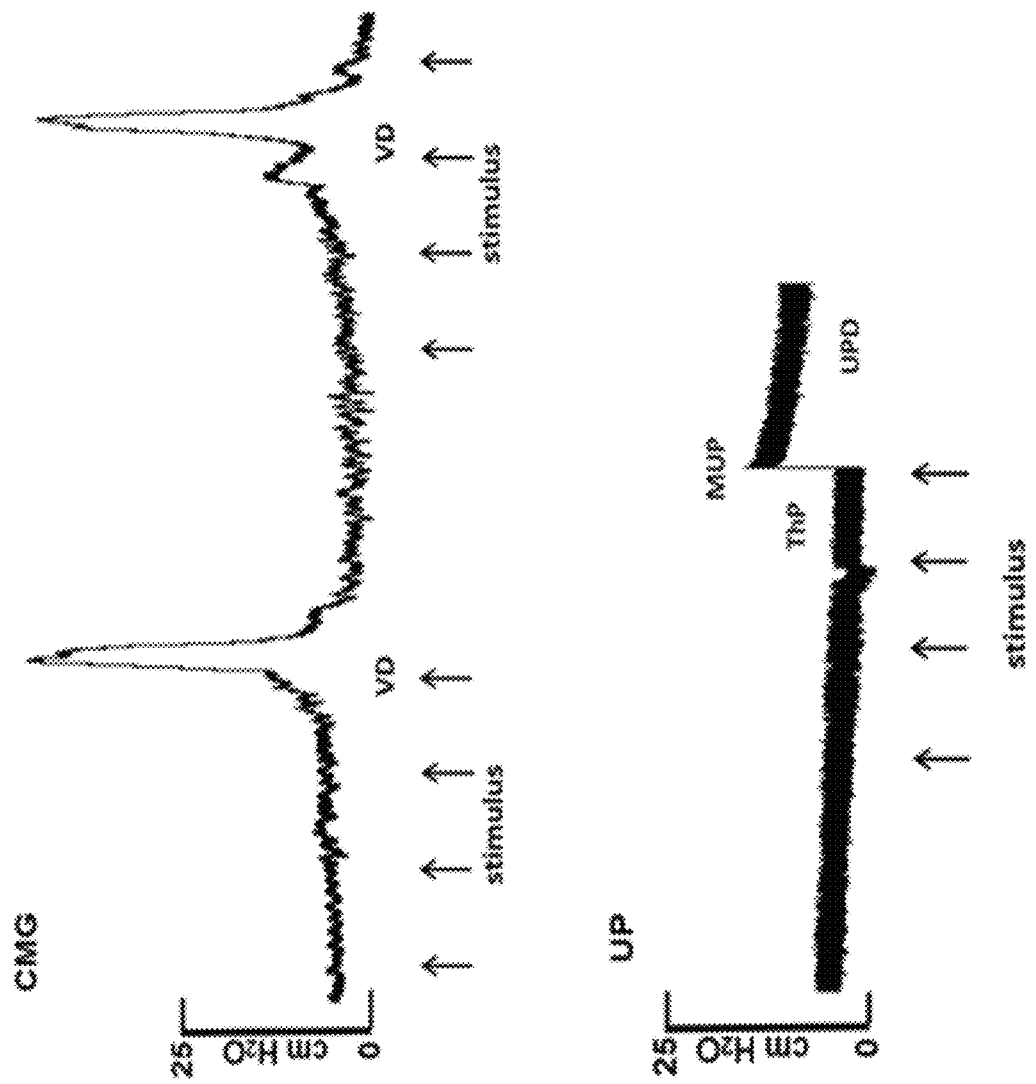
FIG. 12B shows the effect of stimulation of pelvic floor nerves (arrows) on the cystometrogram (CMG) and uretheral pressure (UP) in rabbits.

FIG. 12 shows the normal urodynamic response of a young nulliparous rabbit (FIG. 12A) and how the bladder storage capacity and voiding efficiency in response to direct Bsm acutely in anesthetized animals. Stimulation of this nerve at 2 Hz for 10 min induced voiding and improving storage capacity by neuromodulation of nerves controlling individual pelvic floor muscles.

Figure 13A:
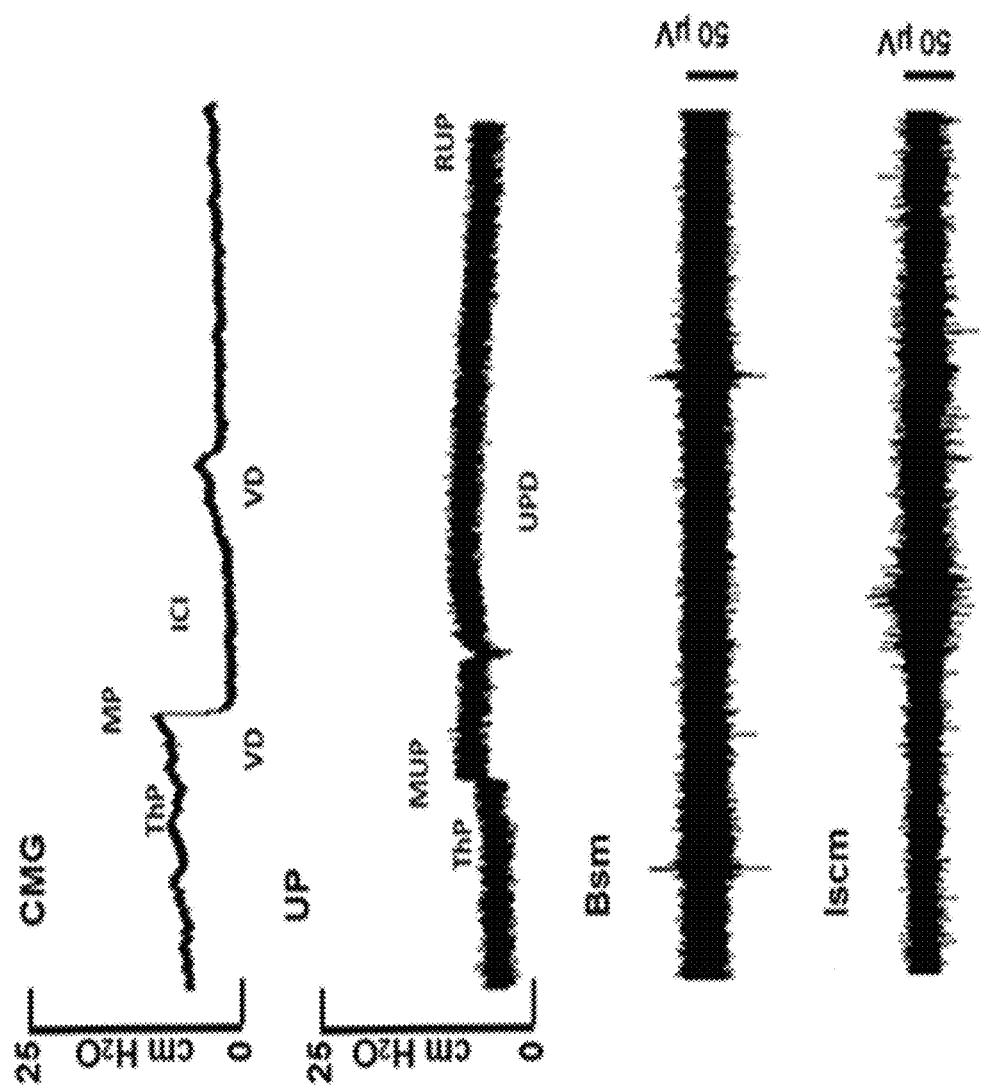
FIG. 13A shows a reduced cystometrogram (CMG), uretheral pressure (UP) and recordings of rabbit pelvic floor muscles in an animal model of stress urinary incontinence.
Figure 13B:
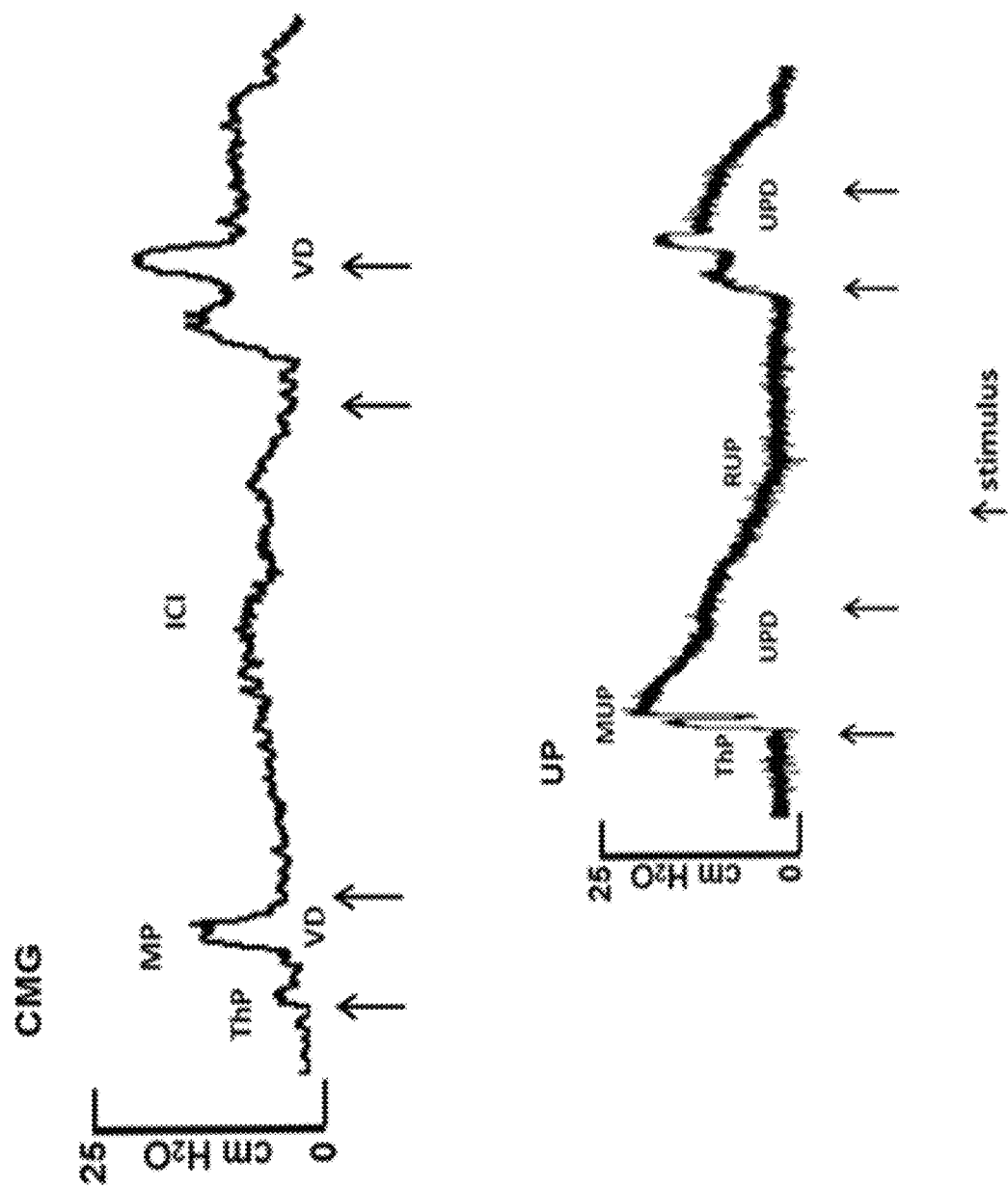
FIG. 13B shows an increased cystometrogram (CMG) and uretheral pressure (UP) in an animal model of stress urinary incontinence.

FIG. 13A illustrates how the severely compromised bladder function in 3-4 year old rabbits, showing less than 12.5 cm H2O with a corresponding reduction of urethral pressure to approximately 20-30% of that in a normal animal. Not intending to be bound by theory, it is believed that the deficit in the reported animal may be the result of Bsm and Icm muscle dyssynergia. After specific neuromodulation of the pelvic floor muscles these animals showed immediate improvements in symptoms and visible improvement in urine stream, resembling that characteristic of younger animals. After electrical stimulation of the Bsm nerve we observed a significant increase in both urine volume and urethral pressure.

In old nulliparous rabbits the synergy between the bladder and urethral function are expected to be dysfunctional due to neurogenic, myogenic or mixed factors, resulting in inefficient activity of Bsm and Iscm. If the nerve and muscle are at least partially functional, PFNS may reverse the effects on bladder and urethral dysfunction characteristics, through increased voiding efficiency, the maximum urethral pressure and urethral closure.

Figure 14A:
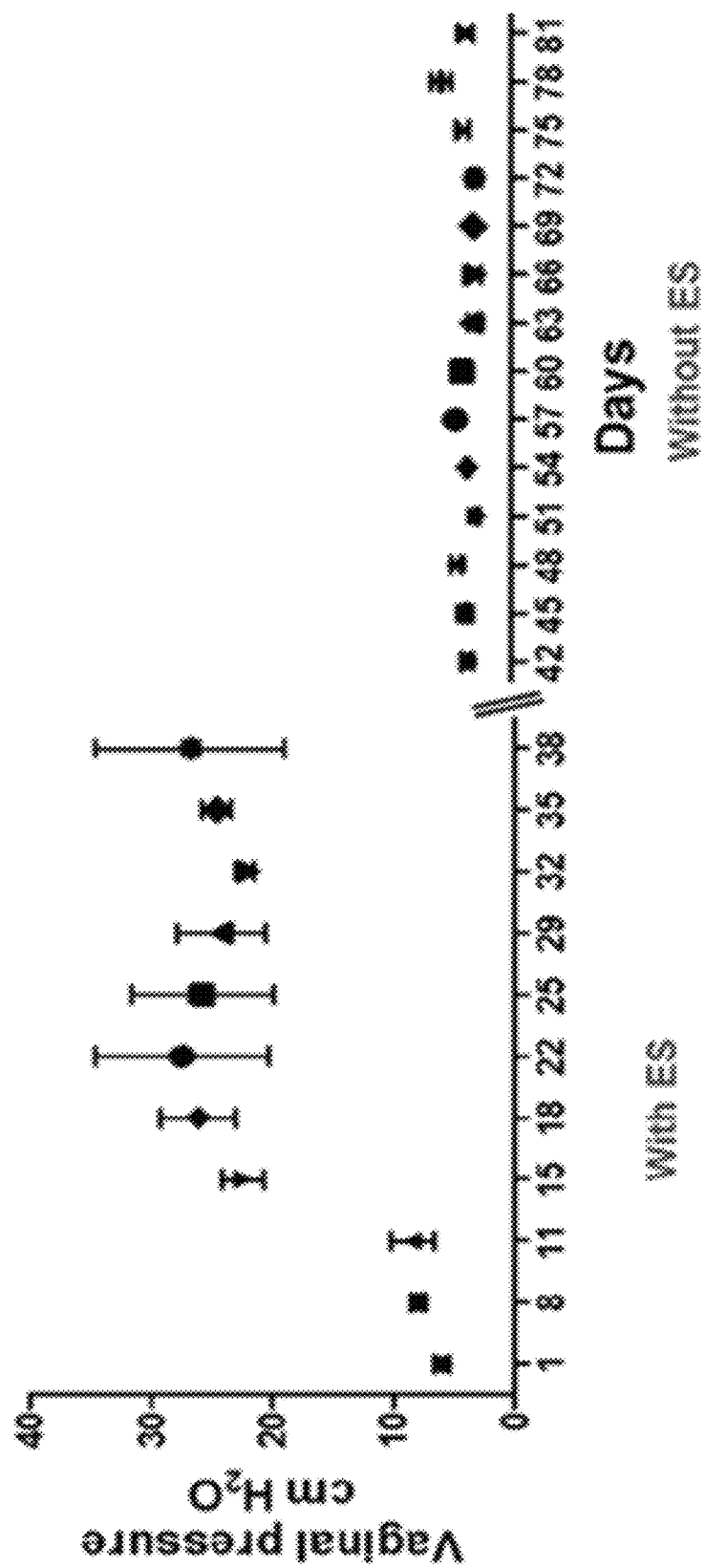
FIG. 14A is a graph of vaginal pressure in rabbits.
Figure 14B:
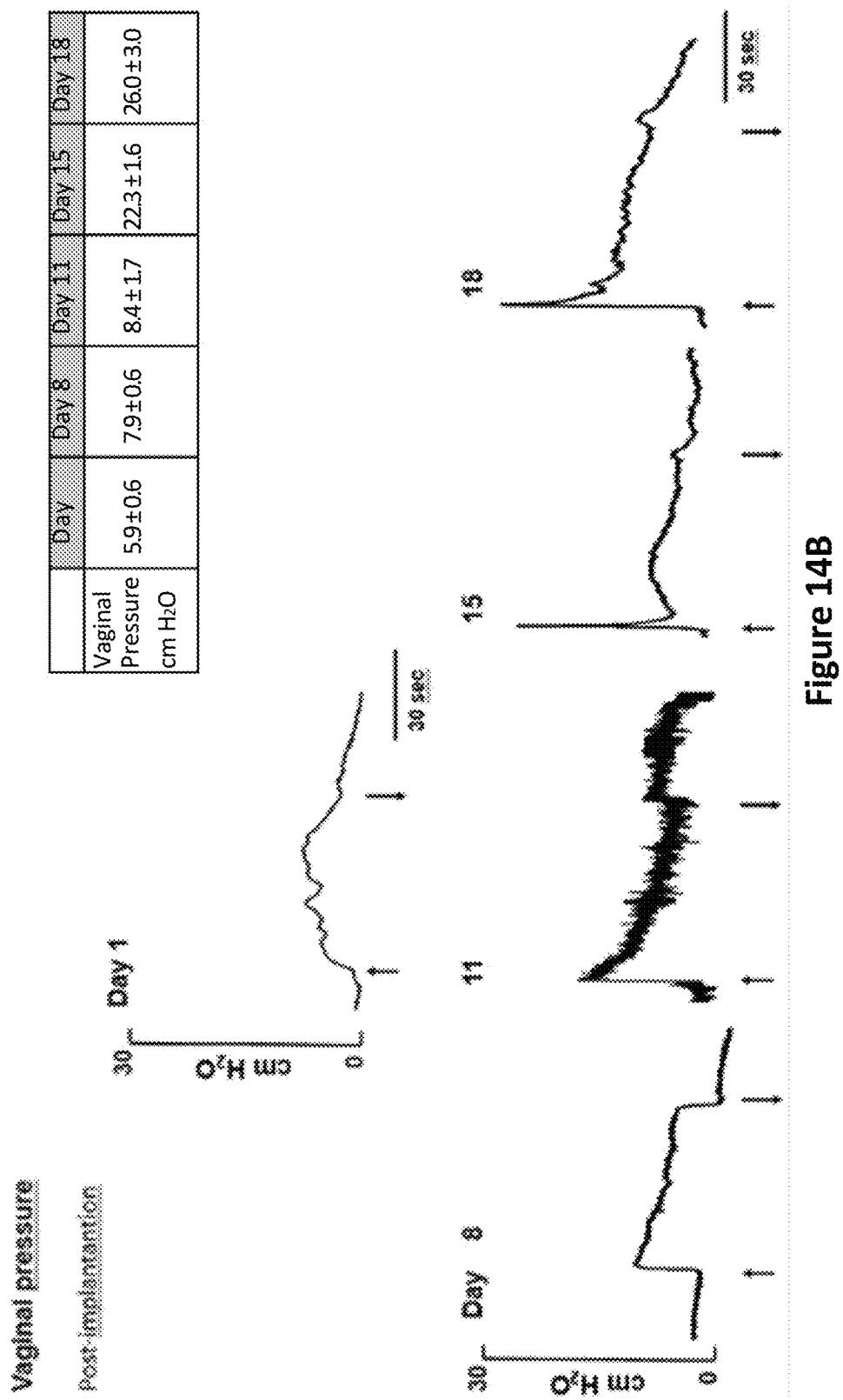
FIG. 14B is a graph of vaginal pressure in rabbits.

FIG. 14 shows the implanted and stimulated onto the Icm on a young animal who received 10 min of stimulation at 2 Hz and 40% amplitude levels 3 times per week while fully awake for 38 days. An intravaginal pressure sensor was used to determine the effect of the treatment at several time points as contraction of the Icm increases vaginal pressure.

An "ON-OFF" protocol was followed with 38 days for stimulation and discontinued thereafter. We were able to show a slight effect on the first week, which increased 15 days after implantation, reaching an overall 3-fold strengthening of the PFM plateauing thereafter.

Discontinuation of the electric stimulation of this nerve for 43 days regressed the activity to base-line levels. This result provides robust evidence of the benefit of specific pelvic floor nerve modulation.

Example 6

Wireless Stimulation of Pelvic Floor Motor Efferents Neuromodulate Micturition in Female Rabbits More than 40% of women suffer from lower urinary tract (LUT) disorders including deficient bladder emptying and urinary incontinence. Electrical stimulation of the S3-S4 root or the pudendal plexus that innervate several pelvic and perineal targets is considered currently a viable alternative treatment of several LUT dysfunctions. However, this therapy seems to increase urinary retention in some patients, and urinary voiding in others. These contradictory effects seem to be, at least in part, due to the indiscriminatory activation of both efferent and afferent fibers in the sacral or pudendal plexi in the pelvic floor. We sought to investigate whether stimulation of the specific motor efferent innervating the ischiocavernosus, (Icm) and bulbospongiosus (Bsm) muscles in the pelvic floor would modulate the bladder emptying response. We believe these muscles deploy asynchronous activity during urine storage and bladder emptying. Nulliparous adult young female rabbits were implanted acutely with a novel wireless miniature cuff electrode (WMCE) that uses RF at a 10.7 MHz frequency to power a 1 mm transistor-less device attached to a custom nerve cuff. A diode in the WMCE was used to produce a 400 us cathodic pulse and deliver a 400 mV potential to the target nerves. The animals were stimulated for 30 seconds at 2 Hz and repeated 3 times with a 10-minute inter-stimulation delay. Cystometrograms were recorded before and during the WMCE stimulation and the threshold volume of the bladder, voided and residual volume, and the voiding efficiency were quantified. The results showed that wireless stimulation of the Bsm and Ism nerves the increase the maximum pressure of the bladder. These results demonstrate the efficacy of wireless neuromodulation of perineal muscle nerves for affecting bladder function. We describe herein an approach (including systems, devices, and methods) that can, in some cases, offer a more selective treatment for urinary incontinence.

Example 7

Selective Stimulation of Pelvic Floor Muscles

Impaired bladder emptying is a common clinical condition exhibiting lower urinary tract symptoms (LUTS) that affect almost 25% of the female and 10% of male population in the US alone. The underactive bladder (UAB) and detrusor underactivity (DU) are common types of LUTS. Summated the implications of menopause with to aging, most women spend more than a third of life with pelvic floor dysfunctions apparently exacerbated during aging. The PMF muscles, namely the bulbospongiosus and bulbocoxigeous nerves, innervate muscles of the same name. These pelvic muscles are part of a complex neuro-muscular coordination of the lower urinary tract (LUT) and play a critical role in the control of micturition, defecation and sexual functions. Moreover, damage to the LUT due to childbirth, trauma, or aging results in urinary incontinence.

Figure 10:
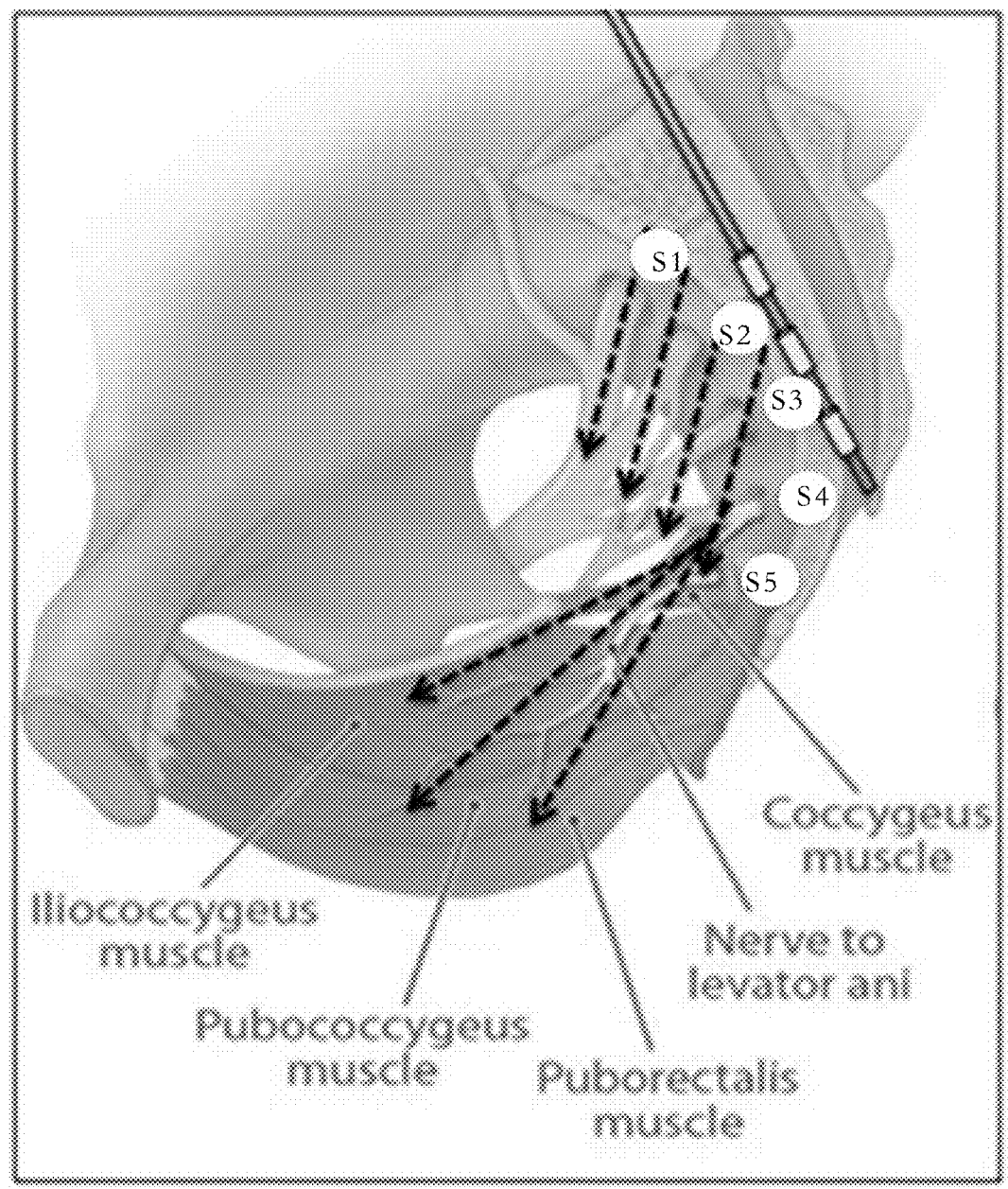
FIG. 10 is a cartoon representation of Prior Art methods of neuromodulation.

Electrical stimulation of the sacral nerves (S3-S4) innervate pelvic and perineal targets, and has been an established method for the management of several urinary tract dysfunctions since 1997, particularly of overactive bladder (OAB) (FIG. 10). Medtronic's Interstim™ device has been implanted in more than 200,000 patients globally, and the efficacy has been reported to be 50% in mediating urinary retention. It is believed that stimulation of afferent sensory fibers negatively modulates excitatory synapses in the central micturition reflex pathway.

However, neuromodulation has not been widely accepted as a first-line treatment for urinary incontinence, and its use is reserved for those unresponsive to all other treatments. At least in part, this is due to the fact that therapeutic mechanism are not understood, particularly when the therapy seems to mediate increase urinary retention in some patients and urinary voiding in others. There is also much disagreement as to whether the pelvic afferents or efferents nerves are needed, and whether direct or polysynaptic reflex mediate the effect. The contradictory results may be explained at least in part by the non-specific nature of the treatment as S3-S4 nerves branch into the hypogastric nerve (afferent sensory/efferent sympathetic), and the pelvic nerve (afferent sensory, efferent somatic), which provides innervation to the urethra, the external anal sphincter, the levator ani muscles, the perineal skin, and the clitoris. Furthermore, there are significant variations with respect to the origin and course of the pudendal, levator ani, and inferior rectal nerves that make the application of the therapy uncertain and difficult to standardize.

We disclose herein that neuromodulation of the bulbospongiosus nerve can re-establish a normal micruition pattern in a rabbit model of urinary incontinence. We further describe the clinical benefit of direct and specific control of small PFM.

Applications of the present disclosure include the access of small nerves which are traditionally difficult due to size and location, such as the clitoris nerve.

Group unilateral electrical stimulation of Bsm nerve in young nulliparous rabbits: Before of electrical stimulation of the Bsm nerve the recordings of cystometrogram (FIG. 13A), urethral pressure (FIG. 13A) and electromyogram activity from perineal muscles (FIG. 13A) were simultaneously obtained in YN. Both storage and voiding phases of micturition were observed (FIG. 13A).

Group unilateral electrical stimulation of Bsm nerve in old multiparous rabbits:

FIG. 1: Electromyogram recordings of (FIG. 13A, Bsm) and (FIG. 13A, Ism) muscles during the micturition and with electrical stimulation of Bsm nerve (FIG. 13B) in anesthetized old multiparous rabbits.

Storage and voiding phases of the micturition are indicated. ThP; MP; VD; ICI; ThP, threshold urethral pressure; MUP; UPD; RUP, pressure to return to baseline; s, seconds. ↑ Electrical stimulation of Bsm nerve. Before of electrical stimulation of Bsm nerve was observed that the multiparity and age affected bladder (A), urethral function (B) and activity pattern of perineal muscle (C, D). Detrusor muscle contraction decreased. Electrical stimulation proved to total bladder volume and the urethral pressure, significantly improving the urinary incontinence condition in the rabbit.

We have also shown the chronic neuromodulation of the Isch motor nerve. See FIG. 14: Vaginal pressure during the electrostimulation of Iscm nerve postimplantation of miniature wireless nerve cuff electrode in young nulliparous rabbit. The stimulation of Iscm nerve produced different changes of vaginal pressure in the first day postimplantation of miniature wireless nerve cuff electrode elevated the pressure of the vagina at 1, 8, 11, 15 and 18 days. ↑ starting stimulation, ↓ finishing stimulation. Novel and discriminatory factors described herein include the selectivity of the stimulation by targeting small nerve branches that directly innervate specific organs.

Example 8

Stimulation of the Pelvic Floor Muscles for Treatment of Pelvic Floor Disorders

As disclosed herein, the pelvic floor includes several muscles organized into superficial and deep layers including those in the levator ani: iliococcygeus (Icm), pubococcygeus (Pcm; also known as pubovisceralis), coccygeus (Cgm), and the puborectalis (Prm), and those in the urogenital diaphragm: bulbospongiosus (Bsm) and ischiocavernosus (Ism).

Each of the above discussed muscles has a unique origin-insertion and line of action. Further, each of the above discussed muscles has specific patterns of activity as evidenced by electromyography (EMG). For example, EMG activity in the Pcm (which is further subdivided into pubovaginalis, puboperinealis and puboanalis) shows tonic, phasic or mixed EMG activity as the bladder fills, demonstrating the bilateral recruitment of the muscle. Additionally, the striated skeletal muscle of the pelvic floor forms a sling around the urogenital hiatus and rectum, acting as a sphincter and promoting their closure. Accordingly, the EMG activity indicates that the proper functioning of the pelvic floor requires the highly coordinated and timely response of the pelvic floor muscles (PFM).

Various pelvic floor disorders are due, at least in part, to the abnormal contraction or release of the muscles in the pelvic floor. Pelvic floor muscles (PFM) form a dome-shaped muscle complex which is critical in urinary continence, defecation and sexual functions, as the PFM provides organ support and actively participate in urinary and fecal continence as secondary sphincters. Their dysfunction is involved in pelvic floor disorders including Stress Urinary Incontinence (SUI), a condition that affects 30-60% of the female population and 5-15% of males, with aging and pregnancy exacerbating this condition.

The activity pattern of the pelvic floor muscles in persons having SUI has been observed to be disrupted when compared to healthy persons. In particular, those having SUI appear to have abnormal timing, reduced amplitude and atypical patterns of activity in the PFM. Further, the abnormal timing, reduced amplitude and atypical patterns in the PFM critically impact the ability of the PFM to maintain closure of the urethra. Accordingly, coughing, sneezing, high impact exercise (which lead to increased PFM EMG activity in those with SUI) may lead to urine leakage, and impact defecation and sexual function.

A. Implantation and Stimulation

Among the pelvic floor disorders, stress urinary incontinence, was studied in rabbits implanted with a neuromodulation device built in accordance with the present disclosure.

In particular, young multiparous (YM) and old multiparous (OM) rabbits were implanted with a neuromodulation device such as that disclosed herein.

In one study, a neuromodulation device was implanted and configured to engage with the tibial nerve. The tibial nerve is configured to innervate the Ism and Bsn.

Over a more than 10 month period, YM and OM rabbits received 10 min of stimulation at 2 Hz and 40 ∝A amplitudes 3 times per week while fully awake. An intravaginal pressure sensor was used to determine the effect of the applied stimulation, as contraction of the Ism and Bsn may be indicated by observed increased vaginal pressure.

Further, a wireless external stimulator may be used in connection with the neuromodulation devices that are anchored to the peripheral nerves. For example, the neuromodulation devices may be configured to stimulate the tibial nerve via an electromagnetic coupling with an antenna that is placed approximately 4-6 cm from the neuromodulation device. In some embodiments, the average maximum distance evoked in each animal for frequencies of 5 Hz with a 150 micro-second pulse width varied from 3-7 millimeters.

B. Selective and Independent Stimulation

The stimulation of the pelvic floor muscles such as the pubococcygeus and puborectalis can be used to close the urethral and rectal sphincters selectively and independently of each other. The stimulation can be done for unilateral contraction of the pelvic muscles and/or for simultaneous activation of multiple pelvic floor muscles.

Accordingly, in some embodiments, a method of treating a pelvic floor disorder may include having a plurality of neuromodulation devices, each of which is configured to stimulate and/or record from a separate nerve innervating a different pelvic floor muscle. In such an embodiment, the pelvic floor muscles may be contracted and/or released by applying selective stimulation to one or more of the nerves via their respective neuromodulation device. Further, stimulation of each muscle and/or nerve may be selectively stimulated, that is each nerve (and corresponding muscle) may receive stimulation having a different timing, amplitude, and frequency. In some embodiments, the parameters for selective stimulation of a nerve may be selected based on the nerve size, nerve fiber component and the like.

C. Parameters for Stimulation

As discussed above, parameters for the selective stimulation of a nerve may be optimized. Parameters such as the frequency, amplitude, and pulse duration may scale with the size of the nerves and may be tailored for optimal results in accordance with the condition of the innervated muscle. Although optimization with respect to the nervous system of the rabbits is discussed, it is envisioned that similar techniques may be applied in human and mammalian patients.

Figure 16A:
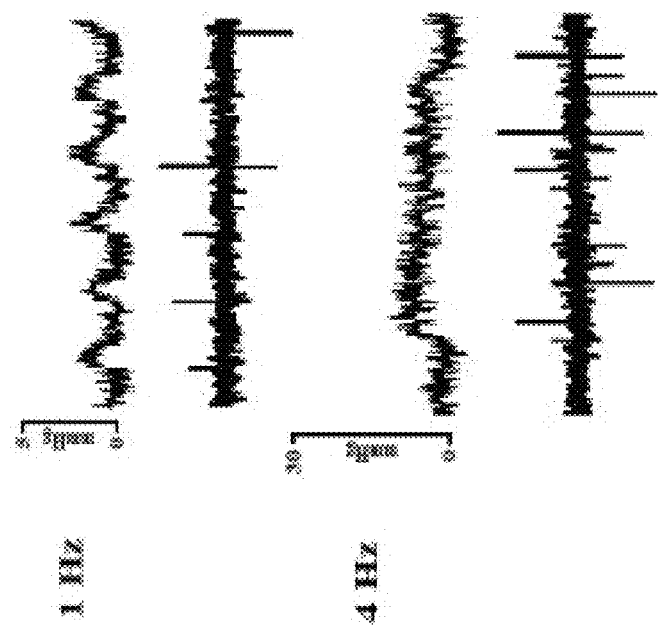
FIG. 16A presents graphs of urethral pressure and electromyography activity in rabbits in connection with an experiment built in accordance with embodiments of the present disclosure.
Figure 16B:
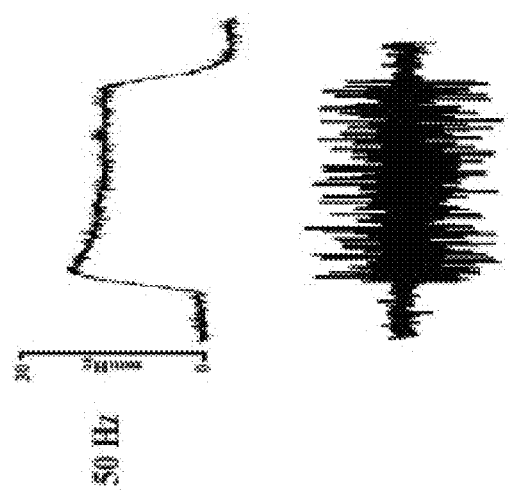
FIG. 16B is a graph of urethral pressure and electromyography activity in rabbits in connection with an experiment built in accordance with embodiments of the present disclosure.
Figure 16C:
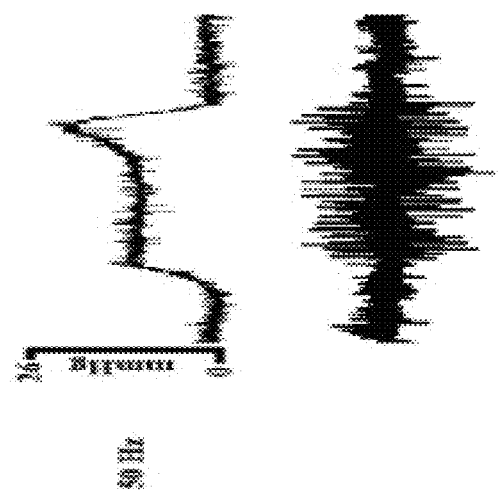
FIG. 16C is a graph of urethral pressure and electromyography activity in rabbits in connection with an experiment built in accordance with embodiments of the present disclosure.

FIGS. 16A-16C illustrate the effect of stimulation frequency on evoked activity. In particular, FIGS. 16A-16C illustrate the urethral pressure (top trace) and corresponding EMG activity (bottom trace) of two individual pelvic floor muscles, bulbospongiosus (16A-16B) and ischiocavernosus at various stimulation frequencies.

In particular, FIGS. 16A-16B illustrates that the urethral sphincter formed by the pelvic floor muscles open and closes if stimulated at 1 Hz. Increasing the stimulation frequency to 4 Hz closes this urethral sphincter, but maximal closure is achieved at a 50 Hz stimulation (top trace) and corresponding EMG activity (bottom trace). In agreement with difference in muscle mass and muscle fiber content, the optimal stimulation parameters for individual pelvic floor muscles are different.

FIG. 16B illustrates the urethral pressure (top trace) and corresponding EMG activity (bottom trace) at 50 Hz stimulation of the ischiocavernosus nerve. In particular, the optimal stimulation parameter for the Isn is 50 Hz with 10 microAmps and 0.5 millisec of pulse duration. With these parameters the maximal urethral closures in a female rabbit was obtained.

In comparison, FIG. 16C illustrates the urethral pressure (top trace) and corresponding EMG activity (bottom trace) at 50 Hz stimulation of the bulbospongiosus. Notably, as witnessed in the peak in the urethral pressure trace, stimulation of the bulbospongiosus at 50 Hz does not result in maximal muscle activity or urethral pressure as does stimulation of the ischiocavernosus at 50 Hz. Indeed, optimal stimulation between these nerve was different as the maximal urethral pressure on the bulbospongiosus was observed at a 100 Hz. Further, higher stimulation frequency causes muscle fatigue. Thus the parameters for optimal and safe activation of the pelvic floor muscles seem to be specific and tailored for the type and condition for individual pelvic floor nerves. Current volumetric stimulation methods cannot selectively control the stimulation parameters to specifications needed for individual pelvic floor nerves.

Accordingly, the optimal intensity for stimulation thresholds for each muscle varies according to their size. In the female rabbit, the threshold for rheobase depolarization in the ischiocavernosus nerve is 5-7 fold higher compared to that of the bulbospongiosus. This finding confirms that the parameters for optimal and safe stimulation are different for individual perineal and levator ani nerves and muscles, which very likely cannot achieve by the non-invasive methods used in conventional systems.

D. Immediate Benefits of Stimulation

As illustrated in FIGS. 16A-16C, stimulation of the pelvic nerves results in the immediate but modest increase in urethral or vaginal pressure in old and multiparous animals having partial nerve damage. Accordingly, neuromodulation can be used to evoke maximal number of motor efferent fibers acutely.

E. Chronic Benefits of Stimulation

Figure 17A:
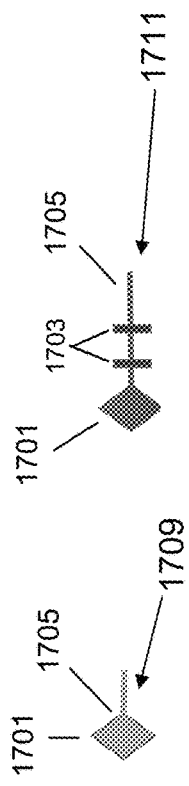
FIG. 17A provides a schematic representation of neurons in a first state in connection with an experiment built in accordance with embodiments of the present disclosure.
Figure 17B:
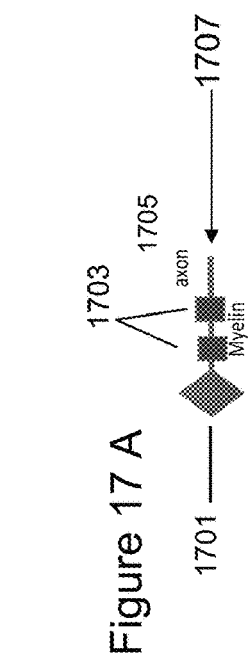
FIG. 17B provides a schematic representation of neurons in a second state in connection with an experiment built in accordance with embodiments of the present disclosure.
Figure 17:
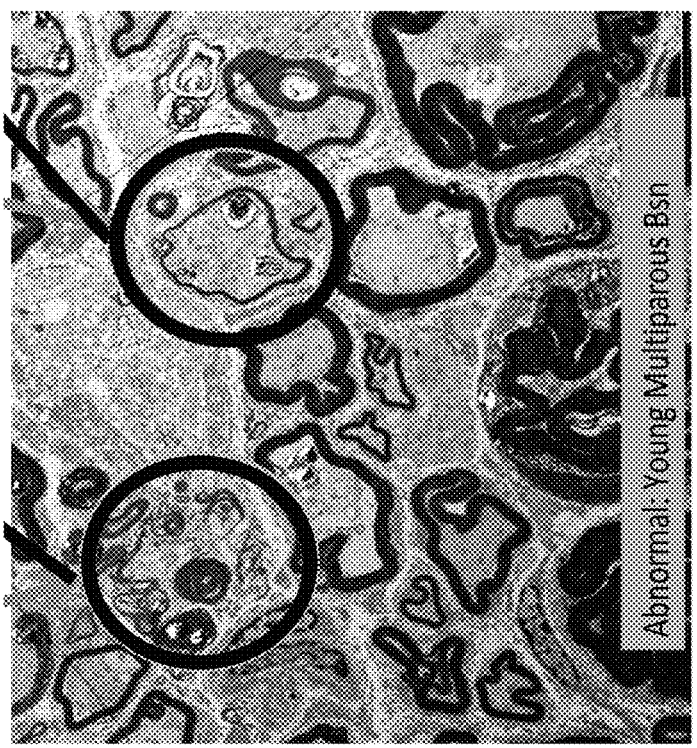
FIG. 17C provides a cross-sectional view of pelvic floor nerves in the first state of FIG. 17A in connection with an experiment built in accordance with embodiments of the present disclosure.
FIG. 17D provides a cross-sectional view of pelvic floor nerves in the second state of FIG. 17B in connection with an experiment built in accordance with embodiments of the present disclosure.
Figure 17:
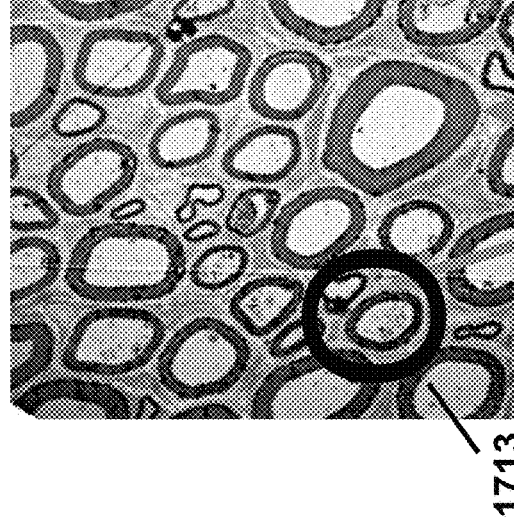

Similar to the human condition, YM rabbits have a reduction in total bladder volume threshold prior to voiding or leaking, and PFM activity (as observed by EMG recordings) is significantly reduced after vaginal birth. This may be due in part to damage to the axons, demyelination of the axons, and injured nerves. FIG. 17A and FIG. 17B provide a schematic representation of neurons in normal (FIG. 17A) and abnormal (FIG. 17B) conditions. As illustrated in FIG. 17A, the neuronal assembly 1707 includes a neuron 1701 having an axon 1705 extending therefrom, that is covered in myelin 1703. By contrast, in the abnormal state, either the myelin is completely missing 1709, or the myelin is greatly reduced and/or regenerating 1711. In particular, FIG. 17C and FIG. 17D provide cross-sectional views of pelvic floor nerves in connection with an experiment built in accordance with embodiments of the present disclosure. In particular, FIG. 17C illustrates a cross-section of individual axons 1713 in the pelvic floor nerves of a normal YM rabbit. In contrast, FIG. 17D illustrates a cross-section of individual axons in the pelvic floor nerves of a YM rabbit having stress urinary incontinence-like symptoms. As illustrated in the cross-section, the axons may suffer from Wallerian degeneration 1709, and appear injured. While muscle damage repairs spontaneously 1711, re-myelination is a slow process and thin myelinated axons are not normally functional. Furthermore, nerve injury in the adult may not regrow to re-establish functional muscle control. The combination of thin myelinated axons and injured ones, contributes to chronic PFM dysfunction. In nerves, trauma damaged Schwann cells (SCs), which are normally responsible for wrapping axons with insulating myelin layers, cause demyelination and nerve conduction failure. Nerve conduction is reduced in multiparous rabbits, a model that mimics the human condition in that they show SUI-like symptoms with deficient maximal urethral pressure to approximately 20-30% of that in a normal animal.

FIGS. 17A-17D illustrate nerve injury of pelvic floor nerves due to multiparity and aging demonstrated by both, the disintegration of the axon nerve fibers (ie., Wallerian degeneration), demyelination, and spontaneous regeneration of those axons indicated by a thin myelin sheet in large diameter axons in both young multiparous and old multiparous rabbits. This observation indicated that pelvic floor trauma damages the motor nerves that control the pelvic floor muscles contributing to SUI. As stimulation can be elicited acutely in young multiparous and old multiparous animals, this indicates that neuromodulation of pelvic floor nerves, can maximally activate those muscles despite partial nerve damage. The significant increase in evoked pelvic motor response after 2 weeks of daily treatments (10 min each) indicates that neuromodulation is also mediating the repair of nerve and muscle damage.

FIGS. 18A-18D provide schematics and experimental results for an experiment built in accordance with embodiments of the present disclosure. FIG. 18A provides a key for neuronal models. As illustrated, in a normal neuron, a healthy axon is surrounded by myelin. In an abnormal neuron, the axon is surrounded by thin myelin, which may be due in part to spontaneous repair. In a non-functional neuron, the axon is not surrounded by any myelin and is injured. In particular, FIG. 18B provides a schematic representation of pelvic floor neurons injured by multi-parity and/or aging such that the rabbit experiences limited pelvic floor muscle contractions. FIG. 18C illustrates the schematic configuration of neurons and muscles during acute stimulation. Further, FIG. 18C also shows the increased vaginal pressure during acute stimulation. FIG. 18D illustrates the schematic configuration of neurons and muscles during continued stimulation. As illustrated in FIG. 18D, the exponential increase in function (as evidenced by the exponential increase in mean vaginal pressure) after stimulation for 15 days is indicative of nerve/muscle repair.

As illustrated in FIG. 18D, vaginal pressure increased progressively reaching its maximum at 15 days after implantation, with an overall 3-fold strengthening of the PFM, and plateauing thereafter. More significantly, some OM implanted animals and treated continuously for 6 months, showed a remarkable improvement in bladder and urethral functions, resembling that observed in YN animals. These results confirmed that neuromodulation of selective PFM muscles can be used to correct urinary deficits, and revealed a new benefit for electrical stimulation of partially damaged nerves, that is to repair the nerve/muscle.

Although injured axons in the peripheral nervous system are able to spontaneously regenerate, in the adult, this regeneration is limited and frequently poor. However, the electrical stimulation of injured nerves, mediated the repair and functional nerve regeneration. Therefore, the exponential increase in pelvic floor muscle strength observed in FIG. 18D after two weeks of electrical stimulation to partially injured nerves, indicates an effect of the neuromodulation in nerve repair and functional regeneration of the pelvic nerves and muscles. Muscle strength by conventional methods for addressing stress urinary incontinence such as pelvic floor exercises do not show exponential gains, but it is rather linear in nature.

Example 9

Configurations for the Neuromodulation Device

Figure 19:
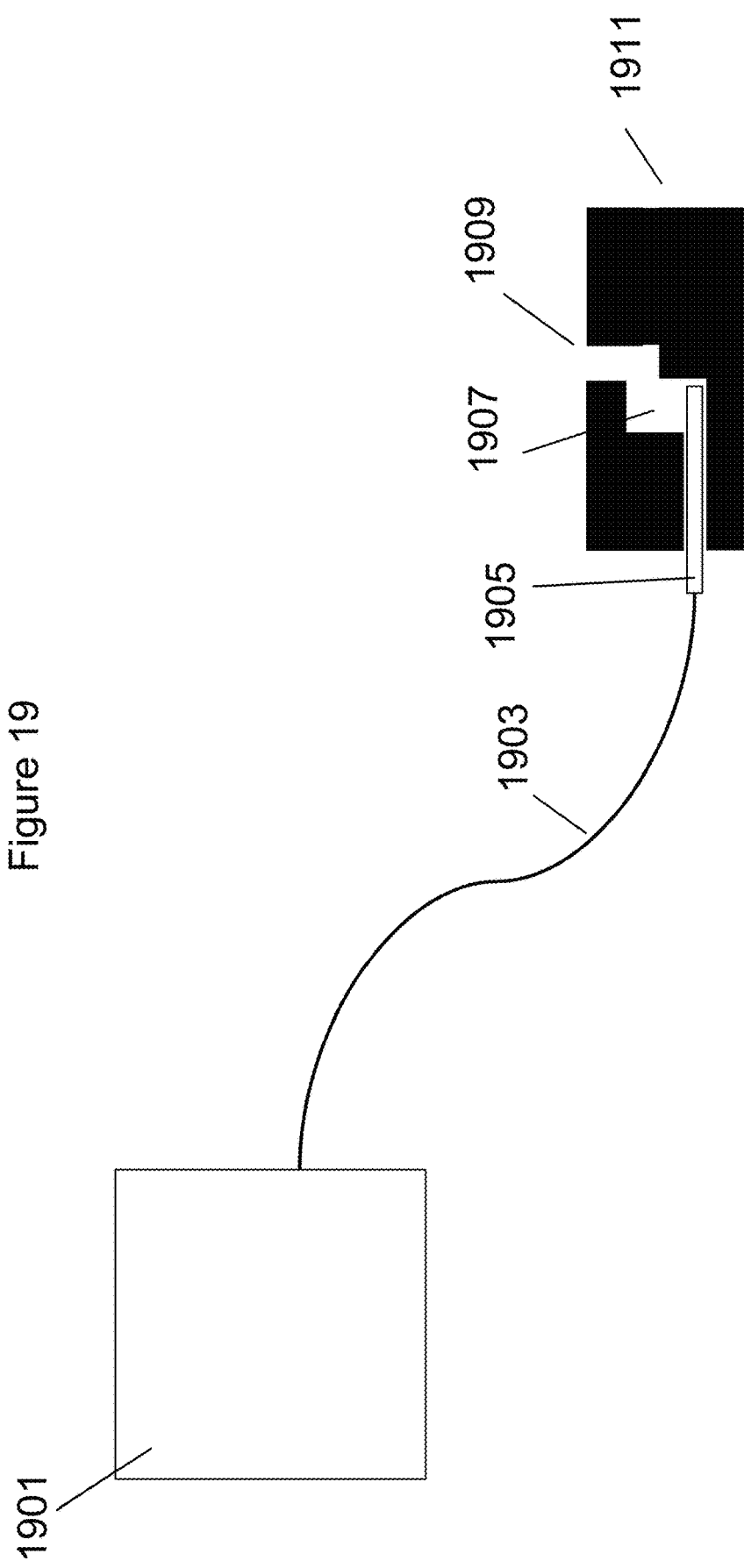
FIG. 19 provides a schematic representation of a neuromodulation device and external system in accordance with embodiments of the present disclosure.

FIG. 19 provides a schematic representation of a neuromodulation device and external system in accordance with embodiments of the present disclosure. In the illustrated embodiment, a stimulation system includes a battery powered pulse generator and electronic controller 1901 connected to an electrode 1905 by way of a conductive wire 1903. As illustrated, the electrode is a part of the chamber 1907 of the neuromodulation device 1911. As illustrated, the neuromodulation device 1911 may include a "L" shaped channel 1909 configured to receive a nerve. In some embodiments, at least a portion of the diameter of the channel 1901 may be smaller than the diameter of the target nerve. Accordingly, the target nerve may be temporarily be reversibly compressed or stretched, and slid along the channel until the target nerve is held within the chamber 1907. In some embodiments, the chamber 1907 may have a diameter greater than the nerve, such that the nerve is not compressed or stretched within the chamber 1907. Alternatively, the chamber 1907 may have a diameter smaller than the nerve. Accordingly, in such an embodiment at least a portion of the nerve may extend into the channel 1909 while a substantial portion of the nerve is contained within the chamber 1907. Further, the chamber 1907 may provide an isolated fluidic environment that allows for the targeted and specific stimulation of the portion of the nerve held within the chamber 1907.

Figure 20:
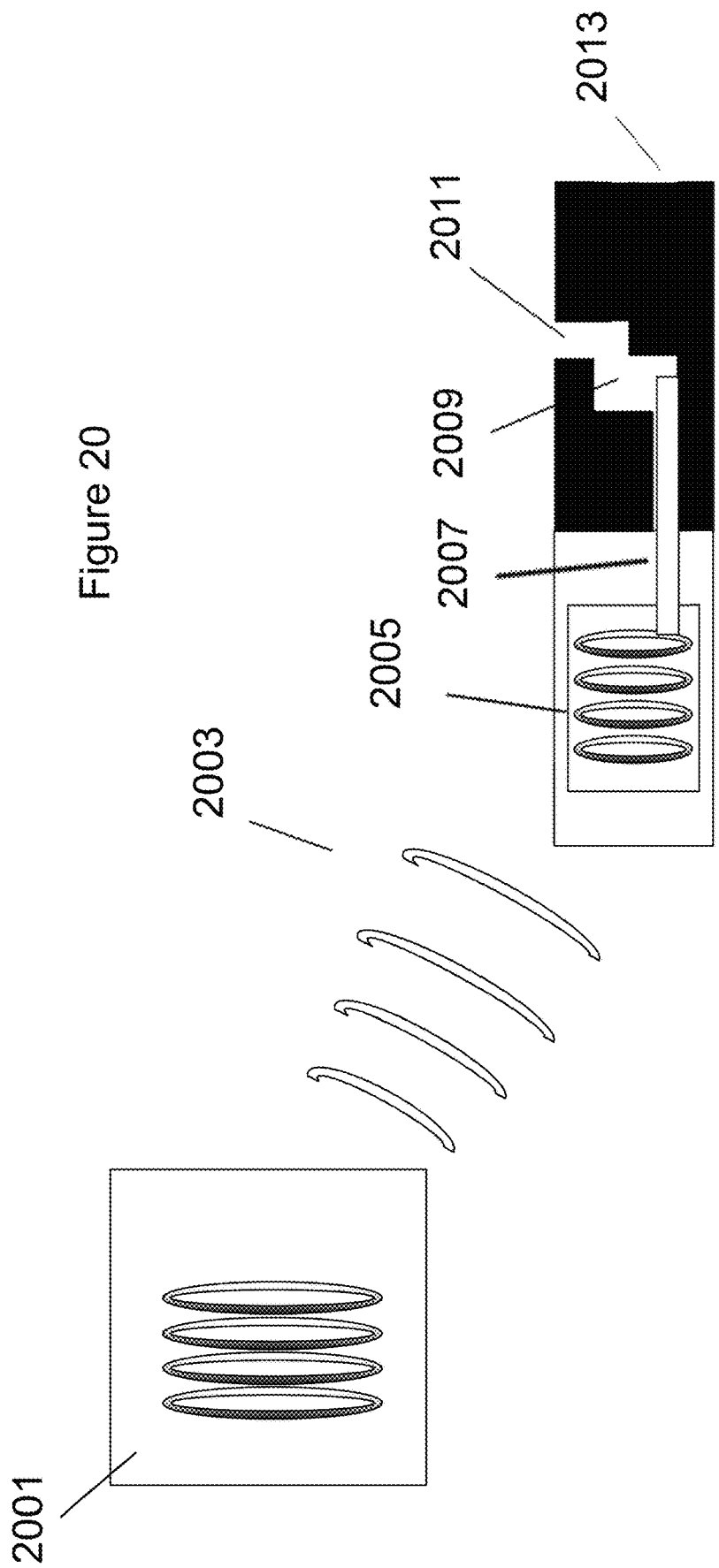
FIG. 20 provides a schematic representation of a neuromodulation device and external system in accordance with embodiments of the present disclosure.

FIG. 20 provides a schematic representation of a neuromodulation device and external system in accordance with embodiments of the present disclosure. In the "wireless" embodiment of the neuromodulation device illustrated in FIG. 20, the device may include an external battery powered pulse generator and electronic controller 2001 that includes a coil that transmits power, data and control signals to the wireless neuromodulation device 2013. In particular, an electromagnetic field 2003 may be used to couple the pulse generator and electronic controller 2001 to the wireless neuromodulation device 2013. Corresponding electronics and magnetic induction coil 2005 in the neuromodulation device 2013 may be connected to the conductive material used as electrode(s) 2007. The electrodes may form part of the chamber 2009. As discussed with respect to the embodiments disclosed herein, the neuromodulation device may include a chamber 2009 configured to receive the nerve, and a channel 2011 (or "L-shaped slit") through which the nerve may pass as it is placed in the chamber 2009.

Figure 21:
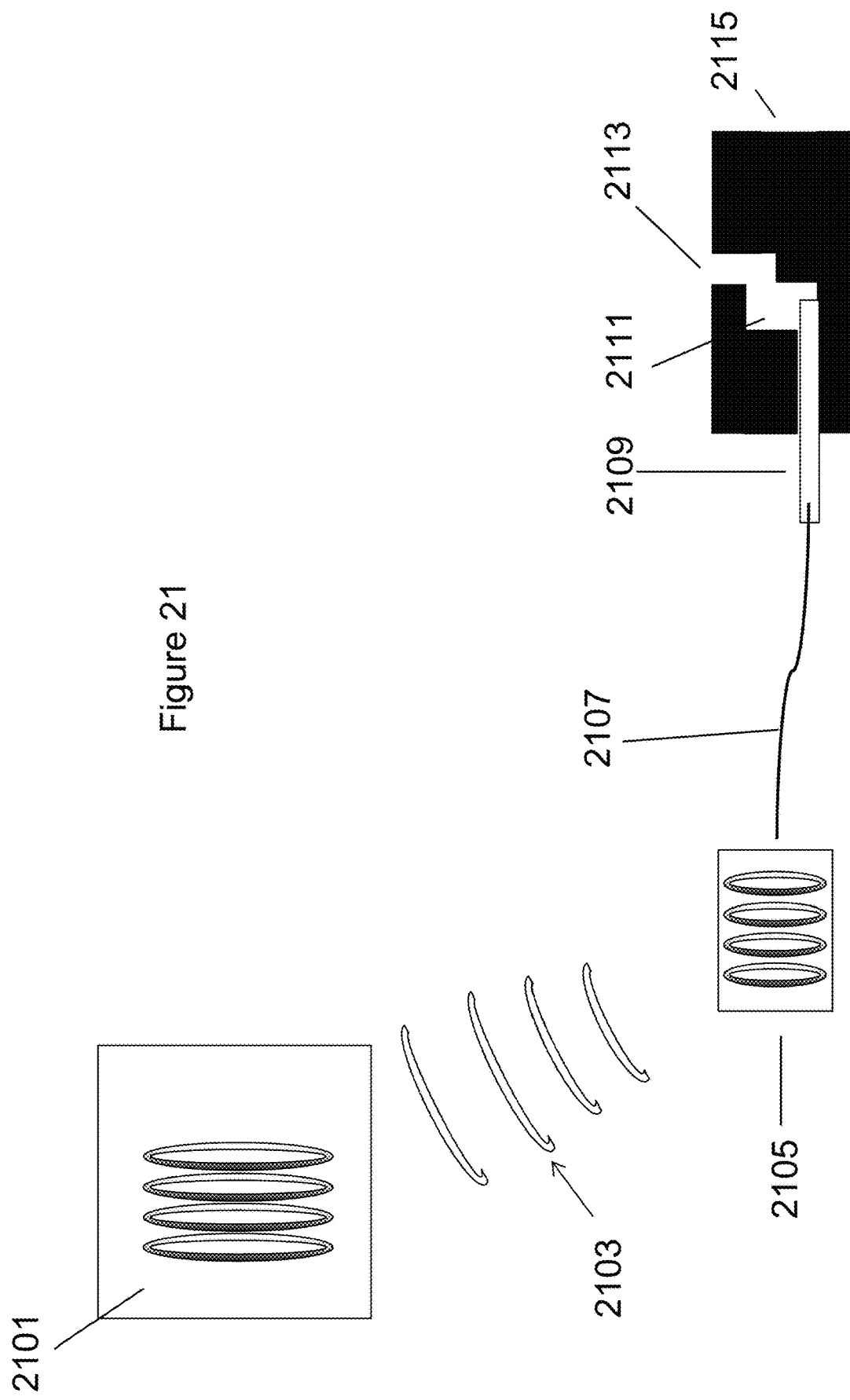
FIG. 21 provides a schematic representation of a neuromodulation device and external system in accordance with embodiments of the present disclosure.

FIG. 21 provides a schematic representation of a neuromodulation device and external system in accordance with embodiments of the present disclosure. In the wireless embodiment illustrated in FIG. 21, an external battery powered pulse generator and electronic controller 2101 with a coil that transmits power, data and control signals to the neuromodulation device 2115. As illustrated in FIG. 21, an electromagnetic field 2103 couples with the coil 2105 of the neuromodulation device 2115. In some embodiments, the electronics and coil 2105 may be spaced apart and implanted separately from the stimulating elements of the neuromodulation device 2115. In some embodiments, the location of the electronics and coil 2105 may be chosen to optimize the signal strength and quality of transmissions between the external pulse generator and electronic controller 2101 and the neuromodulation device 2115. Further, the separate electronics and coil 2105 configuration may lead to reduced battery requirements and applied voltage and/or amplitude. Conductive wire 2107 may couple the electronics and coil 2105 to the neuromodulation device 2115, and more particularly to the electrodes 2109 which may be located within a chamber 2111. As discussed with respect to the embodiments disclosed herein, the neuromodulation device 2115 may include a chamber 2111 configured to receive the nerve, and a channel 2113 (or "L-shaped slit") through which the nerve may pass as it is placed in the chamber 2111.

The embodiment illustrated in FIG. 21 may provide many advantages when compared to conventional systems. In particular, connecting an implanted electronics with a receiver coil to the neuromodulation device effectively separates the receiver coil, which allows a medical practitioner to implant the receiver coil in the same location and orientation relative to the hard tissue structures of the body, regardless of where the electrode and neuromodulation device is positioned. This consistency in the location and orientation of the receiver coil allows for a more consistent, efficient and reliable coupling and induction in the implanted coil and electronics. This may help avoid variability in stimulation or variability in external coil position or orientation requirements.

Figure 22:
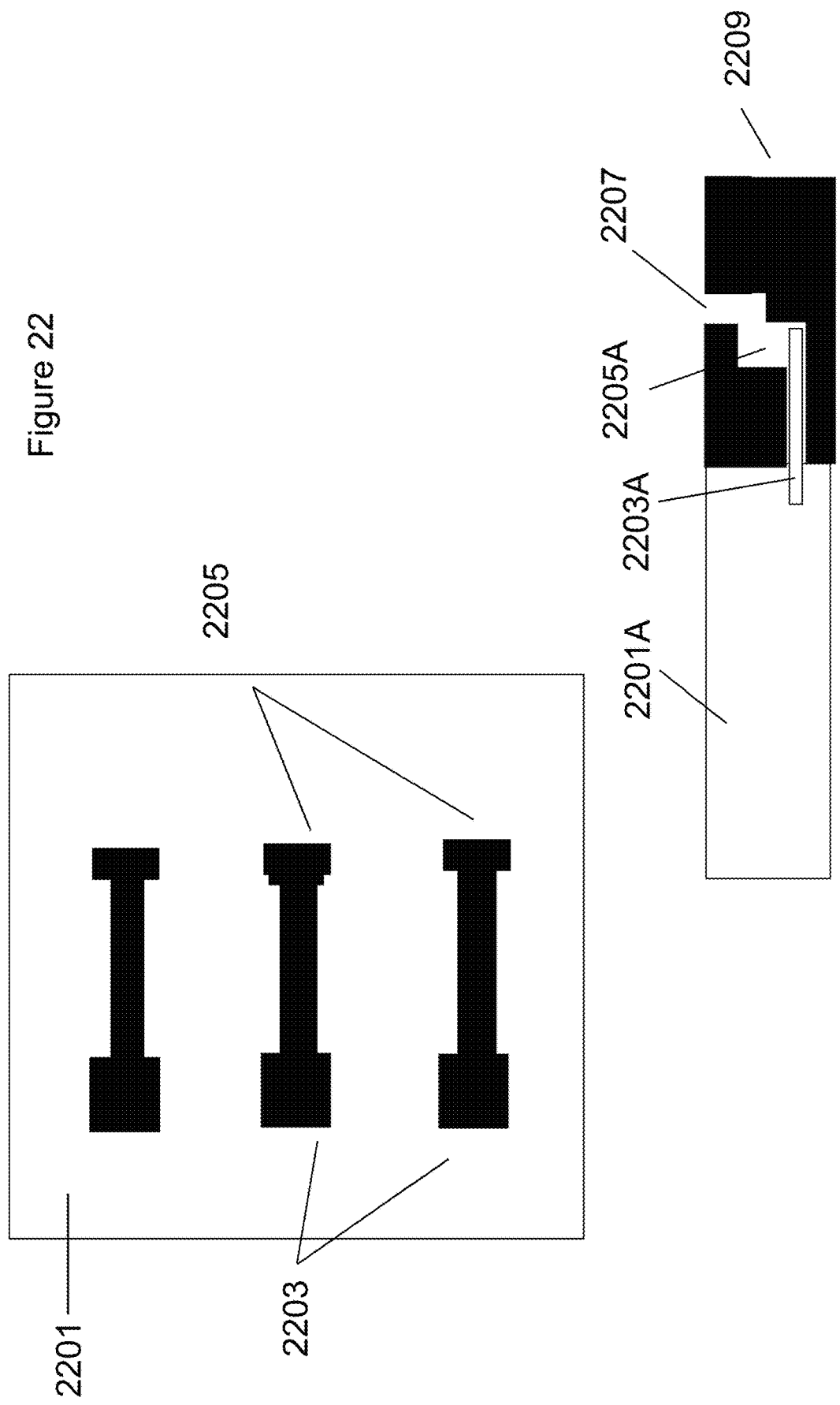
FIG. 22 provides a schematic representation of a neuromodulation device and external system in accordance with embodiments of the present disclosure.

FIG. 22 provides a schematic representation of a neuromodulation device and external system in accordance with embodiments of the present disclosure. A bottom view 2201 of the neuromodulation device illustrates that the neuromodulation device includes insulated material that forms the body of the device, and conductive material 2203 used as electrode(s) with contact pads to connect to wires of wireless electronics, and a contact pad for nerve stimulation/recording 2205. A side view 2209 of the neuromodulation device illustrates the insulated material that forms the body of the device 2201A, the conductive material used as electrode(s) 2203A, the chamber 2205A of the neuromodulation device where the nerve is placed after implantation and the channel 2207 through which the nerve is inserted or engaged with the neuromodulation device 2209.

Alternative embodiments, may include a neuromodulation device shaped as a clothespin, dovetail, and/or vase. Each of the disclosed designs may be configured to include a channel having a diameter smaller than that of the target nerve such that the nerve is stretched prior to engaging with the chamber of the neuromodulation device.

Example 10

Impacts of Electrical Stimulation Using a Neuromodulation Device

Figure 23:
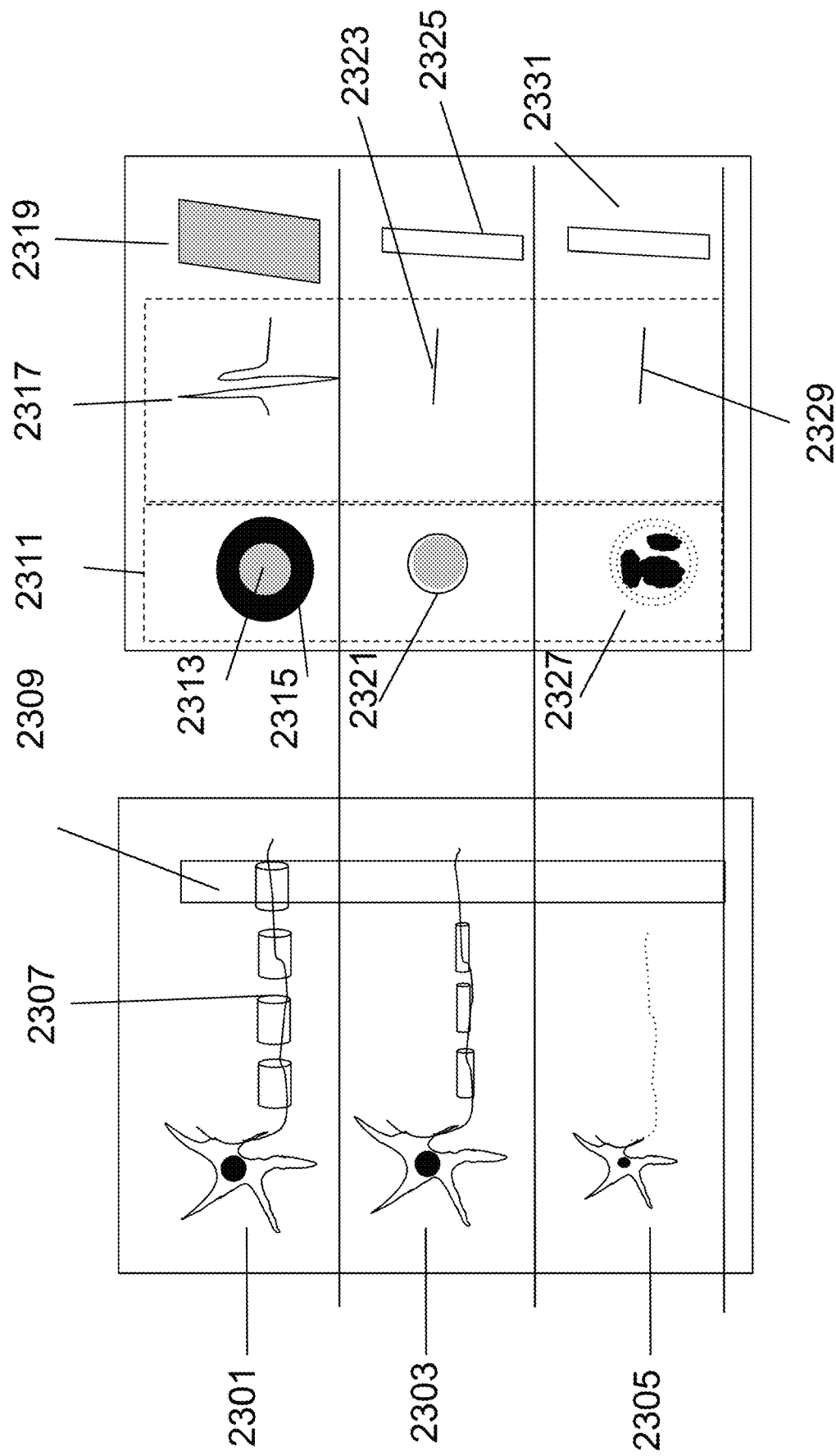
FIG. 23 provides a schematic representation of neurons as observed prior to an experiment conducted in accordance with embodiments of the present disclosure.

FIG. 23 provides a schematic representation of neurons as observed prior to an experiment conducted in accordance with embodiments of the present disclosure. The top panel illustrates a healthy system having a nerve cell with a healthy cell body 2301 connected to a myelinated axon 2307. As illustrated by the cross-section 2309, the healthy system includes an axon 2312 surrounded by myelin 2315. The illustrated healthy system would be able to conduct an action potential 2317 and would be expected to contract a muscle 2319.

By contrast, the middle panel illustrates an injured system, where the cell body may be healthy 2303, however, the insulating myelin layers may be damaged. Accordingly, a cross section 2309 of the system may illustrate that the axon 2321 has reduced or damaged myelin. Further, the axon may not be able to conduct an action potential 2323, and contraction of the muscle 2325 may be impaired.

Additionally, the middle panel of FIG. 23 illustrates an injured system, where although the cell body 2305 is present, the axon may be at least partial disintegrated, and void of myelin. This may correspond to wallerian degeneration 2327 of the axon. Further the nerve may be incapable of conducting an action potential 2329, which may in turn lead to muscle paralysis and/or reduced muscle mass 2331.

Figure 24:
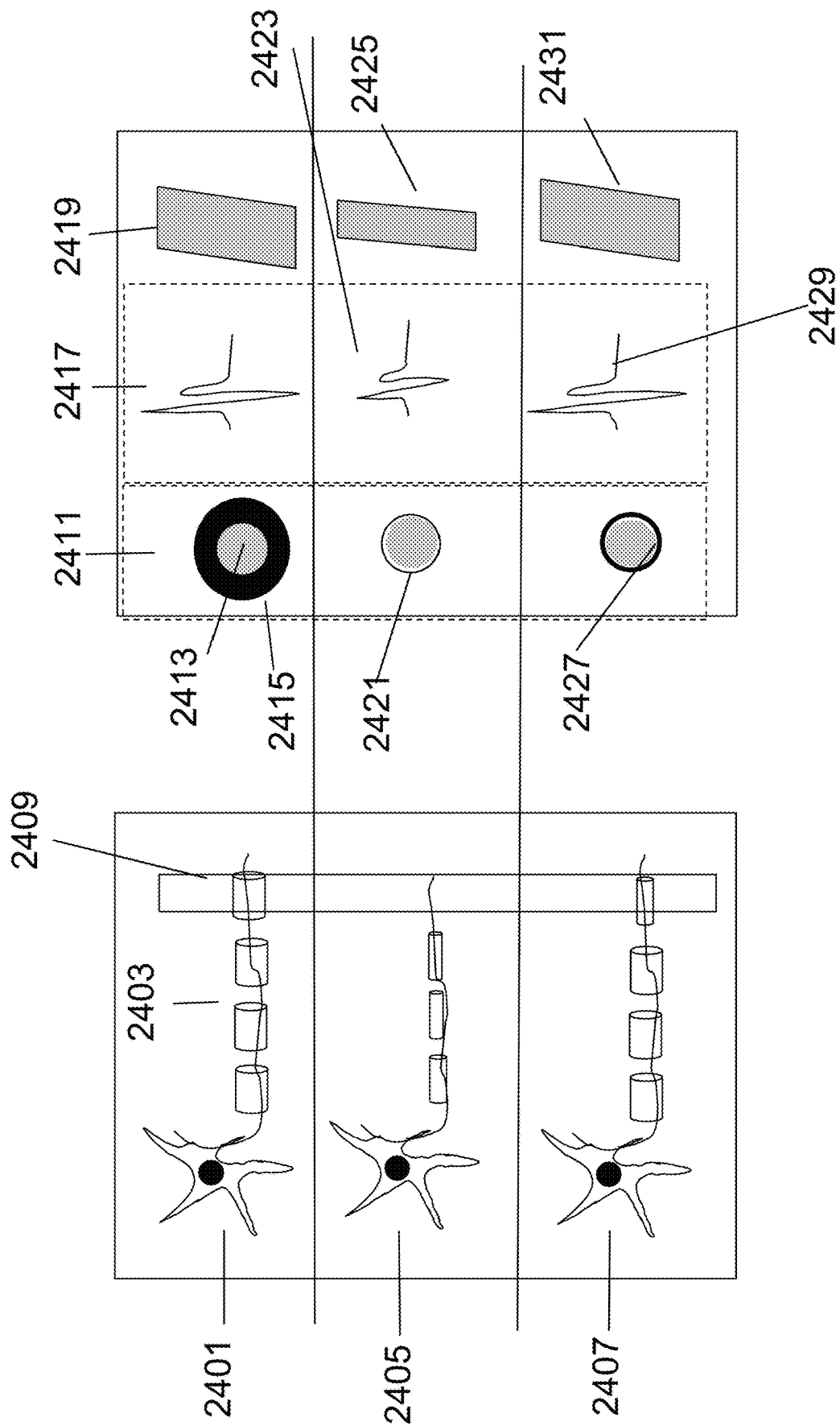
FIG. 24 provides a schematic representation of neurons as observed after an experiment conducted in accordance with embodiments of the present disclosure.

FIG. 24 provides a schematic representation of neurons as observed after an experiment conducted in accordance with embodiments of the present disclosure. In particular, FIG. 24 illustrates the effect of neuromodulation on undamaged and damaged nerve cells in the pelvic area. A cross section 2409 across the three panels was taken.

The top panel of FIG. 24 illustrates the behavior of a healthy nerve cell 2401, having an axon sheathed in myelin 2304. As illustrated in cross section 2411, the corresponding axon 2413 is covered in myelin 2415, and capable of conducting an action potential 2417. Additionally, the muscle 2419 is capable of contraction and has normal muscle mass.

The middle panel of FIG. 24 illustrates a nerve cell 2405 with damage to their insulated myelin layers. As illustrated in the cross-section 2411, the axon 2421 may have reduced or absent myelin layers. However, after treatment with electrical stimulation, action potential conductance 2423 and muscle contraction 2425 may be observed.

Further, the bottom panel of FIG. 24 illustrates a nerve cell 2407 with partially re-myelinated axons still having partial disintegration of the axon and no myelin 2427. However, after treatment with electrical stimulation, action potential conductance 2429 and muscle contraction 2431 may be observed.

Example 11

Stimulation Parameters for Treating Pelvic Floor Disorders Using a Neuromodulation Device Stimulation parameters for operating a neuromodulation device in rabbits and humans are presented below.

A. Rabbit Model

In some embodiments, treating stress urinary incontinence by initiating the response and/or contraction of muscles acutely may include applying an electrical stimulation at a frequency between 0.5 and 1000 Hz, having an amplitude between 0.5 and 20 mAmps, and a voltage between 0.1-1 V in rabbits. An electrical stimulation pulse used to induce an acute response and/or contraction of muscle in order to treat stress urinary incontinence, may have a pulse duration between about 0.1 and 10 ms. Further, the applied electrical stimulation may have a square monopolar, cathodic, bipolar balanced shape and the like. In some embodiments, a stimulation may be applied for a period of 5-100 minutes, as often as 1 times a day. In some embodiments, a stimulation may be applied five times, for a duration of 10 minutes each.

In some embodiments, repairing pelvic floor muscles (i.e., initiating a chronic response, repair or regeneration of axons) may require applying a sustained electrical stimulation to the target nerve via one or more electrodes positioned within the chamber of the neuromodulation device thereby initiating a repair process in the target nerve. In some embodiments, the sustained electrical stimulation may include an electrical stimulation at a frequency between about 1-100 Hz, having an amplitude between about 0.5-20 mAmps and/or voltage between 0.5-20 mV in rabbits. The electrical stimulation pulse to initiate a chronic response and/or the repair or regeneration of axons may include the application of an electrical pulse having a duration between 0.2-10 ms applied for between 5-100 minutes, 1 time per day, 2-5 days a week, for a period of 2-20 weeks. The applied stimulation may have a square monopolar, cathodic, or bipolar balanced shape.

In some embodiments, the neuromodulation device may also be used to apply an electrical stimulation configured to block the electrical activity in an axon. In particular, high frequency stimulation may be used for blocking. For example, an electrical stimulation having a frequency between about 1 and 100 KHz, an amplitude of 0.5-20 mAmps and/or a voltage between 0.1-7V may be applied continuously, on a daily basis as needed. The electrical stimulation may be applied using electrical pulses having a pulse duration between about 0.1-0.5 ms. In some embodiments, the applied electrical stimulation may have a sigmoid shape.

It is envisioned that optimal stimulation parameters for each nerve and/or muscle target may be determined via experimentation with the neuromodulation device.

B. Human Applications

As discussed above, the above disclosed stimulation parameters in rabbits may be scaled for stimulation in mammals including humans. The amount of current or voltage used for electrical stimulation in humans may be proportional to the size of the nerve (and scaled proportionally from rabbits, rodents, and the like). Further, the duration and frequency of applying electrical stimulation may be modified in humans in accordance with the severity of the condition, age, and co-morbidities of the human.

In some embodiments, it is envisioned that a neuromodulation device configured to treat stress urinary incontinence in humans by initiating the response and/or contraction of muscles acutely may include applying an electrical stimulation at a frequency between 0.5 and 1000 Hz, having an amplitude between 0.5 and 20 mAmps, and a voltage between 0.1-1 V. An electrical stimulation pulse used to induce an acute response and/or contraction of muscle in order to treat stress urinary incontinence, may have a pulse duration between about 0.5 and 100 ms. Further, the applied electrical stimulation may have a square monopolar, cathodic, bipolar balanced shape and the like. In some embodiments, a stimulation may be applied for a period of 5-120 minutes, as often as 1 times a day.

In some embodiments, repairing pelvic floor muscles (i.e., initiating a chronic response, repair or regeneration of axons) in humans may require applying a sustained electrical stimulation to the target nerve via one or more electrodes positioned within the chamber of the neuromodulation device thereby initiating a repair process in the target nerve in humans. In some embodiments, the sustained electrical stimulation may include an electrical stimulation at a frequency between about 1-1000 Hz, having an amplitude between about 0.5-200 mAmps and/or voltage between 0.5-300 mV in humans. The electrical stimulation pulse to initiate a chronic response and/or the repair or regeneration of axons may include the application of an electrical pulse having a duration between 0.2-100 ms applied for between 5-120 minutes, 1-2 times per day, 3-5 days a week, for a period of 5-20 weeks. The applied stimulation may have a square monopolar, cathodic, or bipolar balanced shape.

In some embodiments, the neuromodulation device may also be used to apply an electrical stimulation configured to block the electrical activity in an axon of a human patient. In particular, high frequency stimulation may be used for blocking. For example, an electrical stimulation having a frequency between about 1 and 100 KHz, an amplitude of 0.5-200 mAmps and/or a voltage between 1-20V may be applied continuously, on a daily basis as needed. The electrical stimulation may be applied using electrical pulses having a pulse duration between about 0.1-5 ms. In some embodiments, the applied electrical stimulation may have a sigmoid shape.

Example 11

Using a Neuromodulation Device to Treat or Alleviate Stress Urinary Incontinence As disclosed herein, a neuromodulation device may be used to apply a direct electrical stimulation to a target nerve associated with stress urinary incontinence. The application of direct electrical stimulation may allow for the control of parameters including frequency, amplitude, and other factors that allows for efficient nerve therapy.

In comparison to conventional systems that typically utilize a method of volume conduction, in the disclosed systems and methods stimulation is provided more efficiently, and closer to the target nerve (thereby reducing the effective voltage and/or amplitude needed).

Further, stimulation may be used not only to acutely contract muscles so as to prevent leakage or micturition but also to enable nerve repair and improve muscular contraction of the target pelvic floor muscles and related sphincters. In particular, to address stress urinary incontinence, the pubococcygeus and/or coccygeus and/or levator ani and/or ischiocavernosus and/or bulbospongiosus and/or Pudendal nerve(s) may be stimulated. Further, in some examples, the neuromodulation device may be configured to stimulate directly near a target nerve rather than a larger proximal nerve. For example, if the nerve is damaged in the pubococcygeus nerve branch or distal small branches, the neuromodulation device may be configured to stimulate the pubococcygeus nerve rather than the levator ani nerve.

The stimulation of these nerves may lead to improved efficacy of action potential propagation and nerve activation, as well as improved contraction of target muscles which may include the pubococcygeus and/or coccygeus and/or ischiocavernosus and/or bulbospongiosus muscles. The effective contraction of the pubococcygeus and coccygeus muscles operates by pulling the urethra dorsally and thereby aids in urinary continence. When the ischiocavernosus and/or bulbospongiosus muscles are effectively contracted they provide support of the bladder to properly fill, contribute to urinary continence, and prevent the bladder and proximal urethra from dropping down and poorly filling the bladder, which would contribute to urinary incontinence. Further, stimulation of these muscles has been shown to improve the closure of the external urethra sphincter, which aids in urinary continence.

Additionally, for men who have had a radical prostatectomy, the importance of the mediation of the bulbospongiosus and ischiocavernosus are particularly important given the removal of the tissue that mechanically interacts with these muscles.

Example 12

Using a Neuromodulation Device to Treat or Alleviate Fecal Incontinence

As disclosed herein, a neuromodulation device may be used to apply a direct electrical stimulation to a target nerve associated with fecal incontinence. The application of direct electrical stimulation may allow for the control of parameters including frequency, amplitude, and other factors that allows for efficient nerve therapy.

In particular, stimulation may be used to acutely contract and/or repair and improve the muscular contraction of the puborectalis and/or levator ani nerve(s) and associated muscles. The effective contraction of the puborectalis muscle acts to maintain the anorectal angle at rest providing fecal continence. Stimulation of the puborectalis and/or levator ani nerve(s) is also associated with improved closure of the anal sphincter.

Example 13

Using a Neuromodulation Device to Treat or Alleviate Sexual Dysfunction in Men

As disclosed herein, a neuromodulation device may be used to apply a direct electrical stimulation to a target nerve associated with sexual dysfunction in men. The application of direct electrical stimulation may allow for the control of parameters including frequency, amplitude, and other factors that allows for efficient nerve therapy.

In particular, stimulation of the dorsal nerve of the penis, the bulbospongiosus and/or the ischiocavernosus nerves may be associated with improved arousal (e.g., sensation and penile erection), and ability to ejaculate.

What is claimed is:

1. A method comprising:
    providing an implantable neuromodulation device having
        a chamber configured to apply an electrical stimulation or record nerve activity, the chamber having a cross-sectional chamber inner dimension;
        a channel fluidly connecting the chamber to outside of the device, the channel being defined by a plurality of wall portions defining a central line of the channel, the central line having at least two segments that are oriented transversely to each other, such that passing a nerve through the channel between the chamber and the outside of the device requires changing direction; and
        one or more electrodes;
    engaging a target nerve with the implantable neuromodulation device by:
        stretching the target nerve so as to reduce a maximum cross-sectional dimension of at least a portion of the target nerve by 10% to 40% to define a reduced nerve, so as to move the reduced nerve through the channel, the channel having a cross-sectional channel inner dimension that is more than 10% smaller than the maximum cross-sectional dimension of the at least a portion of the target nerve, but less than 40% smaller than the maximum cross-sectional dimension of the at least a portion of the target nerve, wherein the cross-sectional channel inner dimension is less than the cross-sectional chamber inner dimension;
        moving the reduced nerve into the chamber of the neuromodulation device by (a) moving the reduced nerve in a first direction through the channel, and (b) moving the reduced nerve in a second direction through the channel, the chamber being fluidly connected to the channel;
        relaxing the target nerve so as to increase the cross-sectional dimension of the reduced nerve in the chamber; and
        applying an electrical stimulation to the target nerve, or recording the activity of the target nerve, via the one or more electrodes positioned within the chamber of the neuromodulation device.

2. The method of claim 1, wherein the target nerve comprises one of iliococcygeus nerve, pubococcygeus nerve, coccygeus nerve, puborectalis nerve, bulbospongiosus, ischiocavernosus nerve, clitoral nerve, dorsal nerve, branch nerves of the pudendal nerve, branch nerves of the levator ani nerve, branch nerves of the coccygeal plexus, and/or branch nerves of the sacral plexus.

3. The method of claim 1, wherein applying an electrical stimulation initiates a response from the target nerve, wherein the response stimulates, modulates, or blocks the target nerve activity.

4. The method of claim 1, wherein the applied electrical stimulation comprises applying an electrical stimulation having a voltage between 0.1 and 1.0 V.

5. The method of claim 1, wherein the applied electrical stimulation has one of a square monopolar, cathodic, or bipolar balanced shape.

6. The method of claim 1, wherein the applied electrical stimulation comprises an electrical pulse having a duration of between 0.1 ms and 10 ms.

* * * * *